(12) United States Patent
Shenoy et al.

(10) Patent No.: US 9,931,136 B2
(45) Date of Patent: Apr. 3, 2018

(54) METHOD AND APPARATUS FOR ALTERING BIOMECHANICS OF ARTICULAR JOINTS

(71) Applicant: Cotera, Inc., Menlo Park, CA (US)

(72) Inventors: Vivek Shenoy, Redwood City, CA (US); Hanson S. Gifford, III, Woodside, CA (US); Mark Deem, Mountain View, CA (US)

(73) Assignee: The Foundry, LLC, Menlo Park, CA (US)

( * ) Notice: Subject to any disclaimer, the term of this patent is extended or adjusted under 35 U.S.C. 154(b) by 0 days.

(21) Appl. No.: 15/017,098

(22) Filed: Feb. 5, 2016

(65) Prior Publication Data
US 2016/0213402 A1  Jul. 28, 2016

Related U.S. Application Data

(63) Continuation of application No. 13/843,128, filed on Mar. 15, 2013, now Pat. No. 9,278,004, and a
(Continued)

(51) Int. Cl.
*A61F 2/40* (2006.01)
*A61B 17/56* (2006.01)
(Continued)

(52) U.S. Cl.
CPC ............ *A61B 17/56* (2013.01); *A61B 17/562* (2013.01); *A61B 17/8872* (2013.01);
(Continued)

(58) Field of Classification Search
CPC ...... A61F 2/40; A61F 2/4003; A61F 2/30734; A61F 2/4657; A61F 2/3886; A61B 17/56;
(Continued)

(56) References Cited

U.S. PATENT DOCUMENTS 2,632,440 A  3/1953 Hauser
2,877,033 A  3/1959 Koetke
(Continued)

FOREIGN PATENT DOCUMENTS

CA  1205602  6/1986
CN  2788765  6/2006
(Continued)

OTHER PUBLICATIONS

PCT International Search Report and Written Opinion dated Oct. 20, 2010, for related application PCT/US2010/046996 filed Aug. 27, 2010 entitled "Method and Apparatus for Force Redistribution in Articular Joints"; Vivek Shenoy, Mark Deem and Hanson Gifford.
(Continued)

*Primary Examiner* — Alvin Stewart
(74) *Attorney, Agent, or Firm* — Downs Rachlin Martin PLLC

(57) ABSTRACT

Pathology of the human knee can arise from excessive and/or uneven loading of regions within the joint. Methods and apparatus are disclosed that enable displacement of soft tissue around the knee, without displacing or severing bone thereby altering the mechanical load distribution within the joint in a less invasive manner than previous techniques.

29 Claims, 37 Drawing Sheets

Related U.S. Application Data continuation-in-part of application No. 12/870,462, filed on Aug. 27, 2010, now Pat. No. 8,597,362.

(60) Provisional application No. 61/620,756, filed on Apr. 5, 2012, provisional application No. 61/695,406, filed on Aug. 31, 2012, provisional application No. 61/237,518, filed on Aug. 27, 2009, provisional application No. 61/288,692, filed on Dec. 21, 2009.

(51) Int. Cl.
    *A61B 17/88* (2006.01)
    *A61F 2/38* (2006.01)

(52) U.S. Cl.
    CPC ...... *A61F 2/3886* (2013.01); *A61B 2017/564* (2013.01); *A61B 2017/565* (2013.01)

(58) Field of Classification Search
    CPC .............. A61B 17/562; A61B 17/8872; A61B 2017/568
    USPC .......... 623/20.14, 19.11–19.14, 20.15, 20.16
    See application file for complete search history.

(56) References Cited

U.S. PATENT DOCUMENTS

| | | | |
|---|---|---|---|
| 3,242,922 A | 3/1966 | Thomas | |
| 3,648,294 A | 3/1972 | Shahrestani | |
| 3,681,786 A | 8/1972 | Lynch | |
| 3,779,654 A | 12/1973 | Horne | |
| 3,872,519 A | 3/1975 | Giannestras et al. | |
| 3,875,594 A | 4/1975 | Swanson | |
| 3,879,767 A | 4/1975 | Stubstad | |
| 3,886,599 A | 6/1975 | Schlien | |
| 3,889,300 A | 6/1975 | Smith | |
| 3,902,482 A | 9/1975 | Taylor | |
| 3,964,106 A | 6/1976 | Hutter, Jr. et al. | |
| 3,988,783 A | 11/1976 | Treace | |
| 4,007,495 A | 2/1977 | Frazier | |
| 4,041,550 A | 8/1977 | Frazier | |
| 4,052,753 A | 10/1977 | Dedo | |
| 4,054,955 A | 10/1977 | Seppo | |
| 4,069,518 A | 1/1978 | Groth, Jr. et al. | |
| 4,156,944 A | 6/1979 | Schreiber et al. | |
| 4,158,894 A | 6/1979 | Worrell | |
| 4,164,793 A | 8/1979 | Swanson | |
| 4,187,841 A | 2/1980 | Knutson | |
| 4,246,660 A | 1/1981 | Wevers | |
| 4,285,070 A | 8/1981 | Averill | |
| 4,308,863 A | 1/1982 | Fischer | |
| 4,353,361 A | 10/1982 | Foster | |
| 4,367,562 A | 1/1983 | Gauthier | |
| 4,470,158 A | 9/1984 | Pappas et al. | |
| 4,501,266 A | 2/1985 | McDaniel | |
| 4,570,625 A | 2/1986 | Harris | |
| 4,576,158 A | 3/1986 | Boland | |
| 4,621,627 A | 11/1986 | DeBastiani et al. | |
| 4,637,382 A | 1/1987 | Walker | |
| 4,642,122 A | 2/1987 | Steffee | |
| 4,696,293 A | 9/1987 | Ciullo | |
| 4,759,765 A | 7/1988 | Van Kampen | |
| 4,759,766 A | 7/1988 | Buettner-Janz et al. | |
| 4,776,851 A | 10/1988 | Bruchman et al. | |
| 4,778,472 A | 10/1988 | Homsy et al. | |
| 4,846,842 A | 7/1989 | Connolly et al. | |
| 4,863,471 A | 9/1989 | Mansat | |
| 4,871,367 A | 10/1989 | Christensen et al. | |
| 4,873,967 A | 10/1989 | Sutherland | |
| 4,883,486 A | 11/1989 | Kapadia et al. | |
| 4,904,261 A | 2/1990 | Dove et al. | |
| 4,919,672 A | 4/1990 | Millar et al. | |
| 4,923,471 A | 5/1990 | Morgan | |
| 4,942,875 A | 7/1990 | Hlavacek et al. | |
| 4,955,915 A | 9/1990 | Swanson | |
| 4,959,065 A | 9/1990 | Arnett et al. | |
| 4,988,349 A | 1/1991 | Pennig | |
| 4,988,350 A * | 1/1991 | Herzberg | A61B 17/746 606/65 |
| 5,002,574 A | 3/1991 | May et al. | |
| 5,011,497 A | 4/1991 | Persson et al. | |
| 5,019,077 A | 5/1991 | DeBastiani et al. | |
| 5,019,104 A | 5/1991 | Whiteside et al. | |
| 5,026,372 A | 6/1991 | Sturtzkopf et al. | |
| 5,035,700 A | 7/1991 | Kenna | |
| 5,041,112 A | 8/1991 | Mingozzi et al. | |
| 5,100,403 A | 3/1992 | Hotchkiss et al. | |
| 5,103,811 A | 4/1992 | Crupi | |
| 5,121,742 A | 6/1992 | Engen | |
| 5,152,280 A | 10/1992 | Danieli | |
| 5,152,790 A | 10/1992 | Rosenberg et al. | |
| 5,197,966 A * | 3/1993 | Sommerkamp | A61B 17/8061 606/280 |
| 5,197,986 A | 3/1993 | Mikhail | |
| 5,231,977 A | 8/1993 | Graston | |
| 5,258,032 A | 11/1993 | Bertin | |
| 5,304,180 A | 4/1994 | Slocum | |
| 5,314,481 A | 5/1994 | Bianco | |
| 5,318,567 A | 6/1994 | Vichard | |
| 5,326,364 A | 6/1994 | Clift, Jr. et al. | |
| 5,352,190 A | 10/1994 | Fischer | |
| 5,375,823 A | 12/1994 | Navas | |
| 5,383,937 A | 1/1995 | Mikhail | |
| 5,405,347 A | 4/1995 | Lee et al. | |
| 5,415,661 A | 5/1995 | Holmes | |
| 5,425,775 A | 6/1995 | Kovacevic et al. | |
| 5,456,722 A | 10/1995 | McLeod et al. | |
| 5,480,443 A | 1/1996 | Elias | |
| 5,540,688 A | 7/1996 | Navas | |
| 5,545,229 A | 8/1996 | Parsons et al. | |
| 5,571,198 A | 11/1996 | Drucker et al. | |
| 5,575,819 A | 11/1996 | Amis | |
| 5,578,038 A | 11/1996 | Slocum | |
| 5,580,353 A | 12/1996 | Mendes et al. | |
| 5,601,553 A | 2/1997 | Trebling et al. | |
| 5,624,440 A | 4/1997 | Huebner | |
| 5,662,648 A | 9/1997 | Faccioli et al. | |
| 5,662,650 A | 9/1997 | Bailey et al. | |
| 5,676,667 A | 10/1997 | Hausman | |
| 5,681,313 A | 10/1997 | Diez | |
| 5,695,496 A | 12/1997 | Orsak et al. | |
| 5,702,460 A | 12/1997 | Carls et al. | |
| 5,702,465 A | 12/1997 | Burkinshaw | |
| 5,702,467 A | 12/1997 | Gabriel et al. | |
| 5,716,357 A | 2/1998 | Rogozinski | |
| 5,733,287 A | 3/1998 | Tepic et al. | |
| 5,749,872 A | 5/1998 | Kyle et al. | |
| 5,766,251 A | 6/1998 | Koshino | |
| 5,803,924 A | 9/1998 | Oni et al. | |
| 5,824,106 A | 10/1998 | Fournol | |
| 5,871,540 A | 2/1999 | Weissman et al. | |
| 5,873,843 A | 2/1999 | Draper | |
| 5,879,386 A | 3/1999 | Jore | |
| 5,888,203 A | 3/1999 | Goldberg | |
| 5,928,234 A | 7/1999 | Manspeizer | |
| 5,944,757 A * | 8/1999 | Grammont | A61F 2/40 128/898 |
| 5,976,125 A | 11/1999 | Graham | |
| 5,976,136 A | 11/1999 | Bailey et al. | |
| 5,989,292 A | 11/1999 | van Loon | |
| 6,036,691 A | 3/2000 | Richardson | |
| 6,096,040 A | 8/2000 | Esser | |
| 6,113,637 A | 9/2000 | Gill et al. | |
| 6,132,468 A | 10/2000 | Mansmann | |
| 6,139,550 A | 10/2000 | Michelson | |
| 6,143,032 A | 11/2000 | Schafer et al. | |
| 6,146,423 A | 11/2000 | Cohen et al. | |
| 6,161,080 A | 12/2000 | Aouni-Ateshian et al. | |
| 6,162,223 A | 12/2000 | Orsak et al. | |
| 6,176,860 B1 | 1/2001 | Howard | |
| 6,193,225 B1 | 2/2001 | Watanabe | |
| 6,200,347 B1 | 3/2001 | Anderson et al. | |
| D443,060 S * | 5/2001 | Benirschke | D24/155 |
| 6,245,110 B1 | 6/2001 | Grundei et al. | |

(56) References Cited

U.S. PATENT DOCUMENTS

| | | |
|---|---|---|
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde, Jr. |
| 6,599,322 B1 | 7/2003 | Amrich et al. |
| 6,616,696 B1 | 9/2003 | Merchant |
| 6,620,332 B2 | 9/2003 | Amrich |
| 6,623,486 B1 * | 9/2003 | Weaver ............ A61B 17/8057 606/281 |
| 6,626,945 B2 | 9/2003 | Simon et al. |
| 6,632,247 B2 | 10/2003 | Boyer, II et al. |
| 6,652,529 B2 | 11/2003 | Swanson |
| 6,663,631 B2 | 12/2003 | Kuntz |
| 6,679,914 B1 | 1/2004 | Gabbay |
| 6,692,497 B1 | 2/2004 | Tormala et al. |
| 6,692,498 B1 | 2/2004 | Niiranen et al. |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber |
| 6,752,831 B2 | 6/2004 | Sybert et al. |
| 6,770,078 B2 | 8/2004 | Bonutti |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,125 B2 | 2/2005 | Simon et al. |
| 6,852,330 B2 | 2/2005 | Bowman et al. |
| 6,854,330 B2 | 2/2005 | Potter |
| 6,855,150 B1 | 2/2005 | Linehan |
| 6,866,684 B2 | 3/2005 | Fell et al. |
| 6,884,242 B2 | 4/2005 | LeHuec et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,910 B2 | 11/2005 | Ritland |
| 6,966,928 B2 | 11/2005 | Fell et al. |
| 6,972,020 B1 | 12/2005 | Grayson et al. |
| 6,974,480 B2 | 12/2005 | Messerli et al. |
| 6,994,730 B2 | 2/2006 | Posner |
| 6,997,940 B2 | 2/2006 | Bonutti |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,018,418 B2 | 3/2006 | Amrich et al. |
| 7,025,790 B2 | 4/2006 | Parks et al. |
| 7,029,475 B2 | 4/2006 | Pajabi |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,128,744 B2 | 10/2006 | Weaver et al. |
| 7,141,073 B2 | 11/2006 | May et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,188,626 B2 | 3/2007 | Foley et al. |
| 7,201,728 B2 | 4/2007 | Sterling |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,291,169 B2 | 11/2007 | Hodorek |
| 7,297,161 B2 | 11/2007 | Fell |
| 7,306,605 B2 | 12/2007 | Ross |
| 7,322,983 B2 | 1/2008 | Harris |
| 7,322,984 B2 | 1/2008 | Doubler et al. |
| 7,323,012 B1 | 1/2008 | Stone et al. |
| 7,341,589 B2 | 3/2008 | Weaver et al. |
| 7,341,590 B2 | 3/2008 | Ferree |
| 7,341,602 B2 | 3/2008 | Fell et al. |
| 7,361,196 B2 | 4/2008 | Fallin et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish, Jr. et al. |
| 7,534,270 B2 | 5/2009 | Ball |
| 7,544,210 B2 | 6/2009 | Schaefer et al. |
| 7,553,331 B2 | 6/2009 | Manspeizer |
| 7,572,291 B2 | 8/2009 | Gil et al. |
| 7,611,540 B2 | 11/2009 | Clifford et al. |
| 7,618,454 B2 | 11/2009 | Bentley et al. |
| 7,632,310 B2 | 12/2009 | Clifford et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,655,029 B2 * | 2/2010 | Niederberger ..... A61B 17/8057 606/280 |
| 7,655,041 B2 | 2/2010 | Clifford et al. |
| 7,678,147 B2 | 3/2010 | Clifford et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,744,638 B2 * | 6/2010 | Orbay ................ A61B 17/8047 606/280 |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,819,918 B2 | 10/2010 | Malaviya et al. |
| 7,828,852 B2 | 11/2010 | Bonutti |
| 7,846,211 B2 | 12/2010 | Clifford et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,951,176 B2 * | 5/2011 | Grady, Jr. ............ A61B 17/746 606/280 |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |

(56) References Cited

U.S. PATENT DOCUMENTS

| | | |
|---|---|---|
| 8,052,753 B2 | 11/2011 | Melvin |
| 8,052,755 B2 | 11/2011 | Naidu |
| 8,083,746 B2 | 12/2011 | Novak |
| 8,088,166 B2 | 1/2012 | Makower et al. |
| 8,088,168 B2 | 1/2012 | Hassler et al. |
| 8,092,530 B2 | 1/2012 | Strzepa et al. |
| 8,092,544 B2 | 1/2012 | Wright et al. |
| 8,100,967 B2 | 1/2012 | Makower et al. |
| 8,114,156 B2 | 2/2012 | Hatch |
| 8,123,805 B2 | 2/2012 | Makower et al. |
| 8,128,697 B2 | 3/2012 | Fell et al. |
| 8,128,704 B2 | 3/2012 | Brown et al. |
| 8,142,503 B2 | 3/2012 | Malone |
| 8,257,444 B2 | 9/2012 | Linares |
| 8,262,707 B2 * | 9/2012 | Huebner ............ A61B 17/8061 606/280 |
| 8,267,972 B1 * | 9/2012 | Gehlert ............. A61B 17/8014 606/280 |
| 8,282,681 B2 * | 10/2012 | McLeod ............. A61F 2/4405 623/17.11 |
| 8,292,955 B2 * | 10/2012 | Robinson ............. A61F 2/4606 623/14.12 |
| 8,328,805 B2 | 12/2012 | Cole |
| 8,372,078 B2 | 2/2013 | Collazo |
| 8,382,807 B2 | 2/2013 | Austin et al. |
| 8,523,921 B2 * | 9/2013 | Horan ............... A61B 17/8061 606/281 |
| 8,523,948 B2 * | 9/2013 | Slone ..................... A61B 17/56 623/13.11 |
| 8,597,362 B2 * | 12/2013 | Shenoy ............... A61B 17/56 623/20.21 |
| 8,771,363 B2 * | 7/2014 | Grotz ............... A61B 17/0642 623/18.11 |
| 8,845,724 B2 * | 9/2014 | Shenoy ............... A61B 17/56 623/13.12 |
| 8,986,311 B2 * | 3/2015 | Boudreault .......... A61B 17/025 606/192 |
| 9,114,016 B2 * | 8/2015 | Shenoy ............... A61B 17/56 |
| 9,216,091 B2 * | 12/2015 | Hardy .................. A61F 2/4081 |
| 9,278,004 B2 * | 3/2016 | Shenoy ............... A61B 17/56 |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 * | 1/2002 | Winquist ............ A61B 17/8061 606/283 |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp |
| 2002/0095154 A1 | 7/2002 | Atkinson et al. |
| 2002/0107574 A1 | 8/2002 | Boehm, Jr. et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Leman |
| 2004/0267375 A1 * | 12/2004 | Friedrichs ............ A61F 2/30721 623/22.18 |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde, Jr. |
| 2005/0261680 A1 | 11/2005 | Draper |
| 2005/0261767 A1 | 11/2005 | Anderson et al. |
| 2005/0267584 A1 | 12/2005 | Burdulis, Jr. et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074492 A1 | 4/2006 | Frey |
| 2006/0085069 A1 | 4/2006 | Kim |
| 2006/0100715 A1 | 5/2006 | De Villiers |
| 2006/0106460 A1 | 5/2006 | Messerli et al. |
| 2006/0122620 A1 | 6/2006 | Kim |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0074423 A1 | 8/2006 | Alleyne |
| 2006/0178744 A1 | 8/2006 | de Villiers et al. |
| 2006/0235387 A1 | 10/2006 | Peterman |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0173946 A1 | 6/2007 | Bonutti |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0276491 A1 * | 11/2007 | Ahrens .................. A61F 2/441 623/17.11 |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 * | 1/2008 | Castaneda .......... A61B 17/1728 606/86 A |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1 | 2/2008 | Lee et al. |

(56) References Cited

U.S. PATENT DOCUMENTS

| | | |
|---|---|---|
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Millet et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0208346 A1* | 8/2008 | Schwartz ............ A61B 17/562 623/17.17 |
| 2008/0234686 A1 | 9/2008 | Beaurain et al. |
| 2008/0262549 A1 | 10/2008 | Bennett et al. |
| 2008/0262618 A1 | 10/2008 | Hermsen et al. |
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1* | 11/2008 | Clifford ............... A61B 17/68 623/20.14 |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1* | 11/2008 | Clifford ............... A61B 17/68 623/20.21 |
| 2008/0275563 A1 | 11/2008 | Makower et al. |
| 2008/0275564 A1 | 11/2008 | Makower et al. |
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris |
| 2009/0076605 A1* | 3/2009 | Linares .............. A61F 2/32 623/14.12 |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0132047 A1* | 5/2009 | Mansmann ........... A61F 2/0811 623/14.12 |
| 2009/0164014 A1 | 6/2009 | Liljensten et al. |
| 2009/0182433 A1 | 7/2009 | Reiley et al. |
| 2009/0187252 A1* | 7/2009 | Howald ............... A61F 2/4603 623/22.15 |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1* | 12/2009 | Gabriel ............... A61B 17/68 606/283 |
| 2010/0023126 A1* | 1/2010 | Grotz ............... A61F 2/30756 623/14.12 |
| 2010/0023127 A1* | 1/2010 | Shohat ............... A61B 17/562 623/14.12 |
| 2010/0049322 A1 | 2/2010 | McKay |
| 2010/0049325 A1 | 2/2010 | Biedermann et al. |
| 2010/0057216 A1* | 3/2010 | Gannoe ............... A61F 2/4202 623/21.18 |
| 2010/0076564 A1 | 3/2010 | Schilling et al. |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Gittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1 | 5/2010 | Halbrecht |
| 2010/0137996 A1* | 6/2010 | Clifford ............... A61B 17/68 623/23.41 |
| 2010/0145449 A1 | 6/2010 | Makower et al. |
| 2010/0161057 A1 | 6/2010 | Berry et al. |
| 2010/0168857 A1 | 7/2010 | Hatch |
| 2010/0198354 A1* | 8/2010 | Halbrecht ............ A61B 17/58 623/20.19 |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0178603 A1* | 7/2011 | Long .................. A61F 2/40 623/19.13 |
| 2011/0202138 A1 | 8/2011 | Shenoy et al. |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0238180 A1 | 9/2011 | Fritz et al. |
| 2011/0245928 A1* | 10/2011 | Landry ............... A61B 17/56 623/20.28 |
| 2011/0264216 A1* | 10/2011 | Makower ............ A61B 17/68 623/13.12 |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1 | 8/2012 | Horan et al. |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0018479 A1* | 1/2013 | Grotz ............... A61F 2/30756 623/22.14 |
| 2013/0041416 A1 | 2/2013 | Regala et al. |
| 2013/0096629 A1 | 4/2013 | Rollinghoff et al. |
| 2013/0150977 A1* | 6/2013 | Gabriel ............... A61F 2/3859 623/20.32 |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1* | 8/2013 | Shenoy ............... A61B 17/56 623/13.12 |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |

(56) References Cited

U.S. PATENT DOCUMENTS

| | | | | |
|---|---|---|---|---|
| 2014/0128974 | A1* | 5/2014 | Bromer | A61F 2/30 623/14.12 |
| 2014/0156004 | A1* | 6/2014 | Shenoy | A61B 17/56 623/13.12 |
| 2014/0156005 | A1* | 6/2014 | Shenoy | A61B 17/56 623/13.12 |
| 2014/0257292 | A1* | 9/2014 | Embleton | A61B 17/8061 606/71 |
| 2014/0343675 | A1* | 11/2014 | Vanleeuwen | A61F 2/30756 623/14.12 |
| 2014/0371864 | A1* | 12/2014 | Shohat | A61B 17/562 623/19.11 |
| 2016/0213402 | A1* | 7/2016 | Shenoy | A61B 17/56 |
| 2016/0256286 | A1* | 9/2016 | Morris | A61B 17/56 |
| 2017/0027708 | A1* | 2/2017 | Shenoy | A61F 2/4003 |

FOREIGN PATENT DOCUMENTS

| | | |
|---|---|---|
| DE | 19855254 A1 | 6/2000 |
| EP | D383419 A1 | 8/1990 |
| EP | D953317 A1 | 4/1999 |
| EP | 1410769 A2 | 4/2004 |
| EP | 1770302 A1 | 4/2007 |
| EP | 1429675 | 10/2007 |
| EP | 1682020 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| NZ | 533300 | 2/2005 |
| RU | 2085148 | 7/1997 |
| RU | 2217105 C2 | 11/2003 |
| RU | 2241400 C2 | 12/2004 |
| SU | 578063 A1 | 10/1977 |
| SU | 678957 A1 | 11/1977 |
| SU | 624613 A1 | 9/1978 |
| SU | 640740 A1 | 1/1979 |
| SU | 104605 A1 | 12/1979 |
| SU | 119612 A1 | 3/1980 |
| SU | 141872 A1 | 6/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| SU | 1769868 A1 | 10/1992 |
| WO | 91/07137 | 5/1991 |
| WO | 94/06364 A1 | 3/1994 |
| WO | 96/19944 A1 | 7/1996 |
| WO | 2004019831 A2 | 3/2004 |
| WO | 2004024037 A2 | 3/2004 |
| WO | 2006045091 A2 | 4/2006 |
| WO | 2006049993 | 5/2006 |
| WO | 2006110578 A3 | 10/2006 |
| WO | 2007056645 A2 | 5/2007 |
| WO | 2007090009 A1 | 8/2007 |
| WO | 2007090015 A1 | 8/2007 |
| WO | 2007090017 A1 | 8/2007 |
| WO | 2007106962 A1 | 9/2007 |
| WO | 2007109132 A2 | 9/2007 |
| WO | 2007109140 A2 | 9/2007 |
| WO | 2007109417 A2 | 9/2007 |
| WO | 2007109436 A2 | 9/2007 |
| WO | 2007114769 A1 | 10/2007 |
| WO | 2007117571 A2 | 10/2007 |
| WO | 2008006098 A2 | 1/2008 |
| WO | 2009/018365 A1 | 2/2009 |
| WO | 2011025959 A1 | 3/2011 |
| WO | 2012/062908 A1 | 5/2012 |

OTHER PUBLICATIONS

Office Action dated May 17, 2012, in connection with related U.S. Appl. No. 13/002,829, filed Jan. 6, 2011, Shenoy.
Office Action dated Jul. 24, 2012, in connection with related U.S. Appl. No. 12/870,462, filed Aug. 27, 2010, Shenoy.
Final (Rejection) Office Action dated Mar. 18, 2013, in connection with related U.S. Appl. No. 12/870,462, filed Aug. 27, 2010.
Final (Rejection) Office Action dated Jan. 31, 2013, in connection with related U.S. Appl. No. 13/002,829, filed Jan. 6, 2011.
Office Action dated May 18, 2016, in connection with U.S. Appl. No. 14/644,792, filed Mar. 11, 2015, Shenoy.
Office Action dated May 5, 2016, in connection with U.S. Appl. No. 14/542,121, filed Mar. 9, 2015, Shenoy.
Lafaver, et al., "Tibial Tuberosity Advancement for Stabilization of the Canine Cranial Cruciate Ligament-Deficient Stifle Joint: Surgical Technique, Early Results, and Complications in 101 Dogs", Veterinary Surgery, 36:573-586, 2007.
Synthes, Inc., LCP Proximal Tibial Plate 3.5; Technique Guide; pp. 1-20; Jun. 2011.
Tew, M et al.; Anteriorization of the quadriceps tendon. A biomechanical study on a new technique for unloading the patellofemoral joint. University of Tennessee College of Medicine; Poster No. 0848 • ORS 2012 Annual Meeting.
Notice of Allowance dated Aug. 4, 2014 in connection with related U.S. Appl. No. 14/175,829, filed Feb. 7, 2014, Vivek Shenoy.
Non-Final Rejection Office Action dated Aug. 27, 2014 in connection with related U.S. Appl. No. 14/175,813, filed Feb. 7, 2014, Vivek Shenoy.
European Search Report dated Aug. 7, 2014, issued in connection with related EP14164658.
Extended Search Report dated Aug. 26, 2014, issued in connection with related EP14164658.
Final Office Action dated Feb. 26, 2015, in connection with related U.S. Appl. No. 13/002,829, filed Jan. 6, 2011.
Response to Non-Final Office Action dated May 26, 2015, in connection with related U.S. Appl. No. 13/002,829, filed Jan. 6, 2011.
Partial International Search dated May 11, 2015, in connection with related PCT/US2015/019938, filed Mar. 11, 2015.
International Search Report and Written Opinion dated Jul. 3, 2015, in connection with related PCT/US2015/019938, filed Mar. 11, 2015.
Office Action dated Jul. 1, 2015, in connection with related U.S. Appl. No. 13/974,930, filed Aug. 23, 2013.
Restriction Requirement dated Jul. 23, 2015, in connection with related U.S. Appl. No. 14/642,121, filed Mar. 9, 2015.
Restriction Requirement dated Jul. 22, 2015, in connection with related U.S. Appl. No. 14/644,792, filed Mar. 11, 2015.
Miller, R.K., Goodfellow, J.W., Murray, D.W. And O'Connor, J.J., In vitro measurement of patellofemoral force after three types of knee replacement; The Journal of Bone & Joint Surgery (Br), vol. 80-B, No. 5, Sep. 1998; pp. 900-906.
Office Action dated Dec. 19, 2014, in connection with related U.S. Appl. No. 13/843,128, filed Mar. 15, 2013.
Response to Restriction Requirement dated Oct. 27, 2014, issued in connection with related U.S. Appl. No. 13/843,128, filed Mar. 15, 2013.
Restriction Requirement dated Aug. 25, 2014, issued in connection with related U.S. Appl. No. 13/843,128, filed Mar. 15, 2013.
Response to Non-Final Office Action dated Apr. 20, 2015, in connection with related U.S. Appl. No. 13/843,128.

(56) References Cited

OTHER PUBLICATIONS

Final Office Action dated Jun. 10, 2015, in connection with related U.S. Appl. No. 13/843,128, filed Mar. 15, 2013.
Chow, S.P. et al., "Fracture of the Tibial Tubercle in the Adolescent" British Editorial Society of Bone and Joint Surgery, vol. 72-B, No. 2, Mar. 1990.
Non-Final Office Action dated Sep. 25, 2015, in connection with related U.S. Appl. No. 14/644,792, filed Mar. 11, 2015.
Final Office Action dated Sep. 15, 2015, in connection with related U.S. Appl. No. 13/002,829, filed Jan. 6, 2011.
Supplemental Response to Final Office Action dated Sep. 3, 2015, in connection with related Application No. 13/843,128, filed Mar. 15, 2013.
Response to Final Office Action dated Aug. 10, 2015, in connection with related U.S. Appl. No. 13/843,128, filed Mar. 15, 2013.
Amendment and Response to Election/Restriction Requirement dated Sep. 11, 2015, in connection with related U.S. Appl. No. 14/644,792, filed Mar. 11, 2015.
Response to Election/Restriction dated Sep. 23, 2015, in connection with related U.S. Appl. No. 14/642,121, filed Mar. 9, 2015.
Response to First Non-Final Office Action dated Nov. 2, 2015, in connection with U.S. Appl. No. 13/974,930, filed Aug. 23, 2013.
Non-Final Office Action dated Oct. 7, 2015, in connection with U.S. Appl. No. 14/642,121, filed Mar. 9, 2015.
Response to Final Office Action dated Apr. 26, 2016, in connection with U.S. Appl. No. 13/974,930, filed Mar. 23, 2013.
Notice of Allowance dated Feb. 3, 2015, in connection with related U.S. Appl. No. 14/175,813, filed Feb. 7, 2014.
Appellant's Brief dated Mar. 15, 2016, in connection with related U.S. Appl. No. 13/002,829, filed Jan. 3, 2011.
Office Action dated Oct. 6, 2016, in connection with U.S. Appl. No. 13/002,829, filed Jan. 6, 2011.
Arnoczky et al., Biomechanical Analysis of Forces Acting About the Canine Hip, American Journal Veterinary Research, vol. 42, Issue: 9, Sep. 1981, pp. 1581-1585.
Becker et al., Surgical Treatment of Isolated Patellofemoral Osteoarthritis, Clinical Orthopaedics and Related Research vol. 466, No. 2, Feb. 2008, pp. 443-449.
Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.
Clifford et al., The KineSpring load absorber implant: Rationale, Design and Biomechanical Characterization, Journal of Medical Engineering & Technology, vol. 35, No. 1, Jan. 2011, pp. 65-71.
Delp et al., An Interactive Graphics-Based Model of the Lower Extremity to Study Orthopaedic Surgical Procedures, IEEE Transactions on Biomedical Engineering, vol. 37, No. 8, Aug. 1990, pp. 757-767.
Delp et al., Biomechanical Analysis of the Chiari Pelvic Osteotomy Preserving Hip Abductor Strength, Reprinted from Clinical Orthopaedics, vol. 25, May 1990, pp. 189-198.
Free et al, Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.
Jack Farr, M.D., Tibial Tubercle Osteotomy, Techniques in Knee Surgery, vol. 2, Issue 1, 2003, pp. 28-42.
Goetz et al., Hip Joint Contact Force in the Emu (Dromaius novaehollandiae) during Normal Level Walking, Journal of Biomechanics, 41(4), 2008, pp. 770-778.
Jacobsen et al., Hip dysplasia: a significant risk factor for the development of hip osteoarthritis. A cross-sectional survey, Rheumatology vol. 44 No. 2, 2005, pp. 211-218.
Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.
Kirkley et al., The Effect of Bracing on Varus Gonarthrosis, The Journal of Bone and Joint Surgery, vol. 81-A, No. 4, Apr. 1999, pp. 539-548.
Lafeber et al., Unloading Joints to Treat Osteoarthritis, including Joint Distraction, Current Opinion in Rheumatology 2006, 18, pp. 519-525.
Lloyd et al., An EMG-driven Musculoskeletal Model to Estimate Muscle Forces and Knee Joint Moments in Vivo, Journal of Biomechanics 36, 2003, pp. 765-776.
Lloyd et al., Strategies of Muscular Support of Varus Andvalgus Isometric Loads at the Human Knee, Journal of Biomechanics 34, 2001, pp. 1257-1267.
Maquet, P, Biomechanics of Hip Dysplasia, Acta Ortopaedica Belgica, vol. 65-3, 1999, pp. 302-314.
McWilliams et al., Mild Acetabular Dysplasia and Risk of Osteoarthritis of the hip: a case-control study, Annals of the Rheumatic Diseases, 2010; 69, pp. 1774-1778.
Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.
Pedersen et al., A Model to Predict Canine Pelvic Limb Musuloskeletal Geometry, Acta Anat 1991; 140, pp. 139-145.
Pollo et al., Knee Bracing for Unicompartmental Osteoarthritis, Journal of the American Academy of Orthopaedic Surgeons, vol. 14, No. 1, Jan. 2006, pp. 5-11.
Pollo et al., Reduction of Medial Compartment Loads with Valgus Bracing of the Osteoarthritic Knee, The American Journal of Sports Medicine, vol. 30, No. 3, 2002, pp. 414-421.
Saleh et al., Operative Treatment of Patellofemoral Arthritis, The Journal of Bone & Joint Surgery, vol. 87-A, No. 3, Mar. 2005, pp. 659-671.
Sharma et al., The Role of Knee Alignment in Disease Progression and Functional Decline in Knee Osteoarthritis, JAMA, vol. 286, No. 2, Jul. 11, 2001, pp. 188-195.
Sims et al., Investigation of Hip Abductor Activation in Subjects with Clinical Unilateral Hip Osteoarthritis, Annals of the Rheumatic Diseases, 2002; 61: pp. 687-692.
Thorp et al., The biomechanical effects of focused muscle training on medial knee loads in OA of the knee: a pilot, proof of concept study, Journal of Musculoskeletal and Neuronal Interactions, 10(2): 2010, pp. 166-173.
Wenger et al., Early Surgical Correction of Residual Hip Dysplasia: The San Diego Children's Hospital Approach, Acta Orthopaedica Belgica, vol. 65, 1999, pp. 277-287.
Winby et al., Muscle and External Load Contribution to Knee Joint Contact Loads during Normal Gait, Journal of Biomechanics 42, 2009, pp. 2294-2300.
Response to Final Office Action dated Apr. 1, 2013, in connection with related U.S. Appl. No. 13/002,829, filed Aug. 27, 2009.
Response to First Non-Final Office Action dated Jan. 25, 2016, in connection with related U.S. Appl. No. 14/642,121, filed Mar. 9, 2015.
Office Action dated Feb. 26, 2016, in connection with related U.S. Appl. No. 13/974,930, filed Aug. 23, 2013.
Gumpel et al., An Objective Assessment of Synovitis of the Knee: Measurement of the Size of the Suprapatellar Pouch on Xeroradiography. Annals of the Rheumatic Diseases. 1980, (39): 359-366.
Miller, R.K, Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.
Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, pp. 129.
Anatomic Locked Plating System Brochure, BIOMET® Orthopedics, Form BMET0002.0, REV 053112, pp. 1-16, Copyright 2012.

(56) References Cited

OTHER PUBLICATIONS

SPS Periarticular Plates Brochure, STRYKER® Trauma AG, Literature No. 982274, Lot B46404, pp. 1-8; Copyright 2004.
Zimmer® Periarticular Distal Femoral Locking Plate Surgical Technique, the Science of the Landscape, Zimmer, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9; Dec. 3, 2008.
LCP Locking Compression Plate—Ordering Information; SYNTHES®, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final Office Action dated Mar. 18, 2013, in connection with related U.S. Appl. No. 12/870,462, filed Aug. 27, 2010.
Final Office Action dated Jan. 31, 2013, in connection with related U.S. Appl. No. 13/002,829, filed Jan. 6, 2011.
Amendment and Response to Final Office Action dated May 20, 2013, in connection with related U.S. Appl. No. 12/870,462, filed Aug. 27, 2010.
Advisory Action dated Apr. 23, 2013 in connection with related U.S. Appl. No. 13/002,829, filed Jan. 6, 2011.
Advisory Action dated Jun. 20, 2013 in connection with related U.S. Appl. No. 13/002,829, filed Jan. 6, 2011.
PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.
Bruce et al., Patellar Contact Pressure Changes with Anteromedialization of Tibial Tubercle, Lateral Release, and New Technique for Elevating Quadriceps Tendon: A Biomechanical Study,: Journal of Surgical Orthopaedic Advances 22(4), pp. 270-276, 2013.
Non-Final Office Action dated Apr. 11, 2014, in connection with related U.S. Appl. No. 14/175,829, filed Feb. 2, 2014, Vivek Shenoy.
Response to First Non-Final Office Action dated May 5, 2014, in connection with related U.S. Appl. No. 14/175,829, filed Feb. 7, 2014, Vivek Shenoy.
Response to Election/Restriction dated Jul. 1, 2014 in connection with related U.S. Appl. No. 14/175,813, filed Feb. 7, 2014.
Office Action dated Jul. 9, 2012, in connection with related European Application No. 10812664, entitled Method and Apparatus for Force Redistributon in Articular Joints, filed Aug. 27, 2010, Cotera, Inc.
Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.
Maquet, Paul G.J., Biomechanics of the Knee With Application to the Pathogenesis and the Surgical Treatment of Osteoarthritis; Springer-Verlag Berlin Heidelberg New York, 1976, pp. 134-204.
Sridhar et al., Obesity and symptomatic osteoarthritis of the knee, The Journal of Bone & Joint Surgery, Instructional Review, vol. 94-B, No. 4, Apr. 2012, pp. 433-441.
Lasmar, et al., Importance of the Different Posterolateral Knee Static Stabilizers: Biomechanical Study; Clinics 2010; 65(4) pp. 433-440.
Hunter, David et al., Alignment and Osteoarthritis of the Knee, Journal of Bone and Joint Surgery, 2009: 91 Suppl. 1:85-9, pp. 85-89.
Halbrecht, Jeffrey L., Arthroscopic Patella Realignment: An All-Inside Technique, Arthroscopy: The Journal of Arthroscopic and Related Surgery, vol. 17, No. 9 (Nov.-Dec.) 2001; pp. 940-945.
Arnold, Allison S., et al., Do the hamstrings operate at increased muscle-tendon lengths and velocities after surgical lengthening? Journal of Biomechanics, Mar. 2005; pp. 1-9.

Unnanuntana, Aasis et al., Management of chronic lateral instability due to lateral collateral ligament deficiency after total knee arthroplasty: a case report; Journal of Medical Case Reports, 2010, 4:144; pp. 1-5.
Maquet, P., Biomechanical Aspects of the Relationship between Femur and Patella, Z. Orthop. 112 (1974); pp. 520-623.
Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.
Maquet P., Reduction of the articular pressure of the hip by surgical lateralization of the greater trochanter, PMID: 1015273, Clin Orthop Relat Res. 1977, Mar.-Apr.; (123): 138 (Abstract only).
Maquet P., Importance of the position of the greater trochanter, PMID: 2382566, Acta Orthop Belg. 1990; 56 (1 Pt. B): 307 (Abstract only).
Maquet, Paul, "Advancement of the Tibial Tubersosity," Clinical Orthopaedics and Related Research, No. 15, 1976, pp, 225-230.
Townsend et al., "The Biomechanics of the Human Patella and its Implications for Chodromalacia," Journal of Biomechanics, 1977, vol. 10, pp. 403-407.
Supplementary European Search Report dated May 23, 2012 for related application EP10812664 filed Aug. 27, 2010, entitled "Method and Apparatus for Force Redistribution in Articular," Cotera, Inc.
Lapinskaya, Valentina Spiridonovna, "Treatment of Diseases and Injuries of Hip Joint Using a Method of Distraction", Kuibyshev Medical Institute, 1990.
Larionov D. Yu, et al., "Medical Devices," Scientific and Technical Bimonthly Journal, May-Jun. 2008.
Lapinskaya, V.S., et al., "An Endoapparatus for Restoration of the Hip Joint," Writers Collective, 2008, UDK 615.472.03:616.728.2-089.28; pp. 8-12.
Lentsner, A.A., et al., "Device for Functional Relief of Hip Joint in Cotyloid Cavity Fracture Cases", Ortop Travmatol Protez. Apr. 1990 (4) 44-6.
Andriacchi, Thomas P., Ph.D. et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.
Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extra-cortical plates with reference to their surface properties and gemoetric designs", Elsevier, Biomaterials 20 (1999) pp. 793-800.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 Aug. 2007: pp. 833-838.
Dienst, M. et al.; "Dynamic External Fixation for Distal Radius Fractures"; Clinical Orthopaedics and Related Research, 1997, vol. 338, pp. 160-171.
Gunther, Klaus-Peter, M.D.; "Surgical Approaches for Osteoarthritis"; Best Practice & Research Clinical Rheumatology, vol. 15, No. 4, 2001, pp. 627-643.
Hall, J. et al.; "Use of a Hinged External Fixator for Elbow instability after Severe Distal Humeral Fracture"; Journal of Orthopaedic Trauma, 2000, vol. 14, No. 6, pp. 442-448.
Klein, D. et al.; "Percutaneous Treatment of Carpal, Metacarpal, and Phalangeal Injuries"; Clinical Orthopaedics and Related Research, 2000, vol. 375, pp. 116-125.
Krakauer J. et al.; "Hinged Device for Fractures involving the Proximal Interphalangeal Joint"; Clinical Orthopaedics and Related Research, 1996, vol. 327, pp. 29-37.
Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 (May-Jun.), 2001: pp. 510-516.

(56) References Cited

OTHER PUBLICATIONS

Madey, S. et al.; "Hinged External Fixation of the elbow: optimal axis alignment to minimize motion resistance"; Journal of Orthopaedic Trauma, 2000, vol. 14, No. 1, pp. 41-47.

Neel, Michael D., M.D. et al.; "Early Multicenter Experience With a Noninvasive Expandable Prosthesis"; Clinical Orthopaedics and Related Research, 2003, No. 415, pp. 72-81.

Neel, Michael D., M.D.; "Repiphysis—Limb Salvage System for the Skeletally Immature"; Wright Medical Technology, Reipiphysis Limb Salvage System, 2004, pp. 1-8.

Nockels, Russ P.; "Dynamic Stabilization in the Surgical Management of Painful Lumbar Spinal Disorders"; Spine, 2005, vol. 30, No. 16S, pp. S68-S72.

ORTHOFIX; "Xcaliber Articulated Ankle"; advertising brochure, May 2004.

ORTHOFIX; "Gentle Limb Deformity Correction"; website pages, http://www.eight-plate.com/, 2008.

Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.

Pilliar et al., "Bone Ingrowth and Stress Shielding with a Porous Surface Coated Fracture Fixation Plate," Journal of Biomedical Materials Research, vol. 13, (1979), pp. 799-810.

Repicci, John A., M.D. et al. "Minimally Invasive Unicondylar Knee Arthroplasty for the Treatment of Unicompartmental Osteoarthritis: an outpatient arthritic bypass procedure"; Orthopedic Clinics of North America, 35 (2004), pp. 201-216.

Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.

Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.

Tencer, Allan F. et al. "Fixation of the Patella (Chap. 9.3)"; in: Biomechanics in Orthopedic Trauma Bone Fracture and Fixation, 1994.

Thakur, A.J.; "Tension Band Wiring"; in; The Elements of Fracture Fixation, 1997, pp. 126-146.

Uchikura, C. et al.; "Comparative Study of Nonbridging and Bridging External Fixators from Unstable Distal Radius Fractures"; Journal of Orthopaedic Science, 2004, vol. 9, No. 6, pp. 560-565.

Van Der Esch, M. et al.; "Structural Joint Changes, Malalignment, and Laxity in Osteoarthritis of the knee"; Scand J Rheumatol 2005; 34: pp. 298-301.

Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.

Wilke, Hans-Joachim et al.; "Biomechanical Evaluation of a New Total Posterior-Element Replacement System"; Spine, 2006, vol. 31, No. 24, pp. 2790-2796.

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

\* cited by examiner

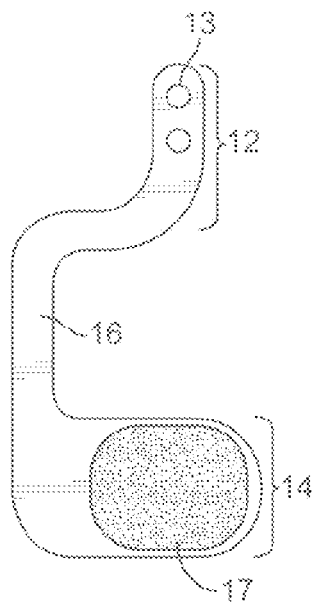
FIG. 4
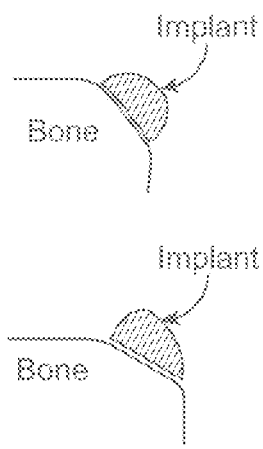
FIG. 5A
FIG. 5C
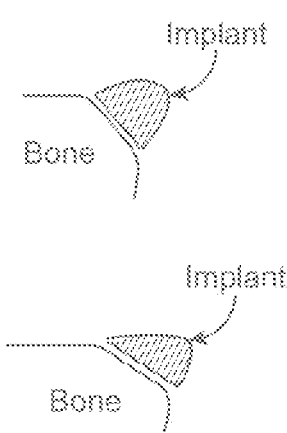
FIG. 5B
FIG. 5D
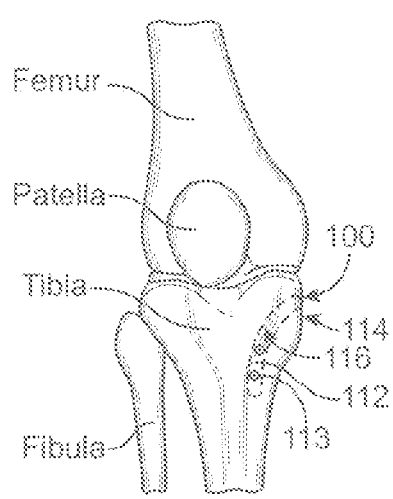
FIG. 6
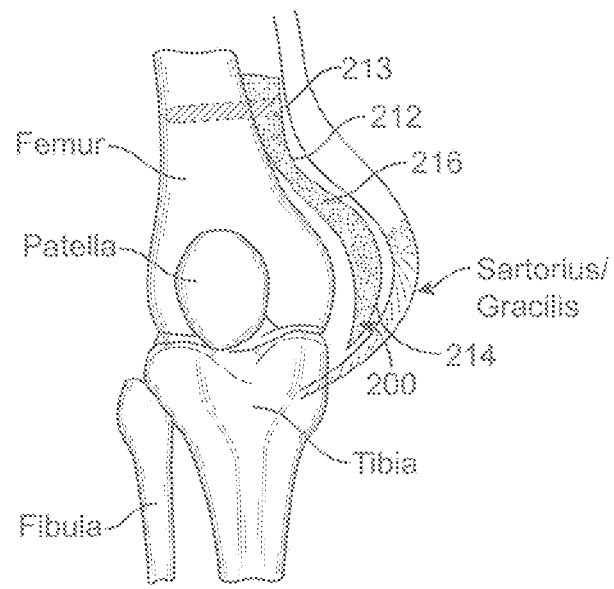
FIG. 7

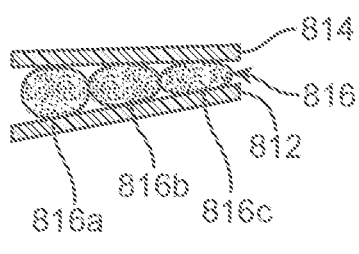 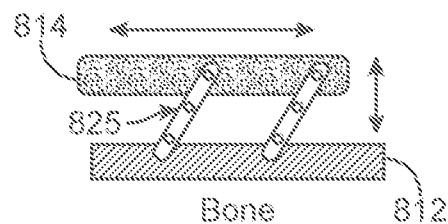
FIG. 21   FIG. 22
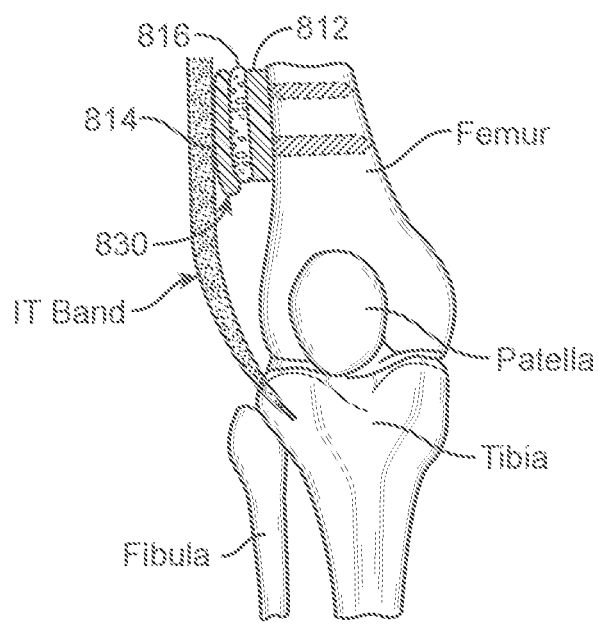 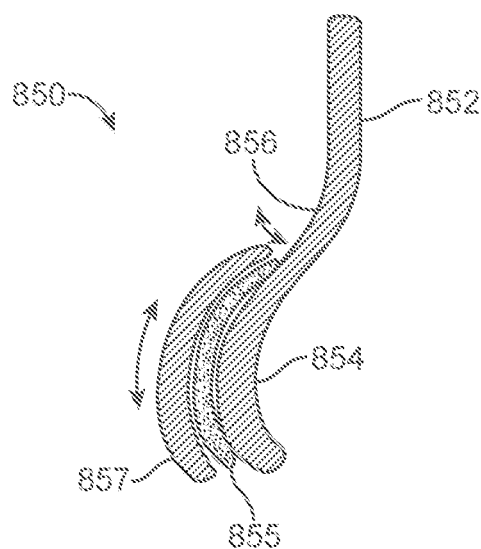
FIG. 23   FIG. 24

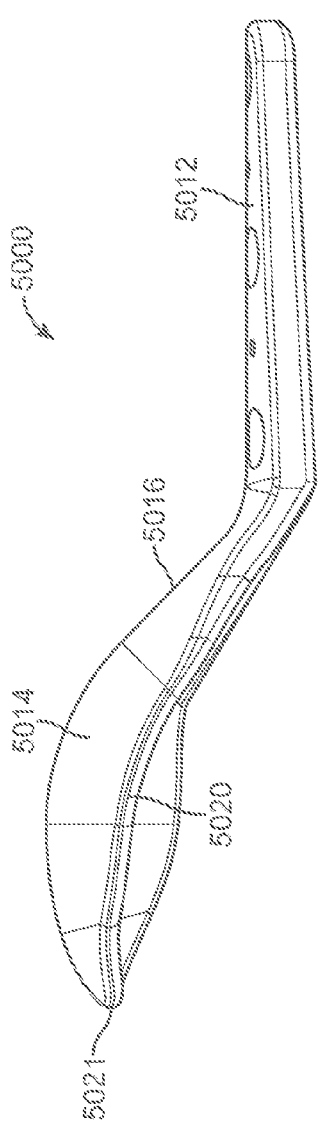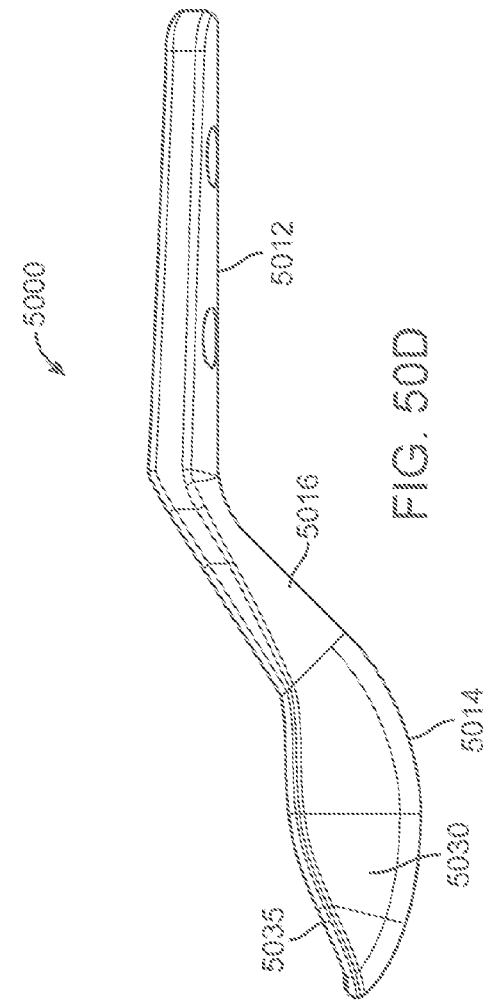

SECTION A-A

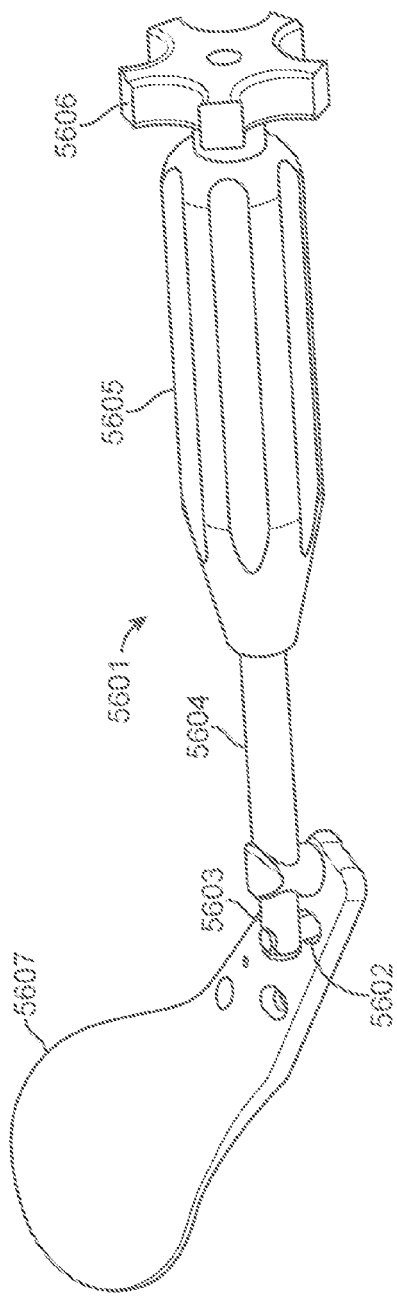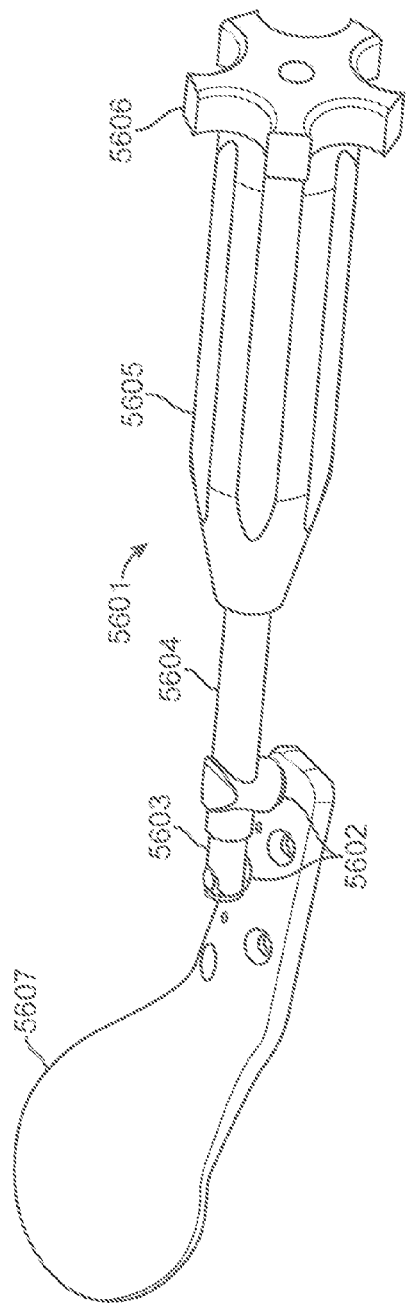

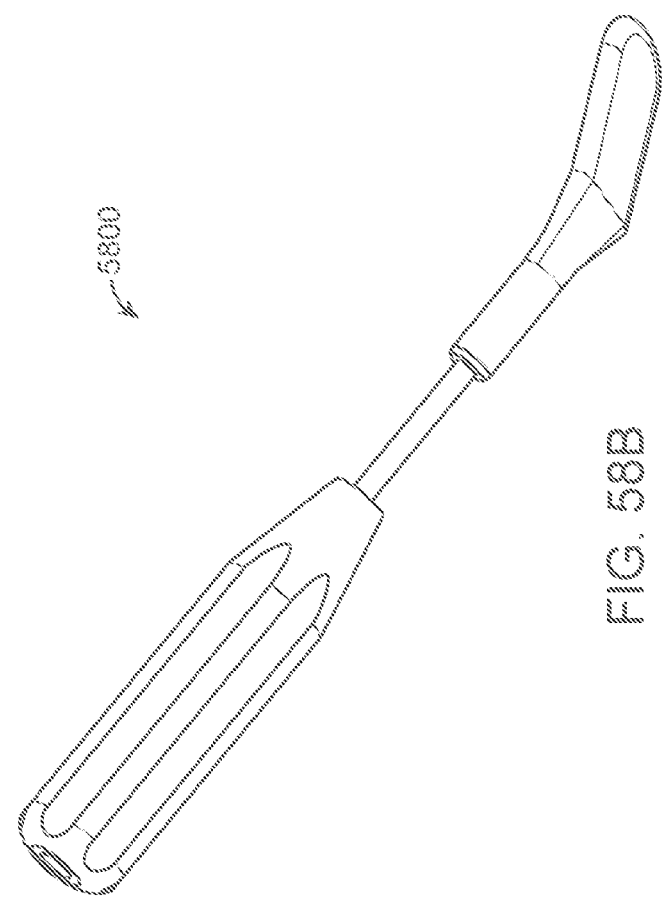
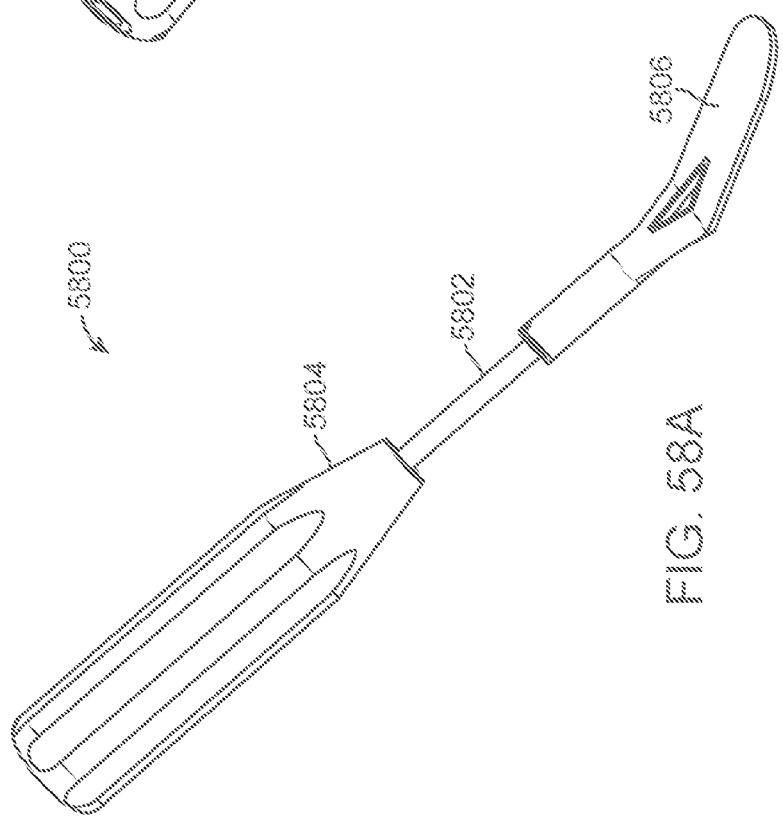

METHOD AND APPARATUS FOR ALTERING BIOMECHANICS OF ARTICULAR JOINTS

RELATED APPLICATIONS

This application is a continuation application of U.S. Nonprovisional patent application Ser. No. 13/843,128, filed on Mar. 15, 2013; which application was a nonprovisional of and claims priority to U.S. Provisional Patent Application Ser. No. 61/620,756 filed on Apr. 5, 2012 and U.S. Provisional Patent Application Ser. No. 61/695,406 filed on Aug. 31, 2012; U.S. Nonprovisional patent application Ser. No. 13/843,128 was also a Continuation-in-Part of U.S. Nonprovisional patent application Ser. No. 12/870,462, filed on Aug. 27, 2010 (now U.S. Pat. No. 8,597,362), which claims priority to U.S. Provisional Patent Application Ser. No. 61/237,518, filed Aug. 27, 2009, and U.S. Provisional Patent Application Ser. No. 61/288,692, filed Dec. 21, 2009. Each of these applications is incorporated herein by reference in its entirety. This application is also related to U.S. Nonprovisional patent application Ser. No. 13/002,829 filed on Aug. 27, 2010.

FIELD OF THE INVENTION

The present invention generally relates to the field of orthopedics. In particular, the present invention is directed to an interventional technique and an implant for altering biomechanics within articular joints to provide a therapeutic effect. More particularly, embodiments of the present invention are directed to alleviating joint pain and effects of osteoarthritis in the knee.

BACKGROUND

The human body contains many joints that permit articulation of varying degrees between bones. Those that permit free articulation are referred to as diathroses. Examples include the hip, knee, elbow and shoulder. A variety of connective tissues are associated with the diathroses joints, including intra-articular cartilages that provide cushioning and smooth sliding surfaces, ligaments that provide flexible connections between bones and tendons that slide over joints and connect the muscles to provide motion. When connective tissues are compromised, joint pain and loss of function can result.

One example of compromised connective tissue is osteoarthritis of the knee or knee OA. The knee joint is formed by the articulation of the femur, patella, and tibia (FIGS. 1A and 1B). Like other freely articulating joints, the knee joint is enclosed by a fibrous joint capsule, lined by a synovial membrane. The inferior surface of the patella articulates with the femoral surface forming the patellofemoral joint. The distal end of the femur has two curved articular surfaces called the medial and lateral condyles. These surfaces articulate with the medial and lateral tibial condyles, forming the tibiofemoral joint, which flexes and extends the knee. Two fibrocartilagenous discs (i.e., menisci) lie between the tibial and femoral condyles to compensate for the incongruence of the articulating bones. Because the distal end of the femur is curved and asymmetric in shape, the knee joint not only flexes and extends like a hinge, but it also slides and rotates during flexion, resulting in a complex motion for the joint.

Knee OA is one of the most common causes of disability in the United States. OA is sometimes referred to as degenerative, or wear and tear, arthritis. OA is characterized by the breakdown of the articular cartilage within the joint. Over time, the cartilage may wear away entirely, resulting in bone-on-bone contact. Since bones, unlike cartilage, have many nerve cells, direct bone contact can be very painful to the OA sufferer. In addition to the pain and swelling, the OA sufferer can experience a progressive loss of mobility at the knee joint. This is due to loss of the joint space, where the articular cartilage has completely worn away.

Biomechanics of Knee

The normal gait cycle of a human is shown in FIG. 2. The gait cycle begins when one foot contacts the ground and ends when that foot contacts the ground again. Thus, each cycle begins at initial contact with a stance phase and proceeds through a swing phase until the cycle ends with the limb's next initial contact.

The stance phase accounts for approximately 60 percent, and the swing phase for approximately 40 percent, of a single gait cycle. Each gait cycle includes two periods when both feet are on the ground. The first period of double limb support begins at initial contact, and lasts for about the first 10 to 12 percent of the cycle. The second period of double limb support occurs in about the final 10 to 12 percent of stance phase. As the stance limb prepares to leave the ground, the opposite limb contacts the ground and accepts the body's weight. The two periods of double limb support account for 20 to 24 percent of the gait cycle's total duration.

OA can affect all three compartments of the joint—medial, lateral and patella-femoral. Varus and valgus orientation of the lower extremity (defined as looking at the tibia from the knee towards the ankle) is commonly referred to as how-legged (varus) and knock-kneed (valgus) (FIG. 3). Normal alignment of the tibia is in mild varus relative to the vertical.

Excessive loading of the articular cartilage may occur due to obesity, joint misalignment or a combination of such factors. Overly varus alignment can lead to osteoarthritis in the medial compartment while valgus alignment can lead to osteoarthritis in the lateral compartment.

In patients suffering from patellofemoral OA, excessive compressive forces on the patello-femoral cartilage can cause pain and cartilage degeneration. Such excessive compressive forces are often generated during stair climbing. Two main moments acting around the knee joint during stair climbing are the ground reaction force due to the body weight and the quadriceps muscle force that acts on the patella through the quadriceps-femoris tendon and the patellar tendon.

Currently, various medications are often recommended to reduce the swelling and pain of OA. Other treatments such as weight loss, braces, orthotics, steroid injections and physical therapy may also help alleviate pain and restore function by strengthening muscles supporting the joint. However, since articular cartilage is avascular, or lacks a blood supply, repair and growth of adult cartilage is minimal. If the pain or immobility becomes too severe and other therapies do not alleviate the symptoms, surgical interventions become necessary. Surgical treatments include arthroscopy to clean the joint by removing loose fragments, tibial and femoral osteotomy, unicondylar knee replacement or total knee replacement.

SUMMARY OF DISCLOSURE

Exemplary methods disclosed herein comprise selecting at least one of the muscles and connective tissues associated with a joint as target tissue for treatment, and displacing the target tissue without severing the bones or target tissue, thereby redistributing loading in the joint to achieve a therapeutic effect.

In one implementation, the present disclosure is directed to an apparatus for treating disorders of articular joints, the joint being subject to forces exerted by soft tissues disposed proximate to the joint with the soft tissues forming target tissues for treatment, the apparatus comprising a prosthesis implantable in engagement with at least one target tissue so as to displace the target tissue sufficiently to alter the location, angle or magnitude of the forces exerted by the soft tissues so as to achieve a therapeutic effect in the joint. The prosthesis includes a fixation portion including bone fixation means configured to be secured in contact with a bone forming the joint at a fixation location outside the articular capsule of the joint, and a displacement portion configured and dimensioned to extend from the fixation portion to engage and displace the soft tissue, the displacement portion having an outer surface, wherein the displacement portion outer surface is smooth and free of holes or fixation means, and wherein the fixation portion of the prosthesis is configured to be mounted to the humerus.

In another implementation, the present disclosure is directed to a method of treating a shoulder joint having first and second bones. The method includes fixing a fixation portion of a treatment device to the first bone such that a displacement portion of the treatment device engages target tissue in a pretreatment location proximate the shoulder joint; and displacing the target tissue from the pretreatment location with the displacement portion of the treatment device by a distance and in a direction selected to provide a therapeutic effect in the shoulder joint.

In yet another embodiment, the target tissue exerts a force on the shoulder joint in the pretreatment location and the target tissue is displaced so as to redirect the force. Additionally, the moment may be increased by increasing a moment arm through which the force acts on the shoulder joint.

In further embodiments the therapeutic effect comprises at least one of reducing pain in the shoulder joint or increasing stability of the shoulder joint. Also, the displacing of the target tissue may redistribute a load on at least one articular surface in the shoulder joint and the displacement may be in a direction away from the shoulder joint. Further, the positioning may comprise fixing the fixation portion at a fixation location spaced from the articular surfaces of the shoulder by at least a distance corresponding to a length of a treatment device spanning section between the displacement portion and fixation portion. In some embodiments, the first bone is the humerus.

In some embodiments, the implant is secured on a first side of a joint to displace tissue on the first side of the joint in order to reduce a load on an opposing side of the joint. For example, the implant may be secured on a lateral side of the femur in order to reduce loads in the medial compartment of the knee. Or, the implant may be secured on a medial side of the femur to reduce loads in a lateral compartment of the knee.

In certain embodiments, tissue may be displaced such that a force in a first direction on one side of the joint is increased, while a second force in the first direction on an opposing side of the joint is decreased. For example, tissue may be displaced on a lateral side of the knee joint to increase the load on the articular surfaces in the lateral compartment while decreasing the load on the articular surfaces in the medial compartment.

In still further embodiments, connective tissue near a joint is displaced such that a moment arm through which the connective tissue acts upon the joint is increased, thereby reducing a load in the joint. An implant may be secured to a bone near the joint such that the implant displaces the connective tissue sufficiently to increase the moment arm.

In preferred embodiments, connective tissue near a joint is displaced sufficiently to achieve a therapeutically effective reduction in a load in the joint. Usually loads will be reduced at least about 5%, preferably at least about 10%, more preferably at least about 15%. The magnitude of displacement required to achieve these load reductions will vary depending upon the joint, size and condition of the patient, and other factors. In the case of osteoarthritis in the medial and lateral compartments of the knee, displacement of connective tissue by at least about 8 mm, often by at least about 10 mm, will usually be required.

In another exemplary embodiment, a method for treating medial osteoarthritis of the knee comprises laterally displacing the iliotibial band. Such an embodiment may further comprise selecting at least one of the muscles and connective tissues associated with a joint as target tissue for treatment, displacing the target tissue without severing the bones or target tissue, the target tissue being displaced in a region where it is not crossing the joint, wherein the displacement redistributes loading in the joint to achieve a therapeutic effect.

Another exemplary method disclosed herein comprises selecting at least one of the associated muscle and connective tissues surrounding a joint as target tissue for treatment, displacing the target tissue without severing the bones or target tissue, thereby altering the kinematics of the joint to achieve a therapeutic effect. In some embodiments the kinematics are altered to redistribute loading in the joint to achieve the therapeutic effect. In other embodiments the kinematics are altered to reduce loading on the ligaments within the joint to achieve the therapeutic effect.

One of the exemplary methods disclosed herein comprises selecting at least one of the associated muscle and connective tissues as target tissue for treatment, displacing the target tissue without severing the bones or target tissue, and redistributing loading in the joint to achieve a therapeutic effect. The apparatus may be completely outside the capsule surrounding the joint or may be in contact with the exterior of the capsule.

Embodiments of the present invention may be applied to virtually any articular joint, including but not limited to the knee, shoulder or hip. In addition to the implants and related prosthesis and apparatus described, embodiments of the present invention include methods of treating joint disorders and methods of installing implants and prostheses for less invasive joint treatments.

By using the implants of the invention, appropriately sized and positioned as described herein, displacement of targeted connective and muscle tissues surrounding the joint is accomplished in order to realign force vectors and/or alter moment arms loading the joint to achieve therapeutic effects without cutting bone and with minimal cutting of the connective tissues. Alternative and more specific devices and methodologies are described in more detail herein below.

BRIEF DESCRIPTION OF DRAWINGS

For the purpose of illustrating the invention, the drawings show aspects of one or more exemplary embodiments of the invention. However, it should be understood that the present invention is not limited to the precise arrangements and instrumentalities shown in the drawings, wherein:

FIG. 4 depicts an exemplary embodiment of a prosthesis according to the present invention.

FIGS. 5A-D depict the cross-sectional views of the displacement portion of the prostheses according to one embodiment of the present invention.

FIG. 6 is an anterior view of a right knee illustrating positioning of another exemplary embodiment of the present invention for treating lateral compartment osteoarthritis.

FIG. 7 is an anterior view of a right knee illustrating positioning of another exemplary embodiment of the present invention for treating lateral compartment osteoarthritis.

FIG. 21 is a schematic cross sectional view of an further alternative embodiment including a multi-chamber capsule between two solid members.

FIG. 22 is a schematic cross sectional view of another alternative embodiment of the present invention incorporating an adjustable mechanical construct between two solid members.

FIG. 23 is an anterior view of a right knee illustrating positioning of another exemplary embodiment of the present invention for treating medial compartment osteoarthritis.

FIGS. 24, 25 and 26 are side schematic side views of prostheses according to alternative exemplary embodiments of the present invention.

FIGS. 50A-E and 51 are views of prostheses for lateral displacement of the IT Band in the right knee in accordance with other exemplary embodiments of the present invention, wherein FIG. 50A is a perspective view, FIG. 50B is a top view, FIG. 50C is a side view as seen from the anterior side of the implant, and FIG. 50D is a side view as seen from the posterior side of the implant. FIGS. 50E and 51 are views of a prosthesis for lateral displacement of the IT Band in the right knee in accordance with yet another exemplary embodiment of the present invention, wherein 50E is a cross-sectional view of the implant sectioned through A-A, and 51 is a cross-sectional view of the implant sectioned through B-B of FIG. 50B.

FIGS. 56A-D are views of an exemplary embodiment of an inserter device for implanting the prosthesis of the present invention.

FIGS. 58A-B are views of an exemplary embodiment of a dissection device for implanting the prosthesis of the present invention.

DETAILED DESCRIPTION

Figure 1A:
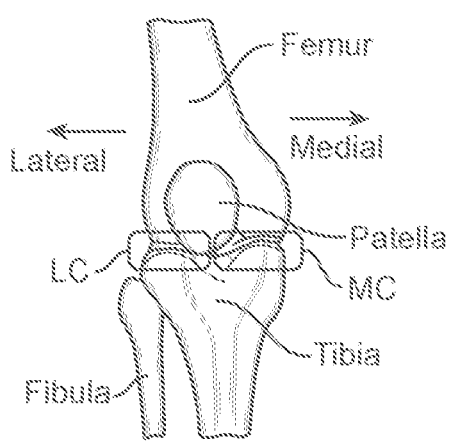
FIG. 1A is a front or anterior view of the bones of the right knee joint in a human, illustrating the lateral and medial directions and the medial and lateral compartments of the knee.

Utilizing embodiments of the present invention, joint conditions that result from or exacerbate unbalanced force distribution through the joint may be addressed by interventional techniques involving a redistribution of forces exerted on the joint without the need for highly invasive surgeries requiring significant trauma to the joint and associated muscle and connective tissues. Redistribution of forces within the target joint in accordance with embodiments described herein may thus provide pain relief or slow down articular cartilage degeneration or enhance cartilage regeneration.

In some embodiments of the invention, increased forces can be selectively applied to one side of a joint by routing select muscle, tendons, ligaments, and/or other connective tissues (target tissues) around a longer or more angled path, thus increasing the magnitude, altering the effective direction, and/or changing the moment arm of forces exerted by such muscles or tissues on the joint. This may be accomplished, for example, by appropriately shaped implants that may be positioned to displace selected target tissues relatively non-invasively compared to current surgical techniques for addressing such conditions. The amount of displacement of the target tissue may not need to be large in order to provide a substantial therapeutic effect on the target joint. For example, in the knee, depending upon the nature of the disease and the size and geometry of a particular patient's joint, displacements of greater than about 5 mm up to about 30 mm may be sufficient, with displacements in the range of about 10 mm to about 30 mm also suitable, or more specifically about 10-20 mm.

Exemplary embodiments of the invention described herein are particularly directed to treatment of the human knee, although the principles of the invention may be applied to other joints as described in the copending parent application of the present application, which as stated above is incorporated by reference herein. In general, it will be appreciated by persons of ordinary skill in the art that specific features described in connection with one exemplary embodiment may be incorporated in other exemplary embodiments unless otherwise noted. The exemplary embodiments described are thus included to illustrate features of the invention, not limit it.

As used herein, "therapeutic effect" means an effect on a treated joint that reduces forces acting on the articular surfaces, reduces wear, lessens pain or provides another positive outcome for the patient whether across the joint as a whole or in particular compartments of the knee. "Therapeutic effect," however, does not imply, and should not be understood as requiring, any specific, quantified outcome other than as stated above.

As used herein, in humans, dorsal refers to the back of an organism and ventral to the belly. Cranial refers to the head end and caudal to the tail end. In humans, anterior is used to indicate the ventral surface and posterior to indicate the dorsal surface. Superior means toward the head and inferior toward the feet. Proximal refers to the end of a structure nearest a major point of reference and distal to the end furthest from a point of reference. The point of reference is usually the origin of a structure (such as a limb). Proximal and distal are relative terms. Medial means nearer the midline of the body and lateral means further from the midline. Superficial refers to structures nearer the skin, and deep to structures further away from the skin. A sagittal plane divides the body into right and left (or medial and lateral) parts. A frontal (or coronal) plane passes from right to left and divides the body into dorsal and ventral (or posterior and anterior) parts. A transverse plane (or cross section) passes perpendicular to the long axis of the body and divides the body into cranial and caudal (head and tail) portions.

Figure 1B:
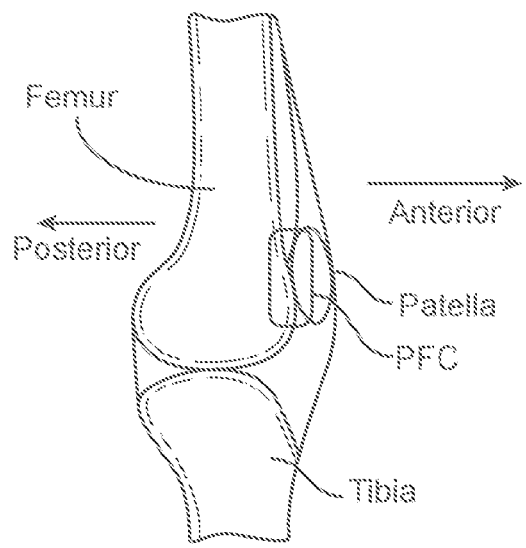
FIG. 1B is a sagittal or vertical section of the right knee joint, illustrating the anterior and posterior directions and the patellofemoral compartment of the knee.
Figure 2:
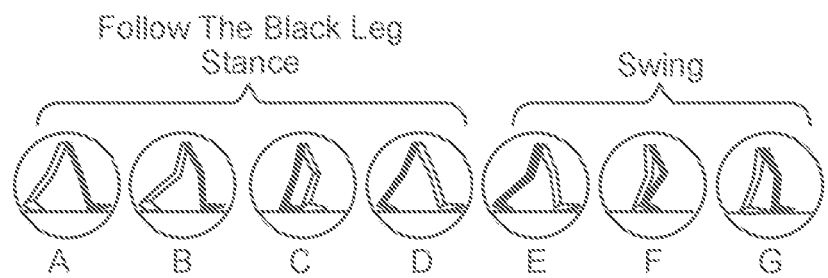
FIG. 2 is a schematic diagram illustrating the human gait cycle.
Figure 3:
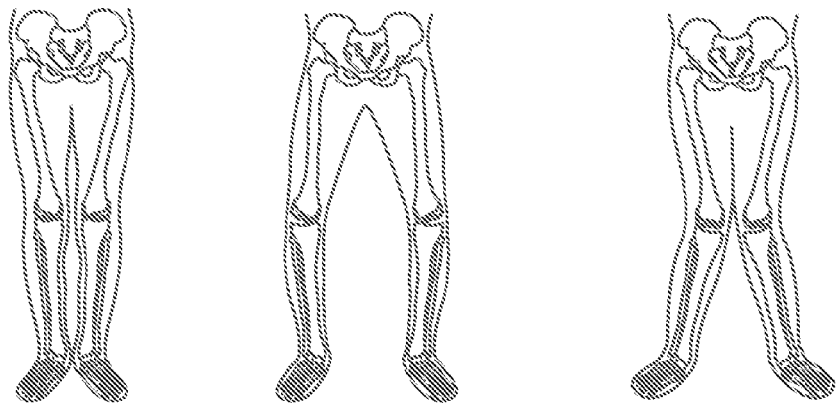
FIG. 3 is a figure depicting normal knees, bowlegged knees (varus misalignment) and knock knees (valgus misalignment).

While illustrated in FIGS. 1A and 1B for the sake of clarity, persons of ordinary skill in the art will understand the location and anatomy of the compartments of the knee, commonly referred to as the Medial Compartment (MC), Lateral Compartment (LC) and Patellofemoral Compartment (PFC). Also illustrated in FIGS. 1A and 1B are anatomical directions relative to the knee joint as referenced herein.

Implants according to embodiments of the present invention may be configured and secured in a variety of ways as described below in more detail with respect to exemplary embodiments. However, in general, and with reference to FIG. 4, prostheses or implants according to embodiments of the invention will, in preferred embodiments, comprise a fixation portion 12 that provides means for securing or anchoring the prosthesis, such as holes 13 for bone screws 15, and a displacement portion 14 configured and dimensioned to displace the target tissue(s) from a pretreatment path as described herein. Other means for securing the fixation portion may include bone ingrowth surfaces, barbs, bone cement and other devices known in the art for securing implants to bone. The fixation and displacement portions may be separated by a spanning section 16 that permits those portions to be separated from each other as appropriate to accommodate the anatomical structures at the location of treatment and fixation. The displacement portion 14 may be provided with a bearing member 17 of the same or a different material than the underlying substrate. In some embodiments, again depending on anatomical structures and treatment requirements, two or more of the displacement and fixation portions and spanning section may be merged in whole or in part or may overly one another.

Figure 9A:
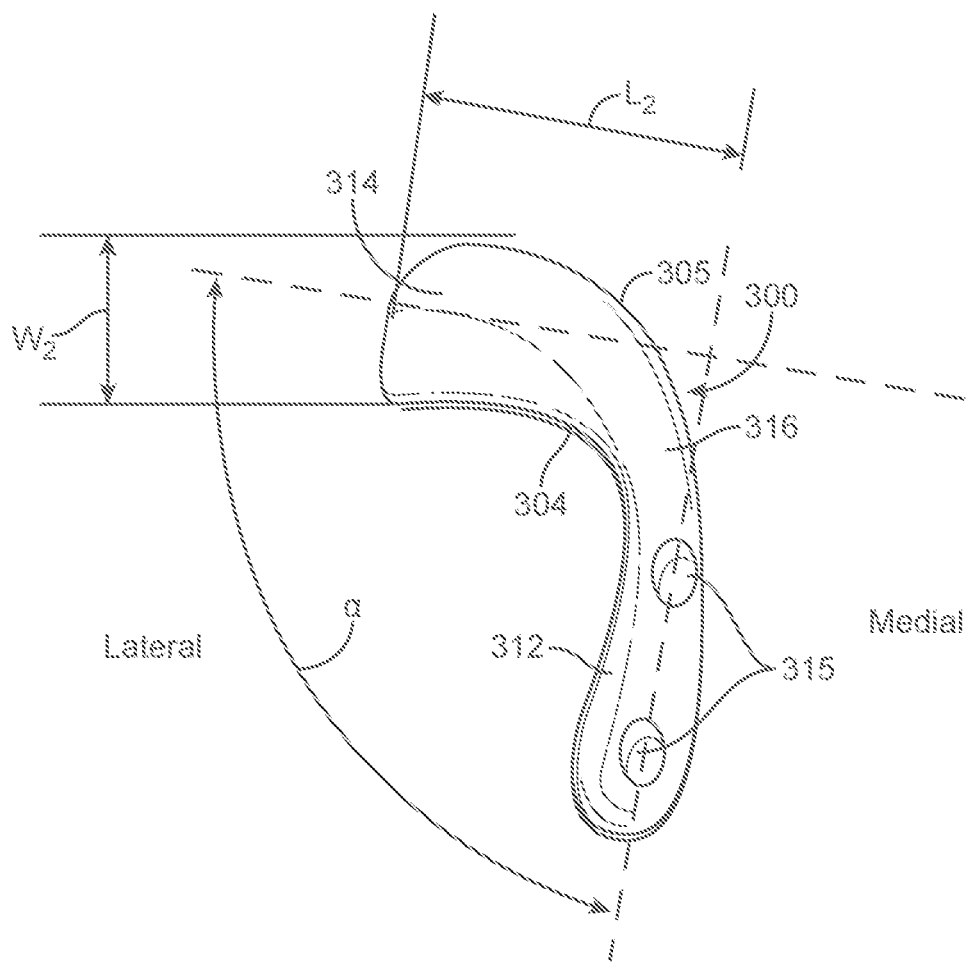
FIGS. 9A-E are views of a an exemplary prosthesis for anterior displacement of the patellar tendon in the right knee, wherein 9A is a perspective view, 9B is an anterior (front) view, 9C is a lateral (side) view, 9D is a posterior (back) view and 9E is a cranial (top) view.
Figure 9B:
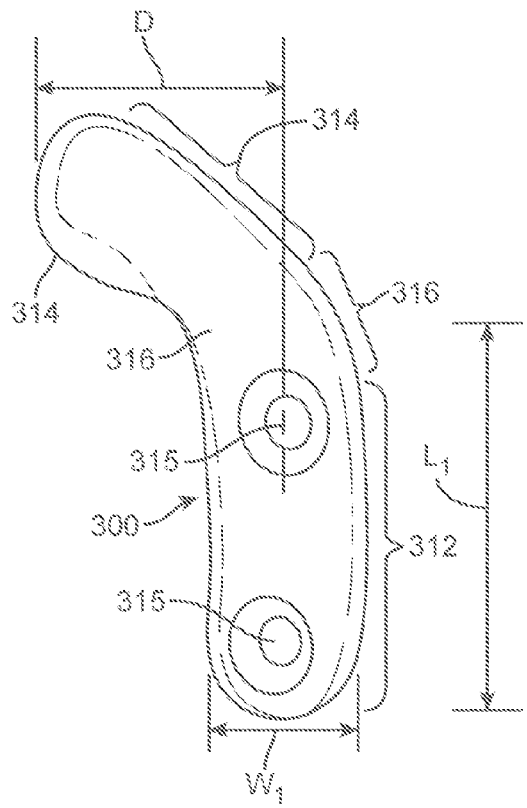
Figure 9C:
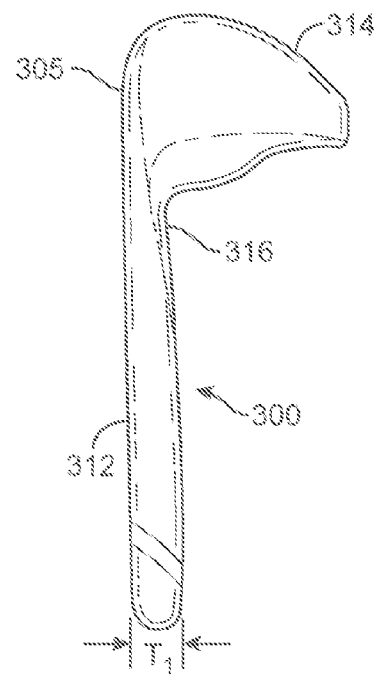
Figure 9D:
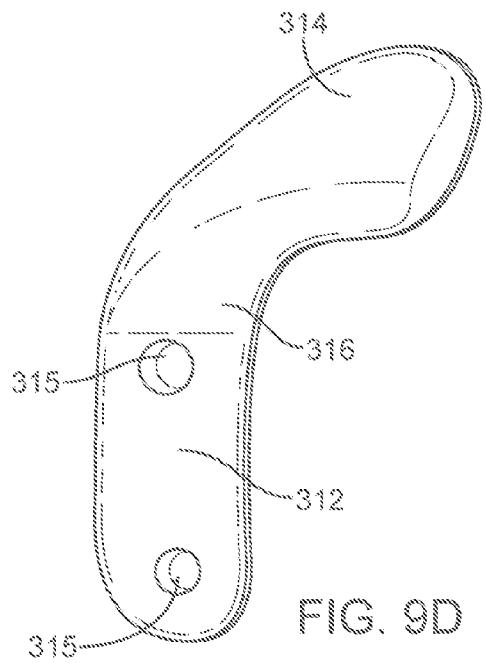
Figure 9E:
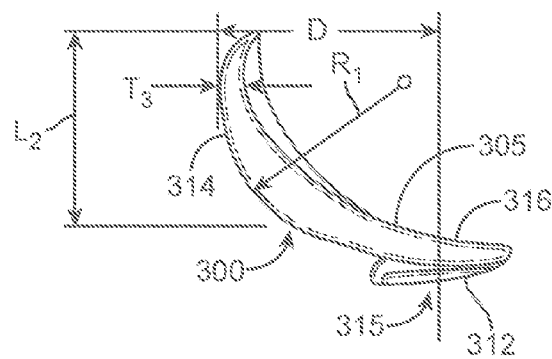
Figure 18A:
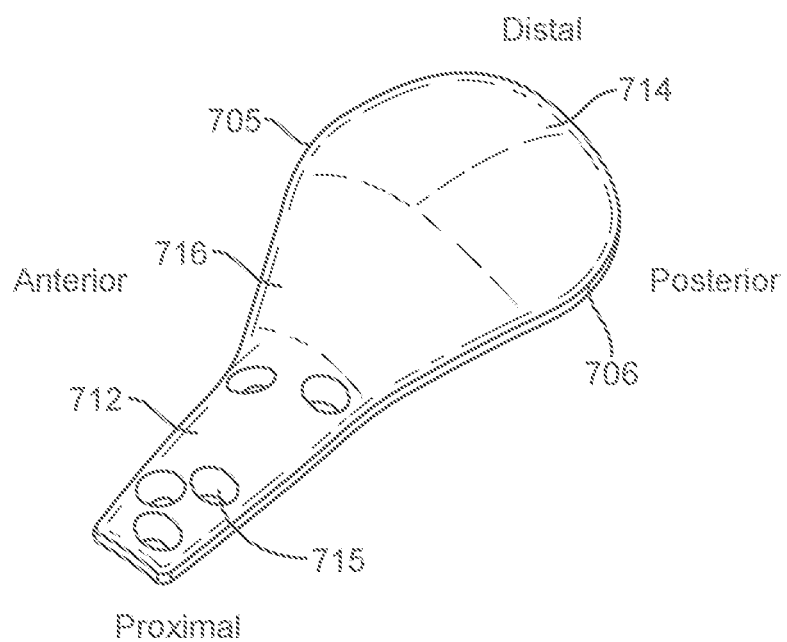
FIGS. 18A-D are views of a prosthesis for lateral displacement of the IT Band in the right knee in accordance with yet another exemplary embodiment of the present invention, wherein 18A is a perspective view, 18B is a lateral view, 18C is an anterior view and 18D is the caudal (bottom) view.
Figure 18C:
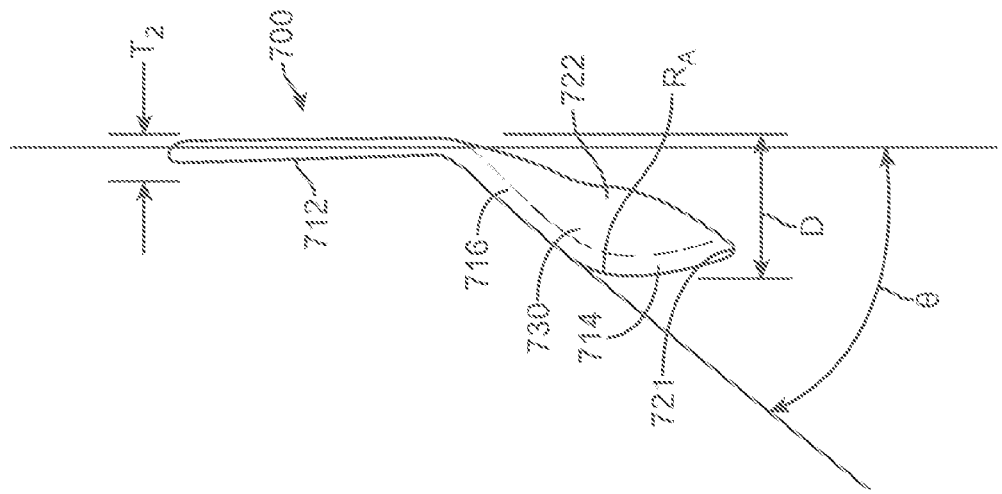
Figure 18B:
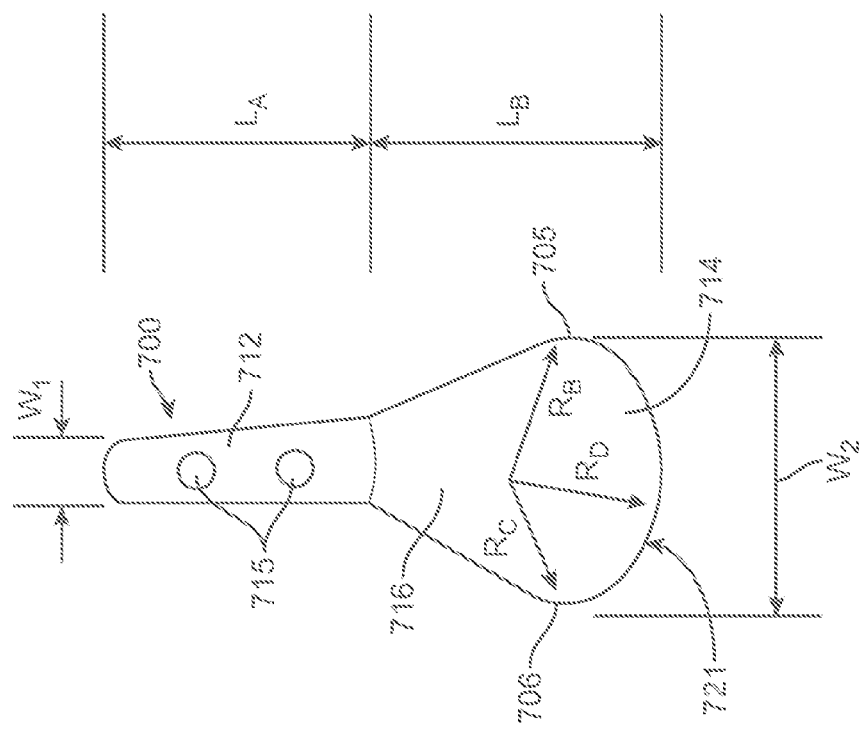
Figure 18D:
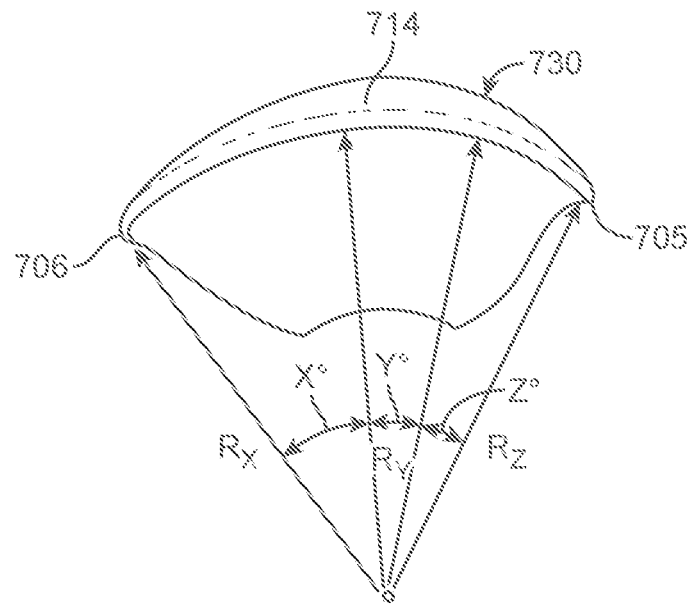

Depending on the mechanical load on the implant, and the choice of material or materials used to fabricate the implant, thickness of the fixation portion (for example; $T_1$ in FIG. 9E, $T_2$ in FIG. 18C) of the implant typically ranges from about 2.0 mm to 8.0 mm, more typically from about 2.5 mm to 6.0 mm, and may be from about 3.0 mm to 4.5 mm. The thickness of the fixation portion of the implant (for example; $T_3$ in FIG. 9E) may be uniform throughout the implant or may vary across the implant. Regions of the fixation portion under higher mechanical load may be thicker than regions under lower mechanical loads. The thickness of the fixation region may also be selected to ensure that the screw-heads used to fix the implant do not protrude over the surface of the implant. Examples of thickness $T_1$, $T_2$ etc. are shown in FIGS. 9C, 9E and 18C.

The spanning section may have thickness similar to that of the fixation portion. Persons of ordinary skill in the art will appreciate that a principal consideration for spanning section is sufficient structural integrity to maintain the displacement portion at the desired treatment position. In the displacement portion, displacement distance and thickness may be considered separately. Displacement distance is the distance by which the bearing surface of the displacement portion displaces the target tissue beyond the natural anatomical track of the target tissue, in other words, the displacement of tissue created by the implant. Depending on the particular geometry of the implant, the thickness of the displacement portion may or may not be related to the displacement distance. For example, in an implant with a convex or spoon shaped displacement portion (see, e.g. FIG. 18), or one with a displacement portion that is cantilevered at an angle or stepped into a different plane from the fixation portion or spanning section, the thickness of the material may be substantially less than the overall displacement distance. For example, a material thickness of 4 or 5 mm in the displacement portion may provide sufficient structural integrity for a displacement distance of 25 to 30 mm depending on the material selected. In one embodiment, displacement of the target tissue results in the decrease in the mechanical load on the articular cartilage in the target joint by at least 5%, more preferably by at least 8%, most preferably by at least 10%. Unloading as defined here refers to decrease in contact forces, either peak forces or average forces, either measured or calculated, during a normal gait cycle, stair climbing, running, jogging or any other physical activity which results in mechanical loading of articular cartilage in a joint.

The displacement distance provided by the displacement portion of the implant may typically range from greater than about 5 mm to about 30 mm. Of course, the actual displacement distance will depend upon the joint being treated, the location and physical characteristics of the target tissue, the severity of disease, and other factors. In some embodiments, displacement distance across the displacement portion may vary. As further examples of how displacement distance and thickness may relate, the displacement portion may be in contact with the underlying tissue and the target soft tissue is displaced by a distance equivalent to the thickness of the displacement portion; thus displacement distance would equal thickness in such an embodiment. In other embodiments, the displacement portion may be elevated above the underlying tissue and the target soft tissue is displaced by a distance greater than the thickness of the displacement region; thus displacement distance is greater than thickness.

Persons of ordinary skill in the art will thus appreciate that a further dimension to be considered is the depth (D) of the implant that governs the magnitude of tissue displacement, i.e., the perpendicular distance from an outer most point on the bearing surface to a point on the fixation surface, that is, the surface of the fixation portion configured to face the fixation site. Typically, depth (D) will be measured as perpendicular to a plane tangent to an outer most point on the bearing surface, between that plane and a point on the fixation surface that defines the location of fixation to the bone, for example a centerline of the fixation element(s) such as screw holes, provided in the fixation portion. Examples of depth (D) are shown in FIGS. 9B, 9E and 18C.

In alternative embodiments, components of the prosthesis may be a compliant material such as an elastomer, capsules filled with water, saline, silicone, hydrogels, etc. Embodiments with compliant portions could be placed in a deflated state and then inflated to the appropriate thickness. Alternatively, bearing members may be filled with other flowable materials including beads or other particles made of metal, polymer, or foam material, optionally in a liquid medium, which conform to the adjacent bone or tissue surfaces. Thixotropic materials, such as hydrogels derived from hyaluronic acid, change their mechanical properties as shear stress is applied to them. An implant filled with such materials could be made to change the amount of displacement that it provides based on the shear stress that it sees from overlying target tissues at various points in the gait cycle. Implants may be coated with materials to reduce friction such as hydrophilic coatings or polytetrafluoroethylene (PTFE) coatings. Additionally or alternatively, the prosthesis may be adjustable to allow the dimensions such as thickness of the prosthesis to be adjusted during surgery or any time after surgery.

Rigid or substantially rigid prostheses according to embodiments of the invention described herein could be made of known bone-compatible implant materials such as titanium or stainless steel. Biocompatible polymers, ceramics, and other materials may also be used. The bearing surface of the prostheses should be designed to minimize negative effects of movement of the connective tissues across the implant surface, e.g. comprising a smooth, atraumatic, low-friction material, coating or surface treatment. Such prostheses could be implanted arthroscopically or using a mini-open or open surgical approach.

In various alternative embodiments, the displacement portion and the fixation portion of prostheses according to the invention may be of unibody construction, or may be formed of two or more parts depending on desired function. For example, the fixation portion may be stainless steel or titanium textured to enhance bony ingrowth and solid screw fixation, while the displacement portion could be made of a different material, for example, pyrolytic carbon to enhance the ability of overlying tissues to slide across the implant, or PTFE, silicone or other low-friction polymer with suitable wear characteristics to provide a softer bearing surface. In this regard, the displacement portion may comprise a separate bearing member with a bearing surface on which the target tissue bears. Alternatively the bearing surface may be formed as an integral part of the displacement portion. In further alternatives, the displacement portion could be comprised of a substrate of one material with an overlying layer forming the bearing member. The substrate could be either attached to or contiguous with the fixation portion. In other embodiments, the fixation portion of the implant may have a relief feature to minimize contact with the underlying bone, thereby minimizing disruption of the periosteal layer.

Generally, the bearing member and/or bearing surface in embodiments of the invention will be hard and smooth, made from materials such as polished pyrolytic carbon, steel, or titanium, or coated or covered with a lubricious material, such as PTFE. However, in embodiments where relative motion is provided for within the prosthesis itself, such as in exemplary embodiments described herein below, the bearing surface may be designed to encourage adhesion and ingrowth of the connective tissue onto this surface. For example, such a surface may be porous, roughened, or configured with openings into which bone or scar tissue may grow to enhance adhesion.

In some embodiments, the implant could be anchored to the underlying bone with suitable fasteners such as screws. Depending on the location and surgical need, unicortical screws, bicortical screws, cancellous screws, cannulated screws, polyaxial screws, screws that lock into the implant etc. may be used. In some embodiments, the screw holes may be locking threads or other locking features. In other embodiments, the screws holes may be oriented in different directions to improve the stability of the anchored implant. In alternate embodiments, different types of screws may be used in different regions of the implant. For example, cortical screws may be used in the region of the implant in contact with the femoral shaft while cancellous screws may be used in another part of the implant in contact with femoral condyle. Depending on patient anatomy and geometry of a specific implant, it may be desirable to provide supplemental fixation (such as cancellous bone screws) in the spanning section.

As discussed above, lateral condylar osteoarthritis may be caused by excessive loading of the lateral condyle. Excessive loading may result from obesity or joint misalignment (valgus or knock knees). By medially displacing the medial muscles or tendons like the sartorius and gracilis muscle or tendon, the moment arm of the muscle or tendon as it crosses the joint may be increased, thereby redistributing the forces within the joint, and reducing the load on the lateral condyle. Other muscles and tendons around the knee that contribute to the medial stability of the knee may also be displaced to achieve a similar therapeutic effect.

FIGS. 6 and 7 show exemplary embodiments of the present invention for medial displacement of the medial muscles or tendons around the knee. FIG. 6 depicts a first embodiment of an implant 100 anchored on the medial side of the tibia. The definitions of the dimensions (for example, L, W, T, D etc.) of the implant in FIG. 6 are the same as those for the implant in FIG. 9. Fixation portion 112 of the implant is used to anchor the implant, e.g. with screws 113, and displacement portion 114 displaces the sartorius and/or gracilis tendon medially. The fixation portion could be attached to the tibia adjacent to the attachment point of the patellar tendon and the tibia or it could be located more cranial or caudal to the attachment point. In one exemplary embodiment of implant 100, the width of the fixation portion 112 ranges from about 10 mm to 25 mm, more specifically from about 12 mm to 20 mm, and in certain embodiments from about 14 mm to 18 mm. The length of the fixation portion 112 for implant 100 may be in the range of about 20 mm to 50 mm, more specifically from about 25 mm to 45 mm, and in certain embodiments about 30 mm to 40 mm. Spanning section 116 would be configured to transition from fixation portion 112 mostly parallel to the medial side of the tibia to displacement portion 114, which, as stated above, is configured and dimensioned to displace the sartorius or gracilis tendon medially.

The displacement of the target tissue can be altered by changing the length, curvature and angle of the spanning section 116, with an embodiment such as implant 100, each affecting the overall depth of the implant. For example, the angle between the displacement portion 114 and the fixation portion 112 (angle as measured at the intersection of the center line axes of the two portions in the top view of the implant similar to angle α shown in FIG. 9A) may range from about 80 degrees to 135 degrees, more specifically about 85 degrees to 120 degrees, and in some from about 90 degrees to 110 degrees. The inferior edge of the spanning section 116 can also be curved to minimize or eliminate any contact with the anterior edge of the sartorius or gracilis tendon and could be configured to avoid the attachment region of the tendons to the tibia. The displacement of the target tissue may also be altered by changing the cross-section of the displacement portion. The width of the displacement portion 114 may range from about 10 mm to 25 mm, more specifically about 12 mm to 20 mm, and in some embodiments about 14 mm to 18 mm. The length of the displacement portion 111 may range from about 20 mm to 50 mm, more specifically about 25 mm to 45 mm, and in some embodiments about 30 mm to 40 mm. The length and width should be sufficient to provide adequate support of the target tissue over its range of motion without excessive or extra material. By appropriate adjustment of these dimensions a person of ordinary skill in the art may configure the implant with a depth to provide displacement of the target tissue in the range of about 5 mm to 30 mm.

Another embodiment is shown in FIG. 7, which depicts implant 200 anchored on the medial side of the femur. The definitions of the dimensions of the implant (for example, L, W, T, D etc.) in FIG. 7 are the same as those for the implant in FIG. 18. Fixation portion 212 of the implant is used to anchor the implant and displacement portion 214 displaces the sartorius and/or gracilis tendon medially. Displacement portions 114 and 214 may be adjusted to provide appropriate displacement to achieve a therapeutic effect as described. In an exemplary embodiment, displacement portion 214 is offset medially relative to fixation portion 212 so as to extend around the medial facet of the femoral condyle. The displacement portion 214 may be generally parallel with the fixation portion 212, and be interconnected by a spanning section 216 which extends at an angle medially and caudally from fixation portion 212. The spanning section extends the displacement portion out medially to achieve a desired displacement. Additionally, spanning section 216 is configured and dimensioned to reduce contact or impingement with bone or soft tissue underneath the displacement portion (e.g.; joint capsule, tibial collateral ligament etc.). The fixation portion 212 may lie in a place which is generally parallel to the displacement portion 214, with both configured to lie on the medial aspect of the bone when implanted. Alternatively, displacement portion 214 may be in a plane which is nonparallel to that containing the fixation portion; for example the fixation portion may be configured and dimensional for attachment to a more anterior aspect of the tibia while the displacement portion is configured to face more medially with the spanning section, bridging the region between the displacement portion and fixation portion.

The width of implant 200 as measured in the anterior-posterior direction may vary depending on anatomical conditions and other factors as determined by the surgeon. For example, the width of implant 200 in fixation portion 212 could be constant while the width of the displacement portion 214 could vary along its length to cover the medial facet of the condyle. The width of the spanning section 216 would bridge the difference in widths between the fixation portion and the displacement portion. In exemplary embodiments, the width of fixation portion 212 may range from about 10 mm to 40 mm, more specifically about 15 mm to 35 mm, and in some embodiments about 20 mm to 30 mm. The length of the fixation portion 212 may range from about 20 mm to 60 mm, specifically about 30 mm to 50 mm, and in some embodiments about 35 mm to 45 mm. The width of the displacement portion 214 may range from about 40 mm to 70 mm, more specifically about 45 mm to 65 mm, and in some embodiments about 50 mm to 60 mm. The length of the displacement portion 212 may range from about 40 mm to 70 mm, more specifically about 45 mm to 65 mm, and in some embodiments about 50 mm to 60 mm.

Patellofemoral osteoarthritis may be caused by excessive compressive load on the patella. By anteriorly displacing the patellar tendon or the quadriceps-femoris tendon the compressive load on the patella may be reduced. While it has been recognized that such displacement of the patellar tendon may have benefits, existing approaches have suffered from certain difficulties. For example, it has been suggested that a prosthetic implant could be inserted and anchored beneath the patellar tendon cranially from the tendon insertion point on the tibia. However, because the tendon overlies this area, obtaining access and clear visualization of the anchoring site can be difficult. Moreover, the area of the bone available to insert screws is limited, requiring the screws to be placed closer together than would be ideal for secure anchoring. Further, anchoring a device to the tibia at this location risks damaging the patellar tendon and other ligaments and tendons which insert into the tibia nearby. In addition, such an implant can cause a cosmetically unattractive bump. In the present invention, by contrast, implants may be configured such that the displacement portion of the implant is separated from the fixation portion of the implant. With the displacement portion positioned under the target tissue (e.g. patellar tendon), the fixation portion of the implant may be configured to be affixed to the bone at a location which can securely fix the implant in place, is accessible to the surgeon, is not covered by the target tissue, and is separated from tendon insertion points and other anatomical features. The implant may have a spanning section shaped and dimensioned to bridge the distance between the fixation portion and the displacement portion. The implants may be configured to move the tendon anteriorly or medially or anterior-medially or laterally or antero-laterally. This may be accomplished by making one side (lateral or medial) of the displacement surface higher than the other, and/or by forming a track with ridges on one or both sides of the bearing surface to urge the tendon in a lateral or medial direction.

Figure 8:
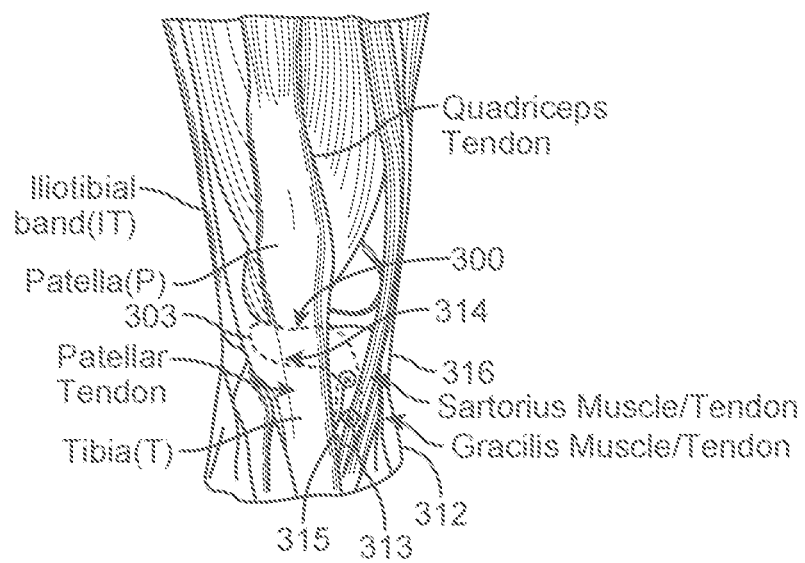
FIG. 8 is an anterior view of a right knee illustrating positioning of an exemplary embodiment of the present invention for treating patellofemoral osteoarthritis or chondromalacia.

FIG. 8 shows such an exemplary embodiment of the present invention for displacement of the patellar tendon. Implant 300 is anchored on the medial side of the tibia. Fixation portion 312 of the implant is used to anchor the implant and displacement portion 314 displaces the patellar tendon. Advantageously, the fixation portion is separated from the displacement portion by spanning section 316 so that the fixation portion may be shaped and dimensioned to optimize anchoring, holes 315 for screws 313 may be more numerous and separated further apart, and the location on the bone for anchoring may be more easily accessed and visualized by the surgeon. Additionally, the fixation portion may be configured to minimize skin irritation. For example, by configuring the displacement portion 314 to rest on the bone underneath the patellar tendon, the load on the device could be distributed such that the stress on the fixation portion 312 is reduced. Reduction in the stress on the fixation portion 312 would enable that portion to have a lower profile or lower thickness, thereby reducing any skin irritation and achieving other attendant benefits of a smaller profile. In an alternative embodiment, the displacement portion may be elevated from the underlying bone such that only the most lateral region 303 of the implant is in contact with the tibia, thereby minimizing any damage to the periosteal layer.

FIGS. 9A-E depict an exemplary prototype of implant 300 for treating patellofemoral osteoarthritis and/or patellar maltracking for the right knee as depicted in FIG. 8. Implant 300 has a fixation portion 312 having one or more holes 315 for receiving screws for anchoring the implant to bone. Fixation portion 312 is generally straight and elongated, being configured for positioning in general alignment with the tibial shaft on the medial or anterior-medial side of the tibia. Holes 315 are preferably positioned in approximate alignment with a longitudinal centerline of fixation portion 312. Displacement portion 314, is configured and dimensioned to be positioned under the patellar tendon cranially separated from the insertion point of the tendon in the tibia. The displacement portion 314 is configured to atraumatically engage the tendon and displace it anteriorly relative to the tibia. The displacement portion 314 has a length in the lateral-medial direction selected to accommodate the full width of the tendon so that the tendon remains engaged along its entire width as it slides on the displacement portion. Displacement portion 314 preferably has a convex curvature on its outer tissue-engaging surface (bearing surface), preferably being curved at least around an axis generally parallel to the tibial shaft, usually being curved also around an axis perpendicular to the tibial shaft, and more preferably being spherical or partially spherical. Displacement portion 314 has a width in the caudal-cranial direction is selected so that it does not interfere with the patella or engage the insertion point of the tendon, typically being less than its length. A spanning section 316 interconnects fixation portion 312 and displacement portion 314. Spanning section 316, in the embodiment illustrated, extends cranially and laterally from fixation portion 312 to displacement portion 314, forming a curve of about 90° about a dorsal-ventral axis. Where fixation portion 312 is configured for attachment to a more medial aspect of the tibia, spanning section 316 will extend ventrally as well as cranially and laterally from fixation portion 312, preferably being curved about an axis generally parallel to the tibial shaft. Displacement portion 314 appropriately displaces the patellar tendon in cooperation with the fixation portion 312 and spanning section 316.

Displacement of the target tissue can be altered by changing the length, curvature and angle of the spanning section among other features. For example, the angle α between the displacement portion 314 and the fixation portion 312 (as measured at the intersection of the center line axes of the two portions in the top view of the implant in FIG. 9A) may range from about 80 degrees to 135 degrees, more specifically from about 85 degrees to 120 degrees, and in some embodiments about 90 degrees to 110 degrees. The width $W_1$ of the fixation portion 312 will be large enough to span a substantial portion of the width of the tibia and to accommodate one or more screw holes of sufficient size, ranging from about 10 mm to 25 mm, more specifically about 12 mm to 20 mm, and in some embodiments about 14 mm to 18 mm. The length $L_1$ of the fixation portion 312 will be selected to accommodate a sufficient number of screw holes in the cranial-caudal direction along the tibia, usually at least two and in some embodiments up to five or more, and may range from about 20 mm to 50 mm, more specifically about 25 mm to 45 mm, and in some embodiments about 30 mm to 40 mm. The width $W_2$ of the displacement portion 314 is selected to provide a broad area of contact with the tendon to spread the force and reduce wear, while not interfering with the patella or the tendon insertion point throughout the full range of joint motion. Width $W_2$ may thus range from about 10 mm to 25 mm, more specifically about 12 mm to 20 mm, and in some embodiments about 14 mm to 18 mm. The length $L_2$ of the displacement portion 314 is selected so that the displacement portion extends under the full width of the tendon so that the entire width of the tendon remains in engagement and displaced the desired amount throughout the range of joint motion. Length $L_2$ may thus range from about 20 mm to 50 mm, more specifically about 25 mm to 45 mm, and in certain embodiments about 30 mm to 40 mm. Implant depth D, along with the radius of curvature $R_1$ of the outer surface of displacement portion 314, shown in FIG. 9E, are selected to optimize tendon displacement throughout the range of joint motion. Radius of curvature $R_1$ is usually 20-35 mm, more preferably 22-33 mm, and most preferably 25-30 mm. For average patient anatomy, an overall implant depth (D), shown in FIGS. 9B and 9E, as measured from the outermost surface of displacement portion 314 to the centerline of the screw holes in fixation portion 312, would be in the range of 10-45 mm in order to provide target tissue displacements in the ranges cited hereinabove to achieve a therapeutic effect.

The inferior edge 304 of the spanning section 316 can also be curved to minimize or eliminate any contact with the medial edge of the patellar tendon. The superior surface edge 305 of the displacement portion 314 can be curved to allow for easy motion of the patellar tendon during flexion as well as to vary the displacement of the patellar tendon during flexion by varying the region of the implant surface in contact with the tendon at higher flexion angles. In one exemplary embodiment, implant 300 is placed on the medial side of the distal tibia such that fixation portion 312 is substantially aligned with the tibial shaft, the spanning section 316 is positioned to minimize contact with the medial edge of the patellar tendon, and the displacement portion 314, extending laterally from the spanning section, is substantially parallel to the tibial plateau.

Figure 10:
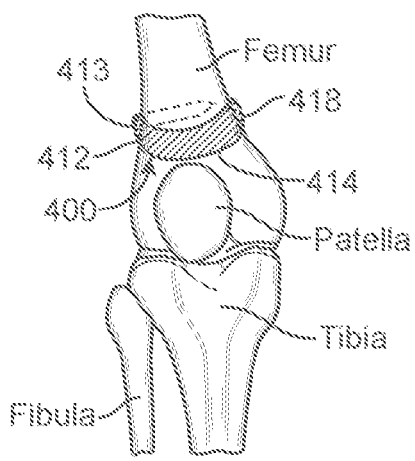
FIGS. 10, 11 and 12 are views of prostheses according to alternative exemplary embodiments of the present invention for anterior displacement of the quadriceps-femoris tendon.
Figure 11:
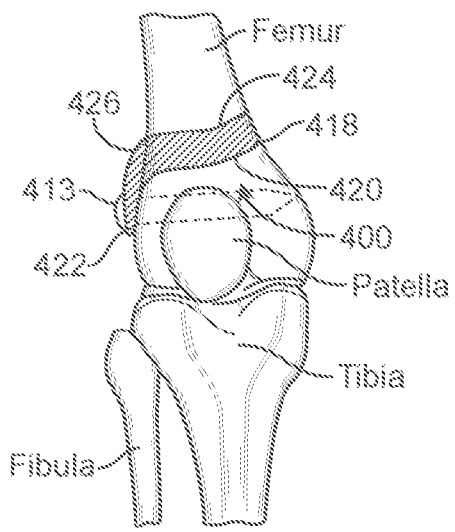
Figure 12:
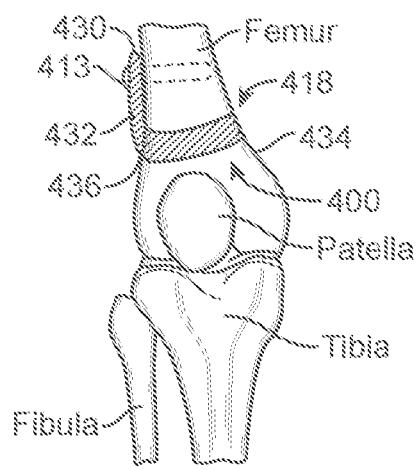

FIGS. 10, 11 and 12 show exemplary embodiments of implants according to the present invention for displacement of the quadriceps-femoris tendon. FIG. 10 depicts implant 400 anchored on the lateral side of the femur using one or more fixation screws 413. Holes (not visible in the figures) extending through fixation portion 412 for receiving screw (s) 413 are oriented in a lateral-medial direction so screw(s) 413 may be inserted into a lateral aspect of the femur. Displacement portion 414 extends generally orthogonally in a medial direction from fixation portion 412 so as to extend across an anterior aspect of the femur under the quadriceps-femoris tendon. A spanning section (described below) may interconnect displacement portion 414 and fixation portion 412, extending anteriorly and medially from the fixation portion and preferably being curved about an axis generally parallel to the femoral shaft. Fixation portion 412 of implant 400 is used to anchor the implant and displacement portion 414 displaces the tendon. Supplementary fixation 418 may be provided at the opposite end of displacement portion 414 and may also include additional anchoring features like screw holes, spikes etc. In other embodiments, the implant may be anchored on the medial side without a substantial change other than mirroring.

FIGS. 11 and 12 depict implants 420 and 430 with the fixation portions 422 and 432 that are displaced, caudally and cranially respectively, from the tendon-displacing displacement portions 424 and 434. Displacement portions 414, 424 and 434 may be designed to be in contact with the underlying bone or could be partially or wholly elevated so as to avoid contact with the underlying bone, thereby not disrupting the periosteal layer. Implants 420 and 430 also may have supplemental fixation 418, which may also include additional anchoring features like screw holes, spikes etc. In some embodiments, the implant is anchored only on one side (medial or lateral), thereby allowing the implantation procedure to be performed by a single incision. In other embodiments, when supplemental fixation 418 is employed, the opposite side may also be anchored using a percutaneous technique, for example, by using a percutaneous screw.

As with other embodiments described herein, the displacement of the target tissue can be altered by changing the length, curvature and angle of the spanning section and/or dimensions of the displacement and fixation portions as appropriate for specific patient anatomy. Displacement portions 414, 424 and 434 may be configured to move the tendon anteriorly or medially or anterior-medially or laterally or antero-laterally. This may be accomplished by making one side (lateral or medial) of the displacement surface higher than the other, and/or by forming a track with ridges on one or both sides of the bearing surface to urge the tendon in a lateral or medial direction. The inferior region of the displacement portions may be contoured or concave to substantially conform to the curved anterior surface of the femur. The superior surface or the bearing surface on the displacement portion also may be contoured to have a curved convex surface in contact with the target soft tissue. For example, the cross-sectional view of the displacement portion may look like a semi-circle or a semi ellipse (FIGS. 5A-D).

The displacement portion 424 and 434 may be generally orthogonal with respect to fixation portion 422 and 432. The connecting spanning sections 426 and 436 could extend at an angle medially and anteriorly from fixation portions 422 and 432. The spanning section extends the displacement portion out anteriorly to achieve the necessary displacement. The spanning section may also extend more caudally or posteriorly to the displacement section to avoid any connective tissue attachment points. The spanning sections may also comprise adjustable mechanisms (e.g. a pin or hinge) to movably or pivotably alter the orientation or angle between the two parts to achieve the appropriate level of tissue displacement; exemplary embodiments of which are described herein below. The width of the displacement portions 414, 424 and 434 may range from about 10 mm to 40 mm, more specifically about 15 mm to 35 mm, and in some embodiments about 20 mm to 30 mm. The length of the displacement region would typically substantially cover the width of the femoral shaft. Overall depth (D) in exemplary embodiments of implants 400, 420 and 430, in this case as measured from an outer most surface of the displacement portion to the mid-line of the fixation portion passing through at least one screw hole or fixation element would be in the range of about 10-45 mm, to achieve displacements as described herein for average patient anatomy.

Figure 13:
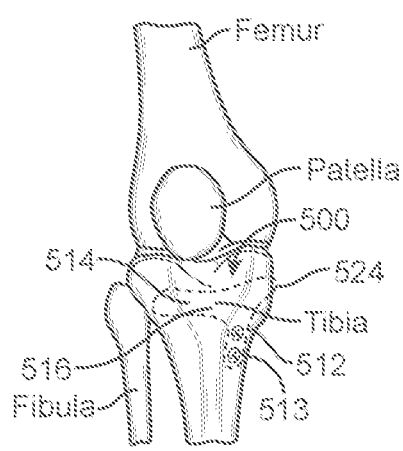
FIG. 13 is an anterior view of a right knee illustrating positioning of another exemplary embodiment of the present invention for treating patellofemoral osteoarthritis and lateral compartment osteoarthritis.
Figure 14:
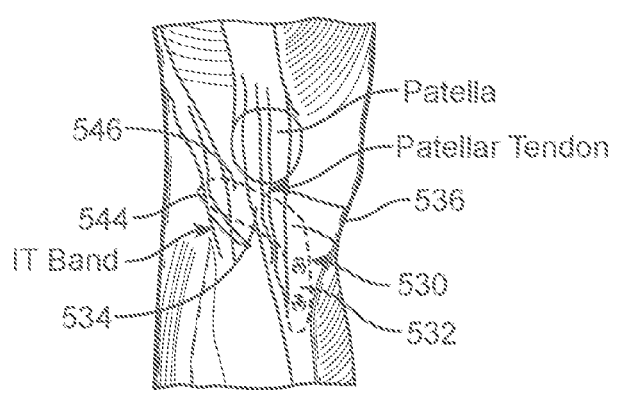
FIG. 14 is an anterior view of a right knee illustrating positioning of another exemplary embodiment of the present invention for treating patellofemoral osteoarthritis and medial compartment osteoarthritis.
Figure 15:
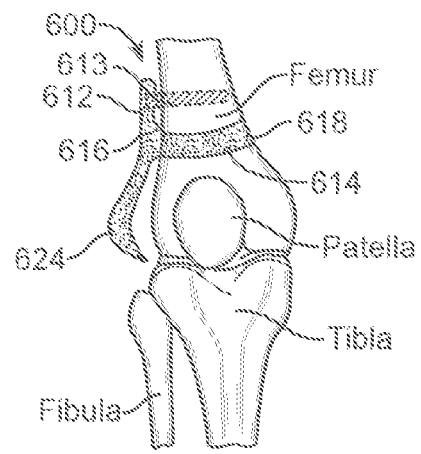
FIG. 15 is an anterior view of a right knee illustrating positioning of another exemplary embodiment of the present invention for treating patellofemoral osteoarthritis and medial compartment osteoarthritis.
Figure 16:
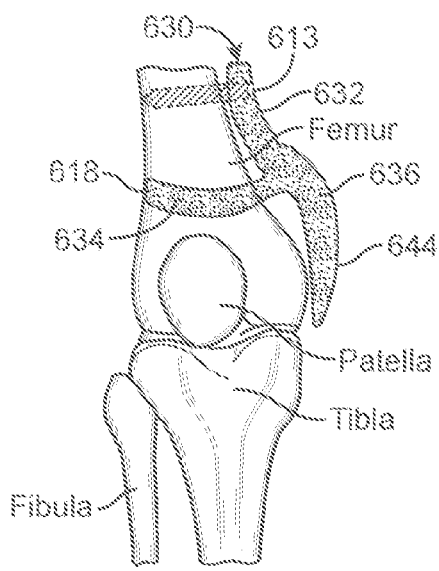
FIG. 16 is an anterior view of a right knee illustrating positioning of another exemplary embodiment of the present invention for treating patellofemoral osteoarthritis and lateral compartment osteoarthritis.

In other embodiments of the present invention, an apparatus for treating dual compartment osteoarthritis of the knee are disclosed. For example, embodiments of the present invention may be configured to treat medial and patellofemoral osteoarthritis, or lateral and patellofemoral osteoarthritis. FIGS. 13 and 14 depict exemplary embodiments of tibial implants 500 and 530 to treat dual compartment osteoarthritis. FIGS. 15 and 16 depict exemplary embodiments of femoral implants 600 and 630 to treat dual compartment osteoarthritis. These embodiments are alternatives to placing separate implants, also disclosed herein, to treat dual compartment osteoarthritis. The dimensions of the implants for treating dual compartment osteoarthritis would preferably be similar to the dimensions of the implants to treat single compartment osteoarthritis described in connection with exemplary embodiments of the present invention discussed herein. The fixation portion of a dual compartment treatment implant may be subject to higher mechanical forces compared to single compartment treatment implants. To withstand the higher mechanical loads, the fixation portion may preferably be thicker, wider or longer as may be selected by a person skilled in the art based on the teachings contained herein.

In FIG. 13, fixation portion 512 is used to anchor implant 500 on the tibia, anterior displacement portion 514 displaces the patellar tendon and medial displacement portion 524 displaces the medial sartorius and/or gracilis tendon. Implant 500 in this exemplary embodiment has a spanning section 516 having a y-shaped or broadened upper end connecting fixation portion 512 and displacement portions 514 and 524 to the fixation portion 512. The displacement of the target tissue can be altered by changing the thickness, length, curvature and angle of the spanning section and/or displacement portion, or other aspects as previously described. The inferior edge of spanning section 516 can also be curved to minimize or eliminate any contact with the medial edge of the patellar tendon. The superior surface edge of the displacement portion 514 can be contoured to allow for easy motion of the patellar tendon during flexion as well as to vary the displacement of the patellar tendon during flexion. In one exemplary embodiment, the anterior displacement portion 514, extending laterally from the spanning section 516, is substantially parallel to the tibial plateau. Spanning section 516 would also be configured to transition from fixation portion 512 by curving around the tibia cranially, medially and dorsally to medial displacement portion 524. Medial displacement portion 524 is configured to for positioning between the sartorius or gracilis tendons and the medial side of the tibia so as to displace these tendons medially or antero-medially. The fixation portion could be attached to the tibia adjacent to the attachment point of the patellar tendon and the tibia or it could be located more cranial or caudal to the attachment point.

In FIG. 14, fixation portion 532 is used to anchor implant 530 on the tibia and displacement portion 534 displaces the patellar tendon while displacement portion 544 displaces the lateral IT Band. The implant in this exemplary embodiment has a fixation portion 532 configured for attachment to the tibia medially of the patellar tendon, with a first spanning section 536 connecting the fixation portion 532 and the patellar displacement portion 534, and a second spanning section 546 connecting the patellar displacement portion 534 and lateral displacement portion 544. The displacement of the tissue can be altered by changing the thickness, length, curvature and angle of the spanning sections and/or displacement portions, or other aspects of the device as described herein. The inferior edge of spanning section 536 can also be curved to minimize or eliminate any contact with the medial edge of the patellar tendon. The superior surface edge of displacement portion 544 can be contoured to allow for easy motion of the patellar tendon during flexion as well as to vary the displacement of the patellar tendon during flexion. In one exemplary embodiment, lateral displacement portion 544, extending laterally and dorsally from the spanning section, is substantially parallel to the tibial plateau. Lateral displacement portion 544 is configured for positioning between the IT band and the tibia just cranial to the insertion point of the IT band in the tibia. Spanning section 546 may be configured to transition from the patellar displacement portion 534 which could be substantially parallel to the tibial plateau to lateral displacement portion 544 configured to displace the iliotibial band laterally or antero-laterally. In exemplary embodiments, spanning sections 536, 546 along with displacement portions 534, 544 form a generally continuous curve about an axis parallel to the tibial shaft such that the implant conforms to the curvature of the outer surface of the tibia. The fixation portion 532 could be attached to the tibia adjacent to the attachment point of the patellar tendon and the tibia or it could be located more cranial or caudal to the attachment point.

In FIG. 15, fixation portion 612 is used to anchor implant 600 onto a lateral aspect of the femur, first displacement portion 614 displaces the quadriceps-femoris tendon and second displacement portion 624 displaces the lateral IT Band. Supplementary fixation 618 also may be provided at the far end of displacement portion 614 and may also include additional anchoring features like screw holes, spikes etc. In some embodiments, the implant is anchored only on the lateral side of the femur, thereby allowing the implantation procedure to be performed by a single incision. In other embodiments, the opposite side may also be anchored with supplementary fixation 618 using a percutaneous technique, for example, by using a percutaneous screw. Fixation portion 612 is generally elongated and configured to be oriented in a direction generally parallel to the femoral shaft, with screw holes extending through it in a medial-lateral direction. The displacement of the target tissue can be altered by changing the thickness, length, curvature and angle of the spanning section and/or displacement sections and other aspects of the device as described herein. First displacement portion 614 may be configured to move the tendon anteriorly or medially or anterior-medially or laterally or antero-laterally. This may be accomplished by making one side (lateral or medial) of the displacement surface higher than the other, and/or by forming a track with ridges on one or both sides of the bearing surface to urge the tendon in a lateral or medial direction. The inferior region of the displacement portions may be contoured to substantially conform to the curved anterior surface of the femur. First displacement portion 614 also may be designed to be in contact with the underlying bone or could be elevated so as to avoid contact with the underlying bone, thereby not disrupting the periosteal layer. The spanning section 616 may have a general y-shape and be configured such that first displacement portion 614 is generally orthogonal the fixation portion 612. One arm of y-shaped spanning section 616 could extend at an angle medially and anteriorly from fixation portion 612 to first displacement portion 614. The spanning section may cantilever or suspend the displacement portion 614 in a position anteriorly spaced apart from the surface of the femur, to achieve the necessary displacement. This arm of the spanning section may also extend more caudally or posteriorly from the fixation portion 612 to first displacement portion 614 to avoid any connective tissue attachment points. In some embodiments, the implant may have a second arm of the y-shaped spanning section 616 that connects the fixation portion 612 to the second displacement portion 624. The second arm may extend out laterally and caudally such that the displacement portion 624 displaces the target tissue laterally over the lateral facet of the femoral condyle. The second arm also may be configured to position displacement portion 624 under the IT band but laterally spaced apart from the surface of the femur to avoid any connective tissue underneath the displacement section (e.g.; fibular collateral ligament, joint capsule etc.). The spanning sections may also comprise adjustable mechanisms (e.g. a pin or hinge, hydraulic cylinder, or gear mechanism) to movably or pivotably alter the orientation or angle between the two parts to achieve the appropriate level of tissue displacement as described herein below. As shown in FIG. 15, the outer surface of second displacement portion 624 has a convex curvature to provide an atraumatic bearing surface for engagement of the IT band. The shape of the displacement portion may, in some embodiments, mirror the shape of the lateral aspect of the enlarged lower end of the femur.

In FIG. 16, fixation portion 632 is used to anchor implant 630 onto the femur, first displacement portion 634 displaces the quadriceps femoris tendon and second displacement portion 644 displaces the medial sartorius and/or gracilis tendon. This embodiment of implant 630 is generally a mirror-image of implant 600 described above and will share many of the same geometrical and other characteristics previously described, while being adapted for attachment to the medial, rather than lateral, side of the femur. In some embodiments, the implant is anchored only on the medial side of the femur, thereby allowing the implantation procedure to be performed by a single incision. In other embodiments, the opposite side may also be anchored with supplemental fixation 618 using a percutaneous technique, for example, by using a percutaneous screw. The displacement of the target tissue can be altered by changing the thickness, length, curvature and angle of the spanning section and/or displacement portion and other aspects of the implant as described herein. First displacement portion 634 may be configured to move the tendon anteriorly or medially or anterior-medially or laterally or antero-laterally. This may be accomplished by making one side (lateral or medial) of the displacement surface higher than the other, and/or by forming a track with ridges on one or both sides of the hearing surface to urge the tendon in a lateral or medial direction. The inferior region of the displacement sections may be contoured to substantially conform to the curved anterior surface of the femur. First displacement portion 634 also may be designed to be in contact with the underlying bone or could be elevated so as to avoid contact with the underlying bone, thereby not disrupting the periosteal layer. Spanning section 636 may be configured in a general y-shape such that first displacement portion 634 is generally orthogonal the fixation portion 632. The first arm of spanning section 636 may extend at an angle laterally and anteriorly from fixation portion 632. First arm of spanning section 636 extends first displacement portion 634 out anteriorly to achieve the necessary displacement. The spanning section 636 may also extend more caudally or posteriorly from the fixation portion 632 to the first displacement portion 634 to avoid any connective tissue attachment points. In some embodiments, the implant may have a second arm of spanning section 636 that connects the fixation portion 632 to the second displacement portion 644. The second arm may extend out medially and caudally such that the displacement portion 644 displaces the target tissue medially over the medial facet of the femoral condyle. The spanning section second arm also may be configured to hold the displacement portion 644 in a position spaced-apart medially from the femur to avoid any connective tissue underneath the displacement portion (e.g.; tibial collateral ligament, joint capsule etc.). The spanning sections may also comprise adjustable mechanisms (e.g. a pin or hinge) to movably or pivotably alter the orientation or angle between the two parts to achieve the appropriate level of tissue displacement.

Figure 17:
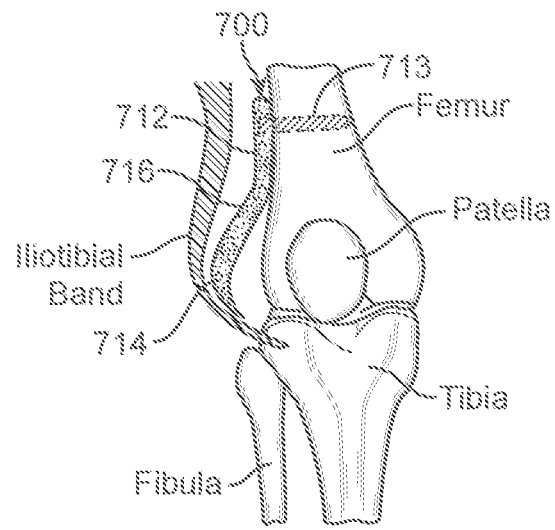
FIG. 17 is an anterior view of a right knee illustrating positioning of another exemplary embodiment of the present invention for treating medial compartment osteoarthritis.

FIGS. 17 and 18 show exemplary embodiments of the present invention for displacement of the iliotibial band. FIG. 17 schematically depicts implant 700 anchored on the lateral side of the femur. Fixation portion 712 of the implant is used to anchor the implant and displacement portion 714 displaces the iliotibial band. The fixation portion and the displacement portion are connected by a spanning section 716 screw or screws 713 in fixation portion 712 secure the implant.

The embodiments of FIGS. 17 and 18 are particularly effective for reducing the load in the medial compartment of the knee joint. The load in the medial compartment is the result of the weight of the person directed caudally through the femur toward the tibia, opposed by an equal and opposite force directed cranially from the ground through the tibia toward the femur. It may be appreciated that the iliotibial (IT) band is attached to the lateral side of the tibial tuberosity at the cranial end of the tibia. The effectiveness of the force exerted by the IT band may be enhanced by increasing the moment arm through which it acts on the joint. Implant 700 displaces the IT band laterally relative to the joint, thus increasing this moment arm and reducing the load in the medial compartment.

FIGS. 18A-D depict an exemplary prototype of implant 700 for treating medial osteoarthritis for the right knee. Fixation portion 712 is configured and dimensioned for attachment of the implant to the lateral side of the distal femur. The implant may be attached with screws positioned in the screw holes 715. Displacement portion 714, the region for displacing the IT band, is connected to fixation portion 712 through spanning section 716. The displacement of the tissue can be altered by changing the length, shape, and angle of the spanning section 716, the shape, thickness and orientation of displacement portion 714, and other aspects of the implant as described herein.

In this exemplary embodiment, fixation portion 712 comprises a generally elongated section of the implant configured to be oriented along the longitudinal axis of the femoral shaft. An inner surface of fixation portion 712 has a concave curvature about its longitudinal axis generally matching that of the outer surface of the femur to maximize surface contact between fixation portion 712 and the underlying bone. Screw holes 715 extend through fixation portion 712 such that screws may be inserted through them in a medial direction into the femur. Displacement portion 714 is preferably separated or offset horizontally (i.e. cranially, caudally, laterally or medially) from fixation portion 712. In the embodiment illustrated, spanning section 716 extends laterally and caudally from fixation portion 712 to displacement portion 714. Displacement portion 714 is attached along its proximal edge to spanning section 716, with its opposing distal edge being a free end. In this way implant 700 may be fixed to the bone only at its proximal end where fixation portion 712 is located, while remaining unattached to the bone at its free distal end where displacement portion 714 is located. Of course, in some embodiments implant 700 may have one or more additional fixation portions, e.g. attached to the distal, ventral, or dorsal edges of displacement portion 714, such that implant 700 may be secured to the bone at both ends or along its edges.

Displacement portion 714 preferably has an enlarged spoon-like rounded shape similar to the lateral profile of the lower end of the femur. In preferred embodiments, fixation portion 712 has a length $L_A$ (FIG. 18B) selected to extend longitudinally along the femur sufficiently to stabilize the implant and to accommodate the desired number of hole(s) to receive screws for anchoring to the femur. In preferred embodiments length $L_A$ may be 25-65 mm, more preferably 30-60 mm, and most preferably 35-55. The combined length $L_A$ of the spanning section 716 and displacement portion 714 will be selected to position the displacement portion under the IT band laterally of the distal end of the femur, with the distal (caudal) end 721 of displacement portion 714 being at the level of the gap between in the femur and the tibia. Displacement portion 714 preferably has a convex curvature on its outer or lateral side, and a concave curvature on its inner side. Displacement portion 714 has an outer bearing surface 730 which engages the IT band. The bearing surface 730 is smooth, rounded and low-friction to minimize wear and trauma to the IT band. In preferred embodiments, bearing surface 730 is free of significant ridges, bumps, voids, holes or other discontinuities of the kind that would cause abrasion or wear of the target tissue, particularly larger holes or channels for fixation devices such as screws or K-wires. Bearing surface 730 may comprise simply a smoothed and/or polished region of displacement portion 714, or it may comprise a coating or layer of a different material, e.g. a lubricous biocompatible polymer. In other embodiments, bearing surface 730 may have holes, protuberances, a polymeric or drug coating, or other features to promote adhesion with the displaced target tissue such that movement between the target tissue and implant 700 is minimized.

Preferably the inner and outer surfaces have curvature about multiple axes, and may be generally or partially spherical. The radius of curvature $R_A$ of the outer surface, shown in FIG. 18C, is selected to provide the optimal displacement of the IT band throughout the range of motion of the knee. In some embodiments the shape and curvature of the outer surface will be selected such that the IT band is under a substantially constant magnitude of displacement throughout the range of knee motion, while in other embodiments, the shape and curvature of the outer surface will be selected to displace the tissue more in certain portions of the range of motion, while reducing the displacement in other regions of the range of motion. Curvature $R_A$ of the outer surface of displacement portion 714 is usually about 15-35 mm, more preferably 20-30 mm, and most preferably 23-27 mm.

Displacement portion 714 may be cantilevered or suspended by spanning section 716 in a plane laterally displaced from or angled relative to fixation portion 712 such that it is spaced apart from the lateral surface of the femur when the implant is fixed in its implanted position. This provides space between the femur and the displacement portion through which non-target soft tissues may reside and/or move without interference. In a preferred embodiment, spanning section 716 extends laterally and caudally at an oblique angle relative to fixation portion 712 such that a plane P tangent to the surface of the spanning segment 716 is disposed at an angle θ relative to a centerline C through fixation portion 712 of between 30-60° more preferably 35-55°, and most preferably 42-48°.

Spanning section 716 may be substantially rigid such that displacement portion 714 remains stationary relative to the femur under the loads exerted by the IT band. Alternatively, spanning section 716 and/or displacement portion 714 may have some degree of flexibility so as to allow some movement of displacement portion 714 relative to the femur under certain loads. For example, spanning section 716 may have a flexibility selected such that if loads on displacement portion 714 exceed a preselected threshold, spanning section 716 will flex to allow displacement portion 714 to be deflected relative to the femur.

The anterior edge 705 of the implant is preferably curved (Radius of curvature $R_B$ in FIG. 18B) to avoid contact with the lateral edge of the patella. The posterior edge 706 of the implant is also preferably curved (Radius of curvature $R_c$ in FIG. 18B) to avoid contact with the fibular head during knee flexion. In some embodiments, the distal, anterior and posterior edges of the displacement section 714 are shaped to form an arc (Radii of curvature $R_B$, $R_c$ and $R_D$ in FIG. 18B) similar to the lateral profile of the distal end of the femur viewed in the sagittal plane. In some embodiments, the distal, anterior and posterior edges of the displacement section 714 are shaped to form an arc (Radii of curvature $R_x$, $R_y$ and $R_z$ in FIG. 18D) viewed in the transverse plane. The anterior edge 705 may also be shaped to minimize displacement (anteriorly or laterally) of the lateral edge of the quadriceps-femoris tendon/muscle. Alternatively, anterior edge 705 may be shaped to extend under the quadriceps-femoris tendon to anteriorialize or lateralize the lateral edge of the quadriceps-femoris tendon/muscle. The posterior edge 706 may be shaped to minimize displacing the IT Band during high flexion. The posterior edge may also be extended posteriorly such that the anterior edge of the IT Band remains on the implant surface during high flexion. The inside surface 721 of the displacement portion 714 is preferably concave with a spoon-like shape to minimize contact with underlying soft tissue including lateral ligaments, the joint capsule, etc. In one exemplary embodiment as shown, the fixation portion 712 is tapered from the distal (or caudal) end to the proximal (or cranial) end. In other embodiments, the fixation portion 712 may have constant width. In the exemplary embodiment as shown, the width of the displacement portion 714 is substantially larger than the width of fixation portion 712, contributing to the overall spoon-like or paddle-like shape of implant 700. Displacement portion 714 is once again joined to fixation portion 712 by a spanning section 716.

The curvature of the displacement portion 714 may be configured to displace the target tissue, e.g. the iliotibial band, laterally or antero-laterally. In some embodiments, the anterior region of the displacement portion 714 may extend out more laterally than the posterior region of the displacement section. In one exemplary embodiment, the implant is placed on the lateral side of the distal femur such that fixation portion 712 is substantially aligned with the femoral shaft, the spanning section 716 is in close apposition to the region of the femur where the femoral shaft joins the femoral condyle, and the displacing portion 714 substantially covers or lies generally parallel to the lateral facet of the femoral condyle. In some embodiments, the top view of the implant would mirror the lateral view of the distal femur, wherein the implant has shaft region similar to the femoral shaft, an expanding neck region similar to the condylar flare and a circular or oval or elliptical region similar to the condyle. Typical dimensions of embodiments of implant 700 (FIGS. 18A-D) would be as follows: $L_A$ about 40 to 55 mm, $L_B$ about 45 to 60 mm, $T_2$ about 2.5 to 5.0 mm, $R_A$ about 23 to 27 mm, $R_B$ about 12 to 18 mm, $R_C$ about 12 to 18 mm, $R_C$ about 25 to 33 mm, θ about 40 to 50°, $W_1$ about 12 to 18 mm, $W_2$ about 45 to 60 mm, D about 10 to 45 mm, $R_X$ about 35 to 40 mm, $R_Y$ about 20 to 25 mm, $R_Z$ about 27 to 33 mm, X about 40 to 50°, Y about 20 to 30° and Z about 25 to 35°. In exemplary embodiments, the size of the implant (as seen in the top view) would be proportionally smaller than the lateral profile of the femoral condyle, preferably 1-40% smaller, more preferably 5-25% smaller, and most preferably 10-20% smaller.

Example

An exemplary embodiment of the present invention as shown in FIGS. 18A-D was subjected to simulated load testing. Dimensions of the implant tested were: $W_1$=23 mm, $W_2$=50 mm, $L_A$=35 mm, $L_B$=40 mm, D=30 mm. The test was conducted as follows: Using a robotic testing system for evaluating knee joint biomechanics, as described by Gadikota et al., American Journal of Sports Medicine, 38, 713-720, 2010, simulations were run using cadaveric human knee specimens. Eight fresh-frozen cadaveric human knee specimens (4 male, 4 female, Age: 36-50 y) stored at −20° C. were thawed at room temperature prior to testing. The quadriceps muscles were loaded at 300N, the hamstrings at 100N, and the iliotibial band at 0, 50, and 100N to simulate a variety of loading conditions. The displacement of the IT Band ranged from 15 to 20 mm. The robotic testing system was used to determine knee joint kinematics and contact forces in the medial and lateral compartments from 0° to 30° flexion, with and without the exemplary implant (FIG. 18).
Results:
 Average medial compartment load measured from 0° to 30° flexion for the eight specimens was reduced by about 56% at IT Band loading=0N, about 43% at IT Band loading=50N, and about 49% at IT Band loading=100N.
 Average valgus/varus orientation of the knee measured from 0° to 30° flexion for the eight specimens was more valgus by about 0.4° at IT Band loading=0N, about 0.3° at IT Band loading=50N, and about 0.3° at IT Band loading=100N.
 Average internal/external rotation of the knee measured from 0° to 30° flexion for the eight specimens was more externally rotated by about 0.4° at IT Band loading=0N, substantially unchanged at IT Band loading=50N and more internally rotated by about 0.2° with the IT Band=100N.

These results show that lateral displacement of the IT Band in the range disclosed in the present invention results in decrease in articular cartilage loading in the target knee compartment (medial). The experimental results further show that displacing the IT Band with a prosthesis described in the present invention alters the kinematics of the target joint.

Figure 19:
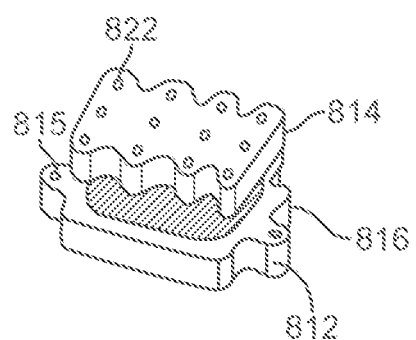
FIG. 19 is a schematic perspective view of an embodiment of the present invention incorporating an adjustable capsule between two solid members.
Figure 20:
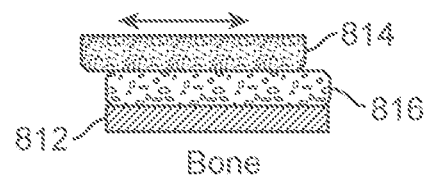
FIG. 20 is a schematic cross sectional view of an embodiment of the present invention incorporating an adjustable capsule between two solid members.

FIGS. 19 and 20 depict portions of further exemplary implants according to the present invention and optional features thereof. In one alternative, the fixation portion comprises a base plate 812 that can be attached to the underlying bone with screws through holes such as holes 815. Upper plate 814 comprises the displacement portion and may be attached to target tissue with sutures, adhesives, tissue in-growth etc. For example, in FIG. 19, holes 822 are provided for suturing. Alternatively, the upper plate may have surface features like increased roughness, beads etc. as previously describe that minimize slippage between the connective tissue that lies over the plate and the plate itself. The plates may be fabricated from metal or polymeric substrate. A capsule 816, acting as a spanning section, joins upper plate to base plate and allows relative motion between plates. There is little or no relative motion between the displaced soft tissue and implant surface and no relative motion between the bone and the implant surface. With little or no motion between the soft tissue and top plate, wear concerns are minimized. In some embodiments, motion may be along all three axes as well as rotational. The sealed capsule may be fabricated from an inelastic material or a stretchable or deformable material (such as silicone, polyurethane etc.) which is attached to the plates. The capsule may be filled with gel, saline, balls, beads etc. Alternatively, a capsule may enclose the entire construct, thereby eliminating any contact between the plates and the surrounding tissue. A sealed capsule would isolate the moving surfaces from biological interference (scar tissue, fibrotic coverings, encapsulation, clotting etc.).

In a further alternative, material may be added to or removed from capsule 816 to adjust the distance between the plates. As shown in an exemplary embodiment in FIG. 21, capsule 816 may have separate chambers to selectively alter the displacement of the plates. Each chamber 816a-c preferably has its own injection port or valve (not shown) through which a liquid or gaseous filler material may be introduced. Chambers 816a-c may have different volumes, and may be filled with different or identical fillers. The volume of material in each chamber may be changed post-implant as needed to optimize treatment. For example, if the soft tissue being displaced stretches or moves over time, material may be added or removed from each chamber to maintain the desired degree and direction of displacement.

In other embodiments, the capsule 816 may be replaced by an elastomeric or sponge like material which can be assembled in multiple layers to vary the displacement between the plates. Alternatively one or more springs may interconnect the two plates.

Exemplary device shown in FIGS. 19 and 20 may also be used for diagnostic purposes. The device may be implanted in humans, cadaveric tissues or in animal models, and the plates could be visualized via fluoroscopy or other imaging techniques. Visualization of the plates during flexion/extension or other joint motion would help understand the complex relationship between the soft tissue and underlying bone during joint motion, thereby enabling design of implants with better therapeutic or safety features.

FIG. 22 depicts a portion of a further alternative exemplary implant of the present invention with features in common with the implants shown in FIGS. 19 and 20. In this embodiment base plate 812 is attached to the underlying bone with screws etc. and the upper plate 814 is attached to soft tissue as previously described. Again, the plates may be fabricated from metal or polymeric substrate. The upper plate and lower plates are supported by a mechanical coupling 825 that allows motion there between. Coupling 825 allows motion in multiple directions and could also be adjusted to alter the distance between the two plates. The mechanical coupling may be encased in a capsule to isolate the mechanism from scar tissue formation etc. There would be motion between the top plate and the base implant, but little or no motion between the soft tissue and top plate, thereby minimizing wear concerns. The mechanical coupling may be fabricated from metal or polymeric substrates. In some embodiments, motion may be provided for along all three axes as well as rotational. In other embodiments, the bottom plate may comprise a further spanning section and a fixation section such that the displacement section is not in contact with bone. For example, the exemplary embodiments shown in FIGS. 19, 20, 21 and 22 could be configured to be attached to or mounted on the displacement region 214 (FIG. 7), 314 (FIG. 9), 414 (FIG. 10), 424 (FIG. 11), 434 (FIG. 12), 614 (FIG. 15), 624 (FIG. 15), 634 (FIG. 16), 644 (FIG. 16), 714 (FIG. 17) etc. The device may also be used for diagnostic purposes as described above.

One exemplary implant employing features as shown in FIGS. 19-21 is shown in FIG. 23. In this embodiment implant 830 includes a displacement portion 814 which is in contact with the IT Band. Base plate 812 comprises the fixation portion and is secured to the bone via screws 813. Capsule 816 forms a moveable spanning section between the two plates, allowing the plates to move relative to one another. This permits relative motions between the IT band and the femur while avoiding friction or wear due to movement of the IT band over the implant.

Another exemplary embodiment with a capsule is shown in FIG. 24. Fixation portion 852 of implant 850 is configured to be attached to bone. This embodiment may have a configuration adapted for attachment to the lateral femur and displacement of the IT band like that described above in connection with FIGS. 18A-C, and may have a similar geometry. Displacement portion 854 may be in contact with the underlying bone or soft tissue like ligaments etc. or it may be spaced apart from the underlying tissue (to provide space for e.g.; collateral ligaments, joint capsule etc.). In this embodiment, a separate bearing member 857 forms the top plate as previously described with a capsule 855 interposed between the bearing member and bottom plate of the displacement portion. The spanning section 856 may be configured to alter the position of the displacement portion 854 relative to the fixation portion 852. The displacement portion 854 may lie generally in a plane parallel to that in which the fixation portion 852 lies, and the spanning section 856 may extend at an angle or be curved laterally and caudally from fixation portion. In other embodiments, the implant may be anchored on the medial side of the femur and the spanning section may extend at an angle medially and caudally from the fixation portion.

Figure 25:
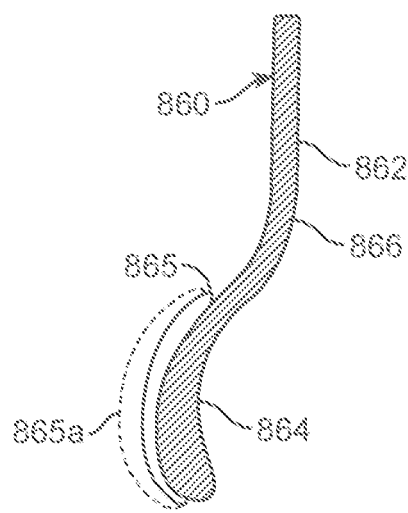

FIG. 25 depicts a further alternative exemplary implant 860 according to the present invention. Fixation portion 862 is configured to be attached to bone. Displacement portion 864 includes a sealed capsule 865, attached to a side opposite the bone. The sealed capsule could be fabricated with an inelastic or stretchable or deformable material (such as silicone, polyurethane etc.). The capsule will preferably have an inlet port or valve (not shown) through which it may be filled with air, gas, water, gel, saline, metal or polymer balls, beads etc. Solidifying materials such as two-part epoxies may also be used as fillers. The capsule 865 could be inflated to an expanded shape (indicated by dashed lines 865a) by addition of the filler as required to achieve the necessary tissue displacement. Displacement portion 864 may be in contact with the underlying bone or soft tissue like ligaments etc. or it may be displaced from the underlying tissue (for e.g.; collateral ligaments, joint capsule etc.). The spanning section 866 may be configured to alter the position of the displacement portion 864 relative to the fixation portion 862. The displacement portion 864 may lie in a plane generally parallel with a plane containing the fixation portion 862, and the spanning section 866 may extend at an angle or be curved laterally and caudally from fixation portion. In other embodiments, the implant may be anchored on the medial side of the femur and the spanning section may extend at an angle medially and caudally from the fixation portion.

Figure 26:
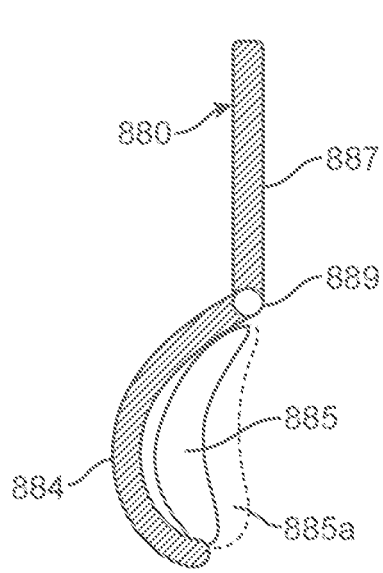

FIG. 26 depicts another alternative exemplary implant 800 according to the present invention. Fixation portion 882 of implant 880 is configured to be attached to bone. Displacement portion 884 has a capsule 885, attached to an inner surface of the implant, facing the bone. The fixation portion and displacement portion are movably or pivotably interconnected with an adjustable attachment 889, e.g. a pin or hinge. The orientation or angle between the two parts can be altered to achieve the appropriate level of tissue displacement. The capsule 885 will have an inlet port or valve (not shown) through which it may be filled with air, gas, water, gel, saline, balls, beads etc. The capsule 885 could be inflated to an expanded state (indicated by dashed line 885a) by addition of material as required to achieve the necessary tissue displacement. The adjustable attachment 889 could be locked in the final position once the soft tissue has been displaced appropriately. Alternatively, the adjustable attachment may include a one-way mechanism like a ratchet mechanism.

In some embodiments, the capsule, for example capsules 865 or 885, may have multiple chambers that could be inflated independently. The surface of the capsule could be modified as needed for interaction with the soft/hard tissue. For example, the surface could be smooth to allow for easy movement of the soft tissue across the surface. Alternatively, the surface may have an adhesive surface to allow attachment to underlying bone or soft tissue. The surface could be coated with a hydrophilic or hydrophobic layer. The surface may have a polymeric coating for drug release. Drugs like anti-inflammatory drugs and antibiotics could be incorporated into the polymeric coating. The capsule may be filled with a liquid or gas under suitable pressure to allow adjustment of the bearing member position and associated displacement of the target tissue. The bladder will have an inflation port for introduction of inflation fluid by means of an inflation device, which may be similar to the inflation devices used for inflation of angioplasty balloons as will be understood by persons of ordinary skill in the art.

In some embodiments of the present invention, the displacement of the connective tissue could be adjusted by adjusting the device pre-operatively, intra-operatively or post-operatively. Devices may include mechanisms that are remotely controlled and/or enable wireless communication to alter the displacement after implantation. Alternatively, the displacement may be adjusted by applying an energy fields (e.g.; magnetic field, electric field, thermal field etc.) transdermally from an external location.

In various adjustable embodiments described above, the adjustment mechanisms themselves may be radiopaque and/or otherwise discernable from the rest of the implant under x-ray in order to enable post-surgical percutaneous adjustment of the device. Alternatively, target features can be built into the device to locate the adjustment points without having the screws or adjustment means themselves radiopaque, such as radiopaque rings or markers built into the nearing surface of the device itself.

The implants described above may be implanted in areas adjacent to the joint such that the soft tissue is displaced in a region it crosses the joint. Alternatively, the device could be implanted away from the joint and displace the target soft tissue in a region that it is not crossing the joint. For example, the device could be implanted distally on the lateral femur close to the lateral femoral condyle to displace the IT Band as it crosses the joint or the device could be implanted more proximally along the femoral shaft where it displaces the IT Band in a region away from the joint (FIG. 23). Similarly, the device could be implant further up along the femoral shaft where it displaces the sartorius and gracilis muscle in a region away from the joint.

Figure 27:
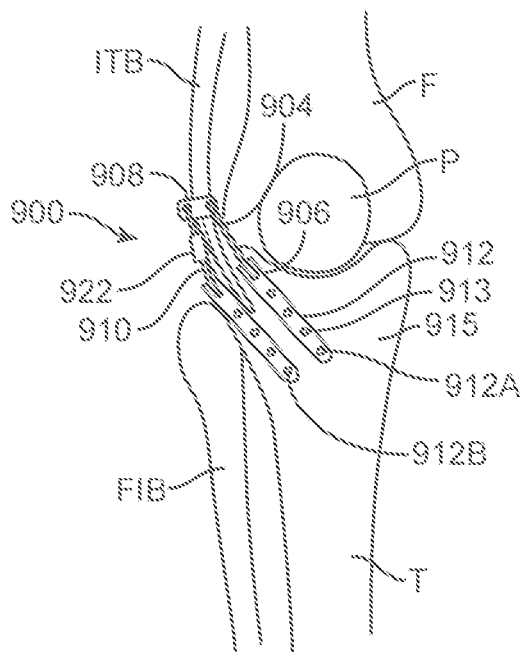
FIG. 27 is an anterior view of a right knee illustrating positioning of an alternative exemplary embodiment of the present invention for treating medial osteoarthritis with an adjustable tensioning device.

Embodiments of the present invention may also be configured to displace tissue by pulling the tissue away from the joint to increase the moment arm, rather than pushing it away as in some other embodiments. One exemplary embodiment of such a device is shown in FIG. 27. In this embodiment, apparatus 900 comprises fixation portion 912, here comprising separate anchors 912A, 912B configured for mounting to the lateral aspect of the tibia T. Each anchor member 912A, 912B has a plurality of holes 915 to accommodate anchoring screws 913. A generally rigid pivoting arm 904 is pivotably coupled to first anchor 912A so as to be movable rotationally about pivot point 906. The cranial end of pivoting arm 904 is pivotably mounted to a tissue hook 908 which is configured to at least partially encircle iliotibial band ITB. An adjustment arm 910 is pivotably mounted to second anchor 912B on its caudal end and to tissue hook 908 on its cranial end. Adjustment arm 910 has an axial length adjuster 922 coupled thereto, which in an exemplary embodiment may comprise a threaded tube into which two opposing segments of adjustment arm 910 are threaded with opposite handed threads. In this way the length of adjustment arm 910 may be shortened or lengthened. It may be seen that as adjustment arm 910 is shortened it pulls on tissue hook 908, which pivots laterally on pivoting arm 904. This displaces iliotibial band ITB laterally, away from the center of the knee, thus lengthening the moment arm of the force exerted on the joint by iliotibial ITB and moving the resultant force vector in the lateral direction, reducing the force in the medial compartment of the joint. In this embodiment tissue hook 908 forms a displacement portion and adjustment arms 910 a spanning section.

It will be appreciated that anchors 912A-B may have a shape selected to allow secure anchoring to the bone and to avoid soft tissues and bony features on the tibia. In addition the various components of apparatus 900 will be configured to minimize engagement with and abrasion of the soft tissues surrounding the joint, without sharp edges or catch points. Apparatus 900 may optionally be covered or coated with a soft or friction-reducing material.

The apparatus of FIG. 27 may alternatively be configured for attachment to the medial side of the tibia to displace the Sartorius muscle or tendon, the Gracilis muscle or tendon, or other suitable tissues for the treatment of lateral osteoarthritis. Moreover, apparatus 900 may be configured for mounting to the fibula FIB instead of or in addition to the tibia. Further, apparatus 900 may be configured for mounting to the femur F in an upside down orientation relative to that depicted in FIG. 17.

Figure 28:
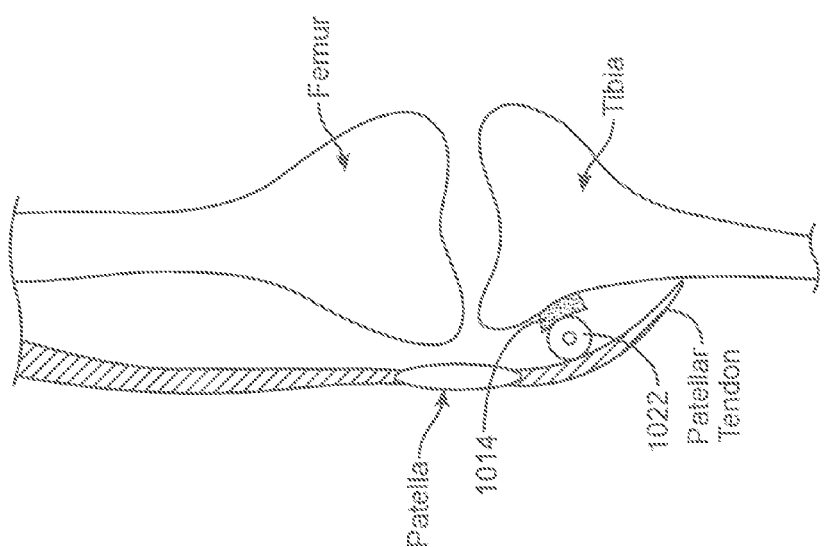

In another alternative embodiment shown in FIG. 28, implant 1000 may include a displacement portion 1014 with a roller or rollers embedded in it or mounted on it to ease the motion of the patellar tendon across the implant surface during flexion/extension and reduce any wear due to the motion of tissue across the implant surface. In one embodiment, roller 1022 is embedded in displacement portion 1014 of the implant. The axis of rotation of the roller could be essentially parallel to the tibial plateau axis such that the axis of motion of the patellar tendon is essentially orthogonal to the axis of rotation of the roller. The roller can rotate freely in both directions (clockwise and counter clock-wise). The position or thickness of the displacement portion 1014 and the diameter of the roller 1022 can be adjusted to obtain the necessary amount of anterior displacement of the patellar tendon. Displacement portion 1014 may otherwise cooperate with a fixation portion and a spanning section as previously described.

Figure 29:
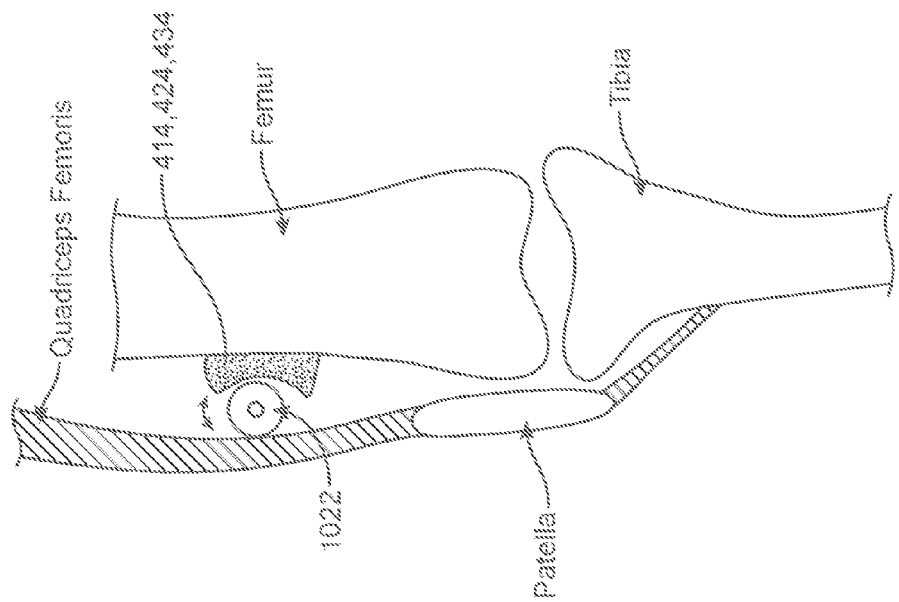
FIGS. 28 and 29 are schematic side views of a human knee with prostheses according to embodiments of the present invention, including at least a roller in the displacement portion of the prostheses.

In other alternative embodiments, displacement portions of previously described static implants may be provided with a roller or other dynamic feature to further reduce wear or trauma to the displaced tissue. For example, displacement portions 414, 424 or 434 of implants 400, 420 and 430, respectively, may have a roller or rollers 1022 mounted thereon to ease the motion of the quadriceps tendon across the implant surface during flexion/extension and reduce any wear due to the motion of tissue across the implant surface as shown in FIG. 29. The roller 1022 is embedded in the displacement portion of the implant. The axis of rotation of the roller could be essentially parallel to the femoral condyle axis (medial-lateral) such that the axis of motion of the tendon is essentially orthogonal to the axis of rotation of the roller. The roller can rotate freely in both directions (clockwise and counter clock-wise). The thickness of displacement portion and the diameter of the roller can be adjusted along with other aspects of the device as previously described to obtain the necessary amount of anterior displacement of the quadriceps femoris tendon.

Figure 30:
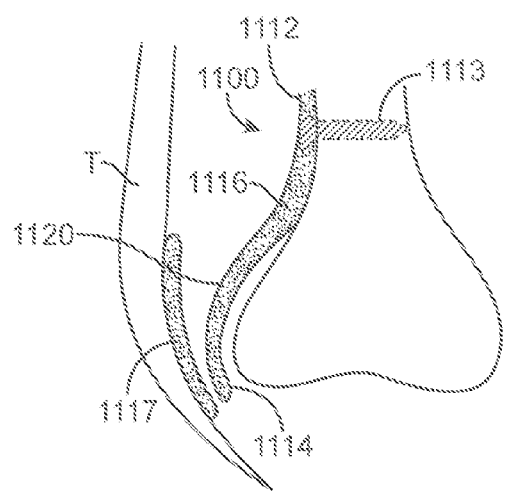
FIG. 30 is an anterior view of the femur of a right knee illustrating positioning of an alternative exemplary embodiment of the present invention for treating medial osteoarthritis with a two piece device.

FIG. 30 depicts an alternative exemplary two piece implant 1100 according to an embodiment of the present invention for treating medial osteoarthritis wherein the two pieces are independent of each other and articulate over each other during joint motion. Fixation portion 1112 of implant 1100 is the fixed section of the implant and is attached to the bone with screw or screws 1113. Displacement portion 1114 includes a mobile bearing member 1117 that bears upon fixed surface 1120 of displacement portion 1114. With this configuration, mobile bearing member 1117 may be attached to the target soft tissue T. Either fixation portion 1112 or displacement portion 1114, or both may have a shape and size selected to displace mobile bearing 1117, and thus tissue T, the desired degree. The two piece design enables articulation between the surfaces of displacement portion 1114 and mobile bearing 1117; and reduces the risk of tissue wear due to motion of soft tissue over the implant surface. Mobile bearing member 1117 may be attached to the soft tissue using sutures, adhesives, pins etc. or otherwise as described above, including having the surface in contact with the soft tissue modified to enable tissue integration. The articulating surfaces between parts 1114 and 1117 also may have features like grooves to enable one surface to track a fixed path during flexion. The surfaces could be coated to minimize friction and wear. In some embodiments, the mobile section is attached to or embedded in the IT Band. In other embodiments, the mobile section may be attached or embedded into the patellar tendon, the quadriceps femoris tendon, or any other soft tissue surrounding the target joint. In some embodiments, bearing member 1117 may comprise of a soft, flexible, polymer membrane which can conform to the soft tissue and prevent contact between the soft tissue and the implant surface 1120. In other embodiments, bearing member 1117 may be inflatable, or include a capsule as previously described.

Figure 31:
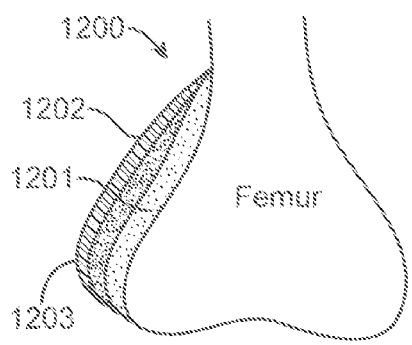
FIG. 31 is an anterior view of the femur of a human knee illustrating positioning of another exemplary embodiment of the present invention for treating medial osteoarthritis with a multi-layered device.
Figure 32:
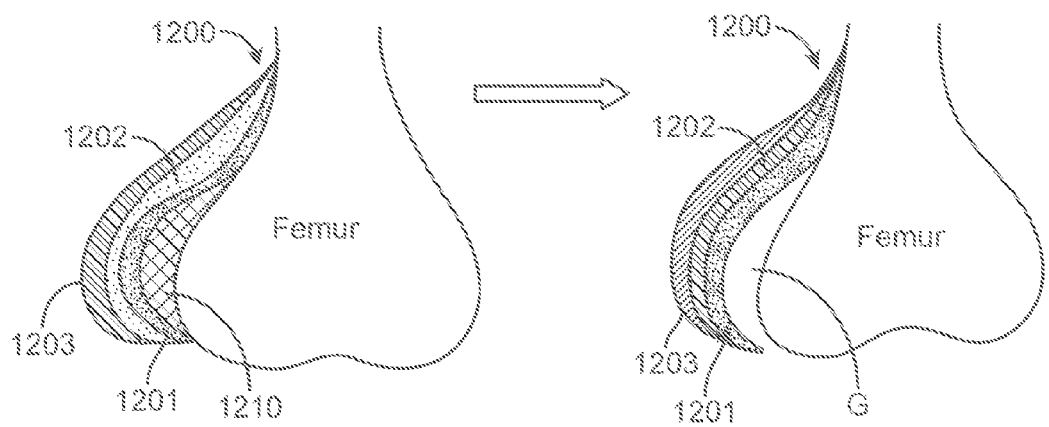
FIG. 32 is an anterior view of the femur of a human knee illustrating positioning of an alternative exemplary embodiment of the present invention for treating medial osteoarthritis with a multi-layered device.

In further alternative embodiments, implants may also be fabricated in-situ by layering a polymerizing material on the underlying tissue such as in the embodiments of FIGS. 31 and 32. In such an embodiment, an implant could be contoured as needed by varying the material being layered in different regions of the implant. Removable molds or forms may be placed through an incision to the desired location against the bone to facilitate containment and shaping of the material prior to solidifying. In one exemplary shown in FIG. 31, implant 1200 includes layers 1201, 1202 and 1203, layered on top of each other to achieve the necessary displacement. The materials and the properties of each of the layers could be identical or different. For example, layer 1201 may have adhesive properties to attach to the underlying bone, layer 1202 may have high compressive strength to withstand the compressive load of the overlying soft tissue and layer 1203 may have a smooth hydrophilic surface to minimize friction between the implant and the soft tissue during flexion/extension. In this example, layer 1201 provides the fixation portion and layer 1203 the displacement portion with layer 1202 forming a spanning section there between. Adhesives may be used between the various layers. The materials could be polymerized in-situ using chemical crosslinkers, photo-initiated crosslinkers, thermally initiated crosslinkers, etc. The thicknesses of the various layers could be altered to achieve the necessary level of tissue displacement.

In an alternative exemplary embodiment of an in situ fabricated implant, as shown in FIG. 32, a spacer 1210 may be used to assist in fabricating the implant. The spacer 1210 could potentially be removed after the implant has been fabricated, leaving behind a gap (G) between section 1201 and the underlying soft tissue and bone. However, the implant may be designed to rest permanently on the underlying soft tissue and bone.

In yet another exemplary embodiment of the present invention, the displacement of the connective tissue may occur at a region away from the joint. For example, as depicted in the exemplary embodiment of FIG. 23, the iliotibial Band is displaced laterally substantially proximally along the femoral shaft with an exemplary device. Similarly, the in-situ fabricated implant could be located such that it displaces the target soft tissue around the target joint or at a site away from the target joint.

A further aspect of the present invention includes methods for treating knee joints and implanting prostheses as described herein. One exemplary method thus comprises selecting at least one of the associated muscle and connective tissues surrounding a joint as target tissue for treatment, displacing the target tissue without severing the bones or target tissue, and altering the kinematics of the joint. In a further embodiment, altering the kinematics of the joint achieves a therapeutic effect. In other embodiments, altering the kinematics of the joint redistributes loading in the joint, and or reduces loading on the ligaments within the joint. In some embodiments prostheses according to the present invention may be placed with therapeutic effect without rupturing the joint capsule.

Figure 33:
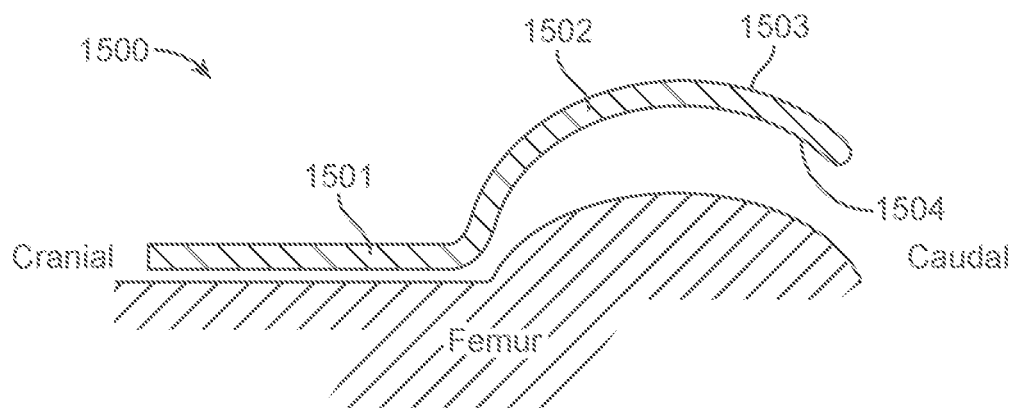
FIGS. 33-43, 45, 47-49 are partial cross-sectional views of the distal femur of a human knee (oriented horizontally) illustrating alternative exemplary embodiments of the present invention.

In some embodiments, the inferior surface of the displacement region is elevated off the underlying tissue. The underlying tissue could be bone or soft tissue like tendon, muscle, ligament, bursa, capsule etc. FIG. 33 depicts an implant 1500 with the inferior surface 1504 of the displacement section 1502 elevated off the underlying tissue. Elevating the inferior surface off the underlying tissue could be beneficial by minimizing interference with or damage to soft tissue, reducing any potential restriction to joint motion due to compression of soft tissue etc.

Elevation of the IT band above the underlying tissue (bone, bursa etc.) by the prostheses disclosed in the present invention may also be effective in alleviating IT band pain.

In some embodiments, the displacement region will have a continuous bearing surface which is in contact with the target connective tissue (muscle, tendon, ligament etc.) and is devoid of any discontinuities. Such discontinuities are usually undesirable as they create voids and interruptions in the smooth bearing surface, may have sharp edges or transitions, and may cause wear or abrasion of the displaced target tissue. Discontinuities would include fixation channels for long-term fixation like screw holes, holes for sutures etc. as well as fixation channels for temporary fixation like holes for Kirschner-wires (K-wires).

FIG. 33 depicts an implant 1500 with a displacement section 1502 with a superior bearing surface 1503 and an inferior surface 1504. Displacement section 1502 is free of discontinuities in the bearing surface, such as holes that extend from the superior bearing surface 1503 to the inferior surface 1504 or those that extend from the superior bearing surface 1503 part way to the inferior surface 1504. The lack of discontinuities in the bearing surface minimizes the potential for wear or irritation of the target connective tissue.

The bearing surface of the displacement section may be polished, coated, covered, or modified in other ways to minimize wear of the bearing surface and/or wear of the target connective tissue.

In some embodiments, the bearing surface of the displacement region which is in contact with the target connective tissue (muscle, tendon, ligament etc.) may have features that enable adhesion or attachment of the target connective tissue to the bearing surface. Attachment of the target connective tissue on the implant surface may minimize motion of the tissue across the implant surface during joint motion. These features would include channels for formation of fibrous tissue from the target connective tissue anchoring the connective tissue to the displacement surface of the implant.

Figure 34:
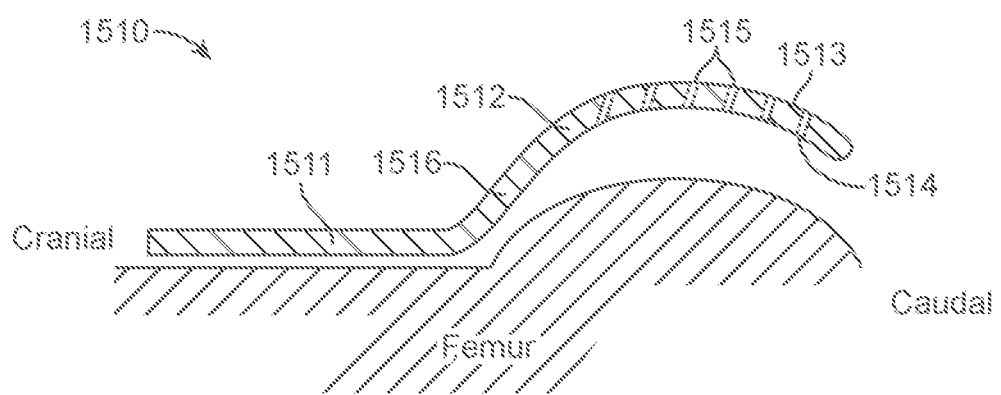
Figure 35:
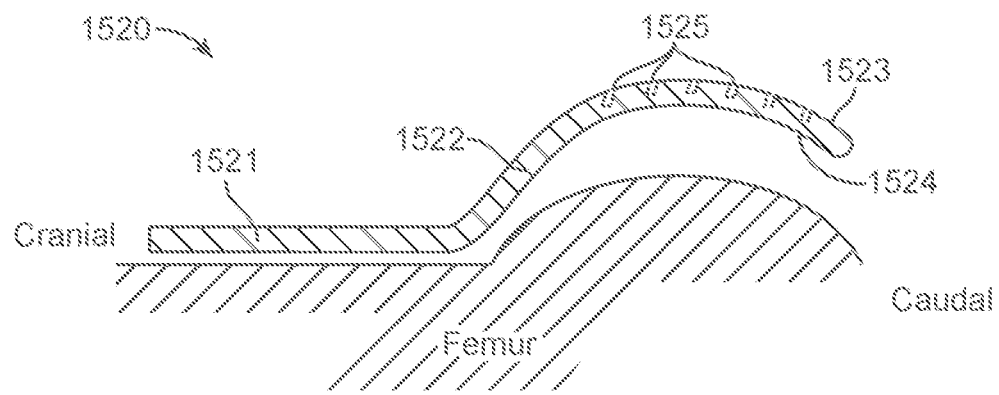

FIG. 34 depicts an implant 1510 with channels 1515 that extend from the superior bearing surface 1513 to the inferior surface 1514. FIG. 35 depicts an implant 1520 with channels 1525 extend from the superior bearing surface 1523 part way to the inferior surface 1524. The channels 1515 and 1525 may have varying cross-sectional shapes, for example; square, circle, rectangle, oval etc., with the largest cross-sectional dimension (for example, diameter of the circle, diagonal of a square or rectangle, major diameter of an oval etc.) and will be dimensioned to promote adhesion and ingrowth of the target tissue, usually ranging from less than 1 mm to about 5 mm. The channels may be located across the entire bearing surface or across part of the bearing surface. In some embodiments, the displacement region may have one channel. In some embodiments, the displacement region may have two channels. In some embodiments, the displacement region may have three channels. In some embodiments, the displacement region may have more than three channels. In some embodiments, the channels may vary in depth across the bearing surface. The dimensions and cross-sectional shape of the channels across the displacement region may be identical or different. In some embodiments, the spanning section (e.g., 1516 and 1526) and/or the fixation section (e.g., 1511 and 1521) may also have similar features for attachment of the target connective tissue. In some embodiments, a region of the displacement section may have features for attachment of target connective tissue.

In some embodiments, the bearing surface of the displacement region may have surface features that enable adhesion or attachment of the target connective tissue to all or part of the bearing surface. These features would include projections, microprojections, bumps, ridges, pin-like projections, a granular surface, a sintered layer, etc.

Figure 36:
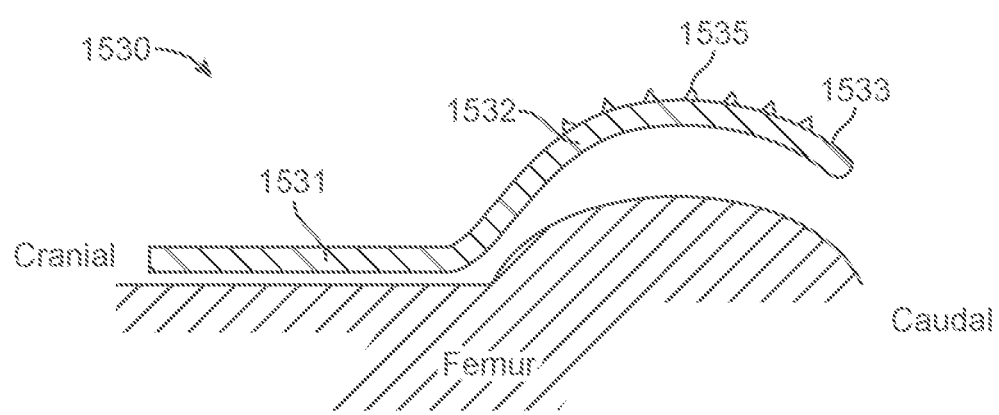
Figure 37:
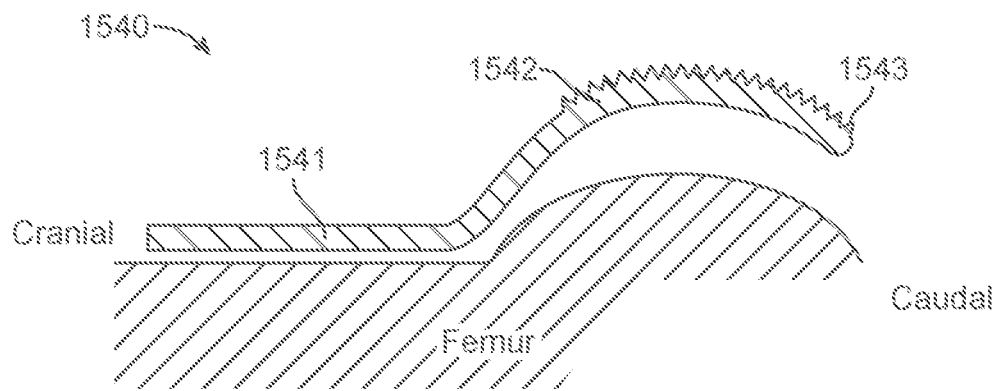
Figure 38:
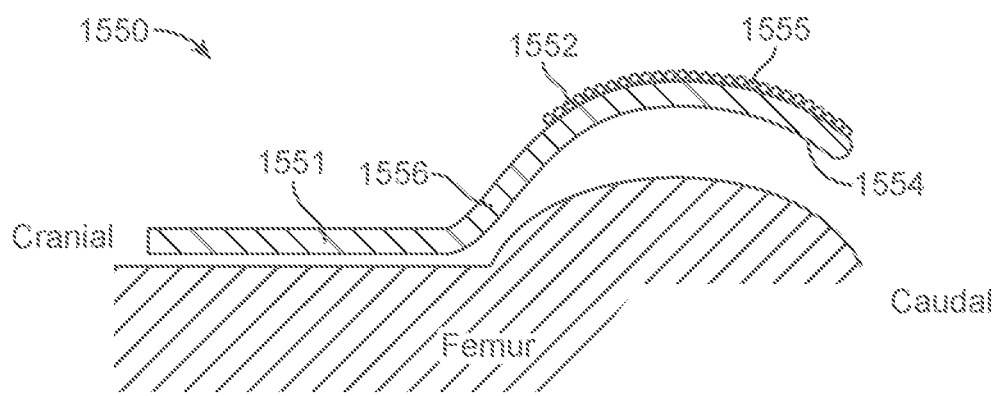

FIG. 36 depicts an implant 1530 with projections 1535 on the superior surface 1533 of the displacement section 1532. FIG. 37 depicts an implant 1540 with ridges on the superior surface 1543 of the displacement section 1542. FIG. 38 depicts an implant 1550 with a porous or granular surface 1555 on the superior surface 1554 of the displacement section 1552. In some embodiments, the spanning section (e.g., 1556) and/or the fixation section (e.g., 1551) may also have similar features for attachment of the target connective tissue. In some embodiments, a region of the displacement section may have features for attachment of target connective tissue.

Figure 39:
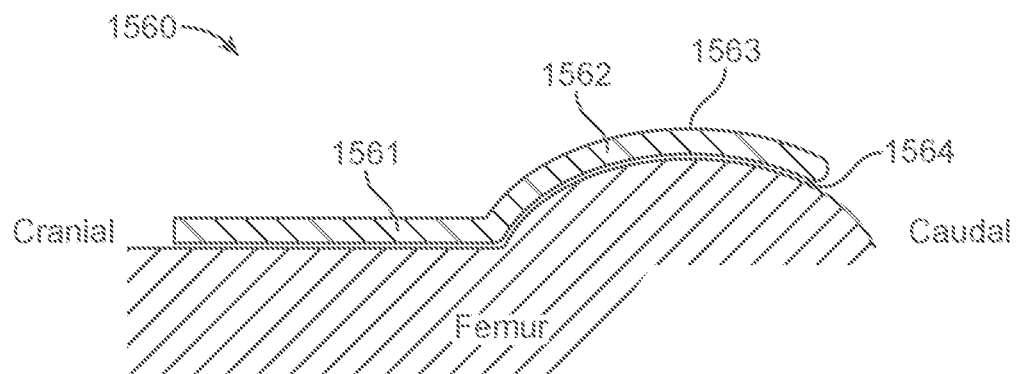

In some embodiments, the inferior surface of the displacement region may be in contact with the underlying tissue. FIG. 39 depicts an implant 1560 with the inferior surface 1564 of the displacement section 1562 in contact with the underlying tissue. In other embodiments, part of the inferior surface of the displacement section may be in contact with the underlying tissue.

In some embodiments, the inferior region of the displacement portion, spanning portion, or fixation portion may have features like channels for fibrous or bony tissue ingrowth to enable adhesion or attachment of the underlying tissue to the bearing surface. In other embodiments, the inferior region may have features like projections, microprojections, bumps, ridges, pin-like projections, granular surface etc. Attachment of any soft connective tissue underneath the inferior surface of the displacement region may minimize motion of the tissue under the implant during joint motion. In other embodiments, the inferior surface may have pins for anchoring the implanting into underlying bone.

Figure 40:
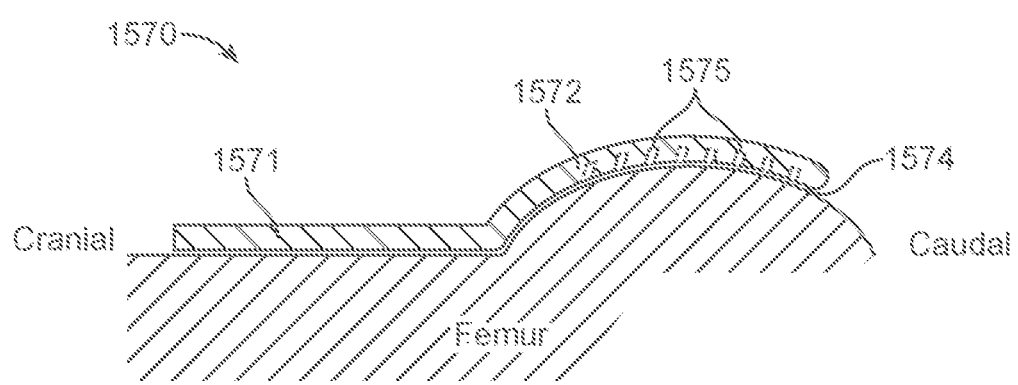

FIG. 40 depicts an implant 1570 with channels 1575 in the inferior portion 1574 of the displacement section 1572. The channels 1575 may have varying cross-sectional shapes, for example; square, circle, rectangle, oval etc., with the largest cross-sectional dimension (for example, diameter of the circle, diagonal of a square or rectangle, major diameter of an oval etc.) ranging from less than 1 mm to about 5 mm. The channels may be located across the entire inferior surface or across part of the inferior surface of the displacement section.

Figure 41:
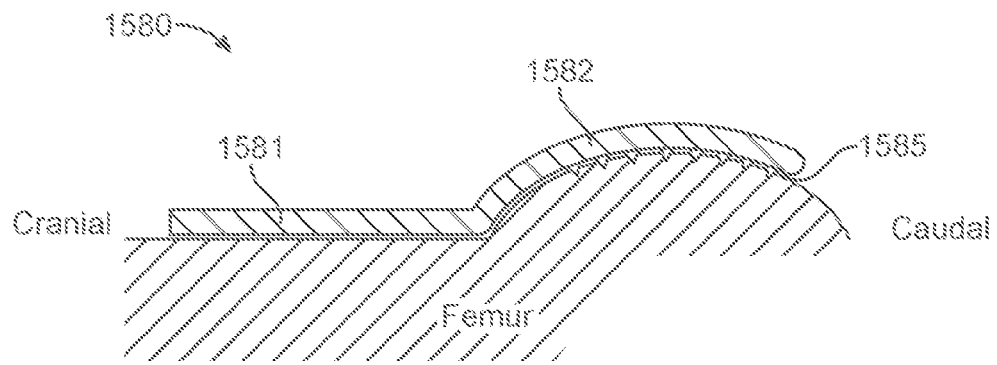
Figure 42:
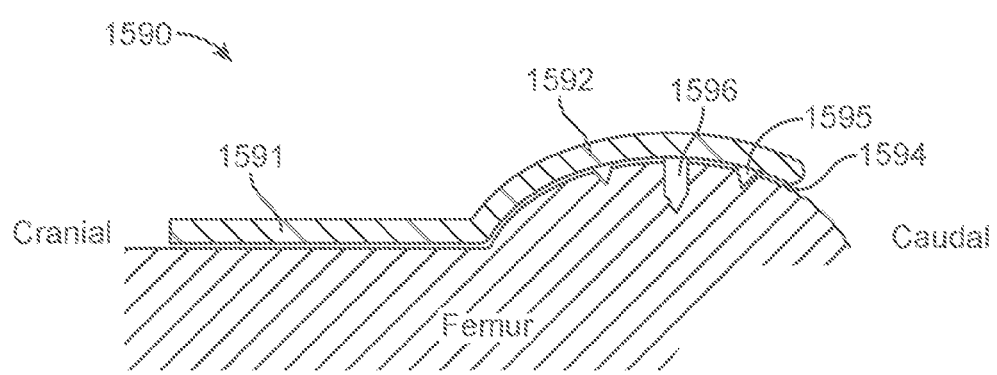

FIG. 41 depicts an implant 1580 with projections 1585 from the inferior surface 1533 of the displacement section 1582. FIG. 42 depicts an implant 1590 with pins 1595 and 1596 from the inferior surface of the displacement section 1592.

In some embodiments, the device may be a two-part device with the first part (base unit) comprising the fixation section, the displacement section (and optionally, the spanning section), and the second part (bearing unit) configured to attach to the displacement section of the base unit. In other embodiments the bearing unit may be configured to attach to the spanning section and to cover the displacement section of the base unit. The bearing unit may be configured to minimize tissue wear or to enable tissue adhesion or attachment. In one embodiment, the displacement section and the bearing unit would have features to attach the two units.

Figure 43:
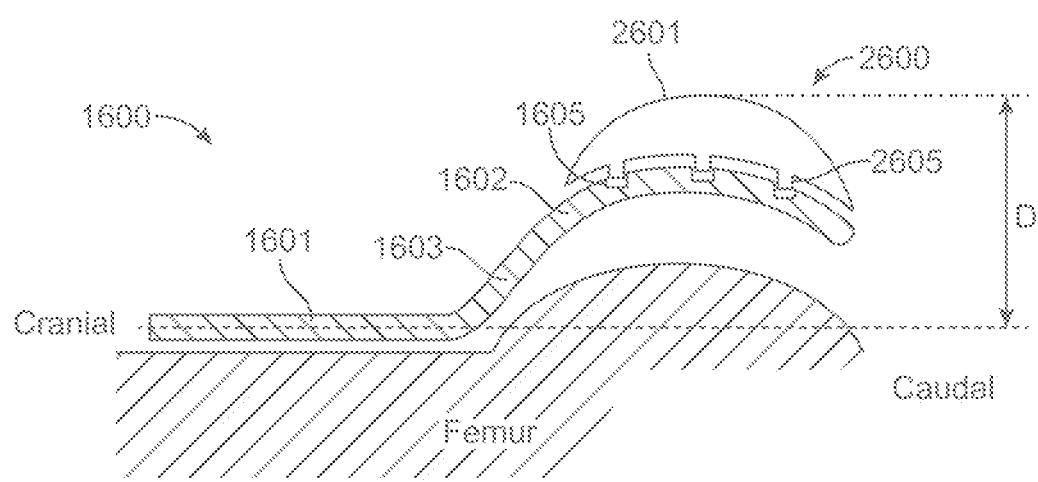
Figures 44A, 44B:
FIGS. 44A-B are exemplary embodiments of the bearing unit of a two-part device.
Figure 45:
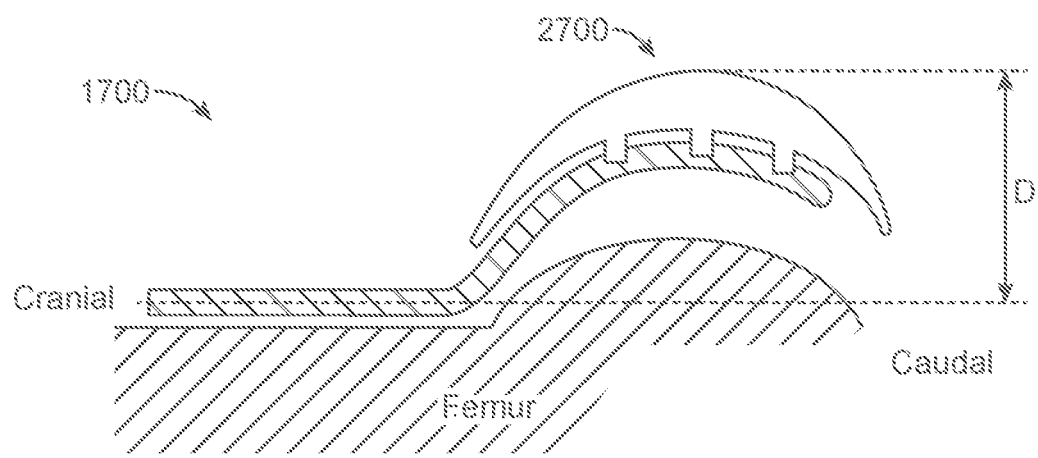
Figure 46:
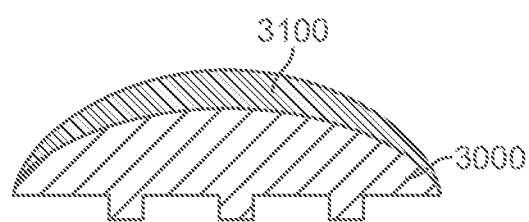
FIG. 46 is an exemplary embodiment of a composite bearing unit of a two-part device.
Figure 47:
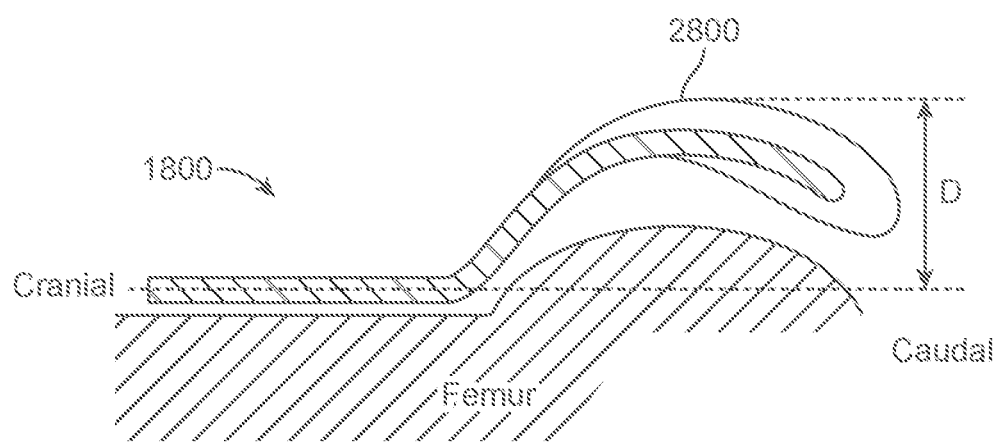

FIG. 43 depicts an exemplary two-part implant with a base unit 1600 and a bearing unit 2600. FIG. 47 depicts another exemplary embodiment of a two part implant with a bearing unit 2800 slipped over the displacement section of the base unit 1800. Attachment of the bearing unit would increase the depth of the composite implant D (FIGS. 43, 45, & 47). To alter the depth of the composite implant, bearing units of different dimensions $D_1$ and $D_2$ (FIG. 44) may be attached intra-operatively to a base unit before it is anchored to the target site or to a base unit that has been anchored to the target site (e.g., femur, tibia etc.) to obtain the necessary target connective tissue displacement. In some embodiments, the bearing unit may cover the entire displacement section of the base unit. In other embodiments, the bearing unit may cover part of the displacement region. In some embodiments, the bearing unit 2700 may extend beyond the displacement section of the base unit 2700 (FIG. 45). The bearing unit may be rigid, or may comprise of a rigid base 3000 with a compliant surface 3100 (FIG. 46).

Figure 48:
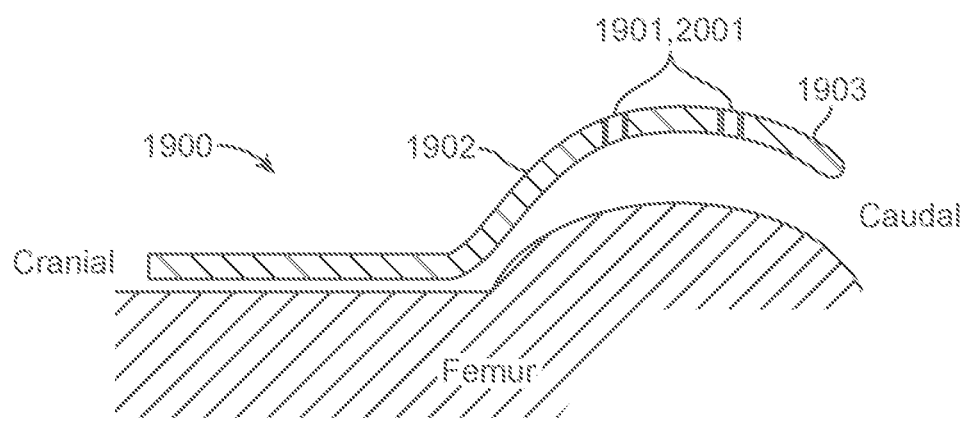
Figure 49:
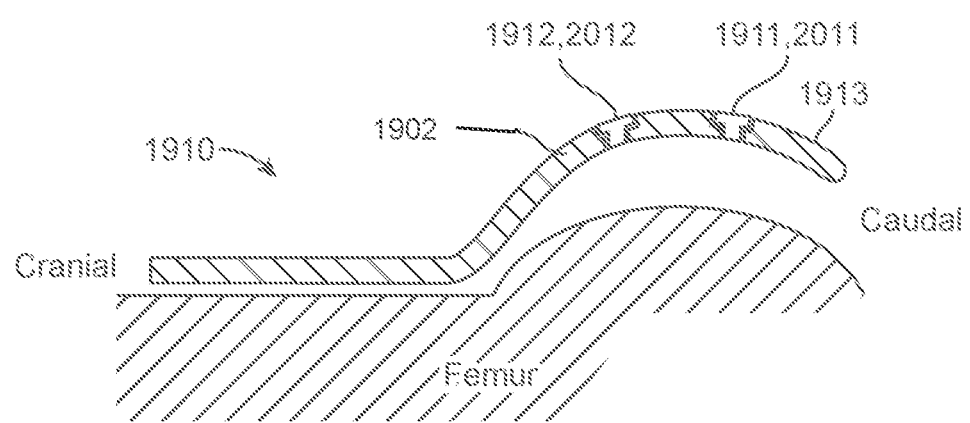
Figure 50A:
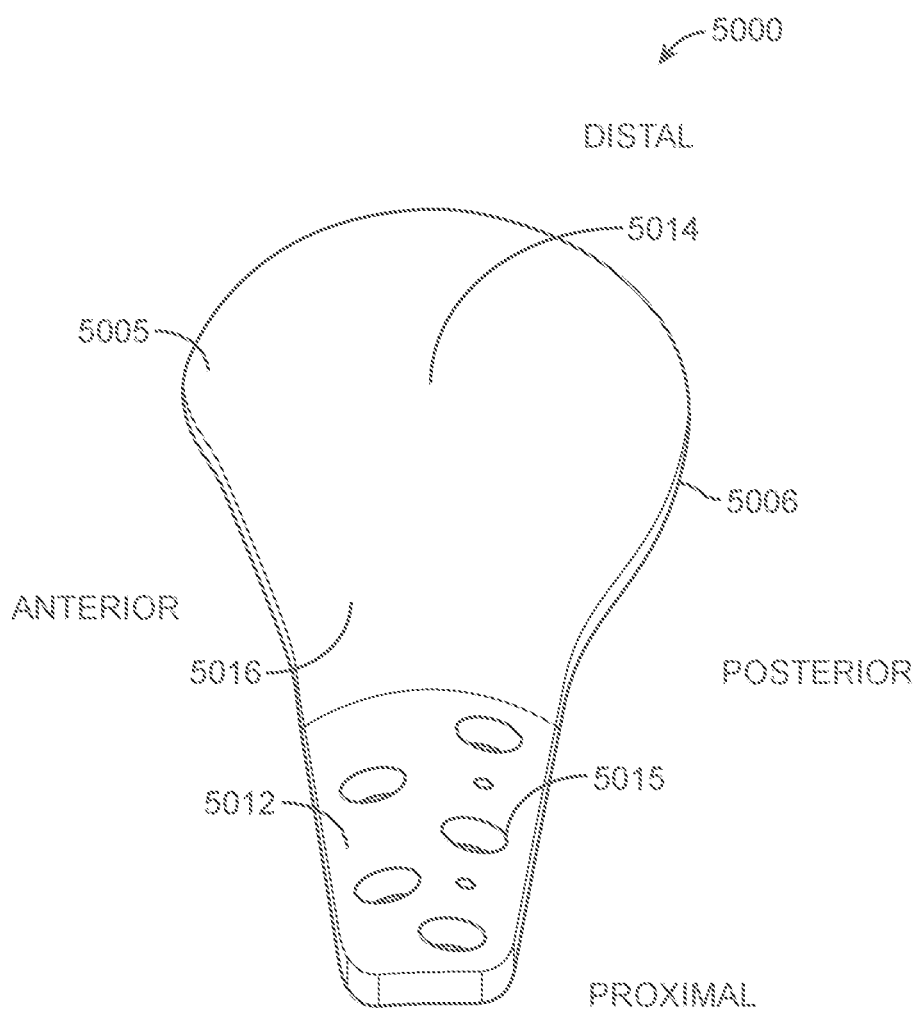
Figure 50B:
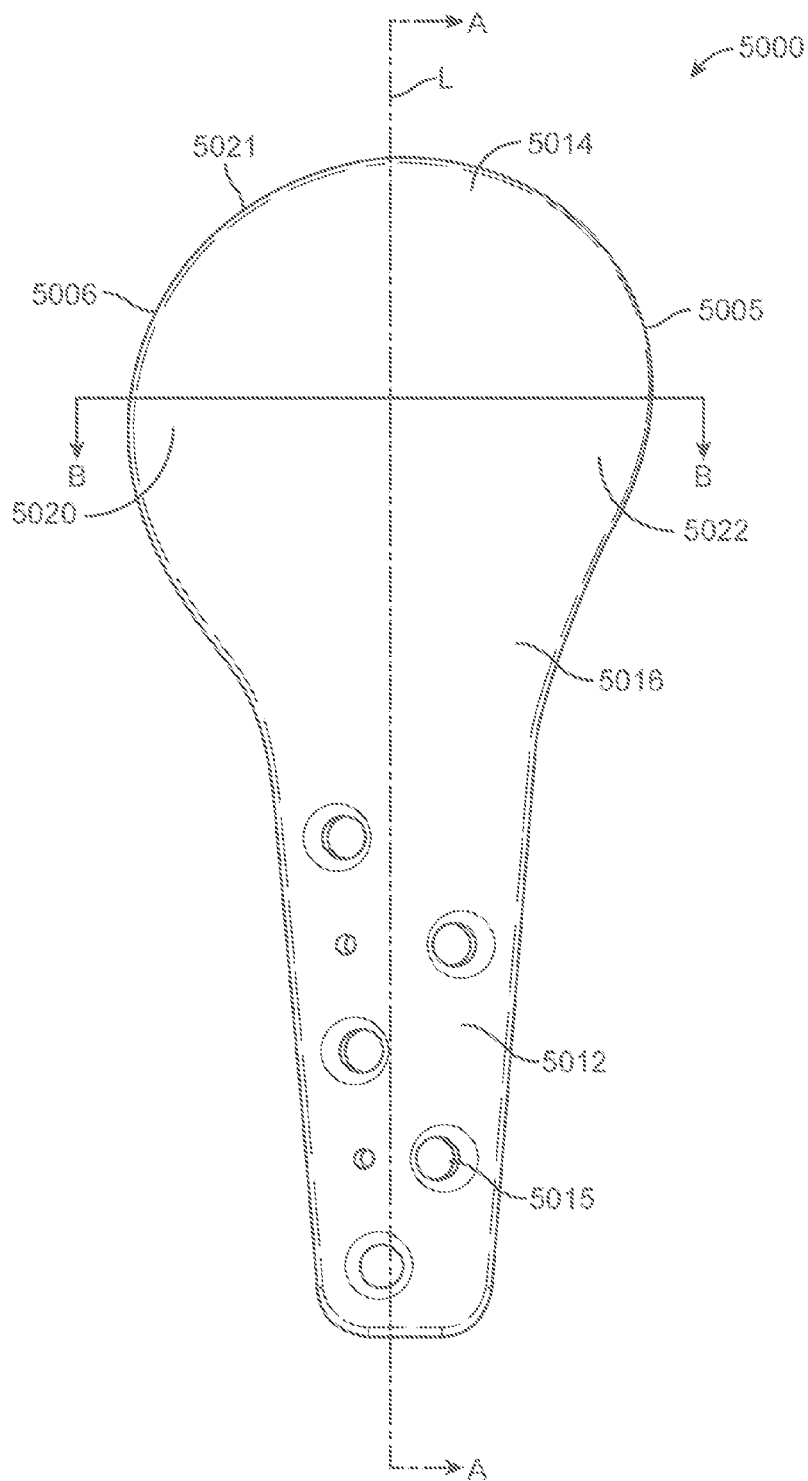

In some embodiments, the displacement region may have channels to assist in positioning, placement or temporarily anchoring of the implant intra-operatively. FIG. 48 depicts an implant with channels 1901 in the displacement section 1902 to assist in positioning of the implant during a percutaneous or minimally invasive surgery. FIG. 49 depicts an implant with channels 1911 and 1912 in the displacement section 1902 to assist in positioning of the implant during a percutaneous or minimally invasive surgery. The channels may be covered with caps (e.g., 2001, 2012, 2011) configured to fit into the channels to render the bearing surface of the displacement region completely smooth and substantially devoid of any discontinuities.

While FIGS. 33-49 illustrate exemplary embodiments of the present invention in relationship to the distal femur, it will be evident to one skilled in the art that the invention may further be adapted to various other joint locations.

FIGS. 50A-E and 51 depict another exemplary prototype of implant 5000 for treating medial osteoarthritis for the right knee. Implant 5000 may have any of the attributes, shapes, dimensions, materials, or other features of the embodiment of FIGS. 18A-D, with the possible additions or variations described hereinbelow. Fixation portion 5012 is configured and dimensioned for attachment of the implant to the lateral side of the distal femur. The implant may be attached with screws positioned in the screw holes 5015. Displacement portion 5014, the region for displacing the IT band, is connected to fixation portion 5012 through spanning section 5016. The displacement of the tissue can be altered by changing the length, shape, and angle of the spanning section 5016, the shape, thickness and orientation of displacement portion 5014, and other aspects of the implant as described herein.

While the overall size of implant 5000 is preferably minimized, displacement region 5014 should be large enough such that the IT band does not slip off its surface at any point along its trajectory of motion from full knee flexion to full extension. In addition, the shape, size, and curvature of the displacement region 5014 are selected such that the IT band, at any point along its range of motion, is engaged in a direction perpendicular to a tangent to the surface of the displacement region and is not engaged by one of the edges of the implant. It may be seen in the lateral elevational view of FIG. 50B that implant 5000 preferably has a shape which is asymmetrical about a longitudinal axis L drawn in the cranial-caudal direction through the midline of the implant. The posterior edge 5006 extends further away from axis L than the anterior edge 5005 such that the posterior portion 5020 of displacement region 5014 has a larger area than the anterior portion 5022. This larger extension in the posterior direction ensures that the IT band is engaged by the implant throughout its full range of motion and does not slip off the surface of the displacement region 5014 on the posterior side when the knee is fully flexed. At the same time, the posterior edge 5006 is tailored to avoid contact with tissue on the femoral condyle or the tibia throughout the full range of knee motion, particularly full flexion. The anterior portion of the displacement region is large enough to ensure engagement with the IT band during full extension, yet to avoid contact between the anterior edge and the patella or associated tendons.

As described earlier, the displacement portion 5014 can be configured and dimensioned to vary the displacement of the tissue during flexion/extension, minimize contact with underlying tissue etc. For example, the posterior edge 5006 of the implant (also 5020 in FIGS. 50B and 5045 in FIG. 51) may be elevated higher relative to the underlying tissue compared to the posterior edge 706 of the embodiment of FIGS. 18A-D. This additional elevation could accommodate more tissue under the implant and minimize any soft tissue impingement during flexion/extension. In one embodiment, the gap between the posterior edge of the implant and the underlying tissue is preferably at least 1 mm, more preferably at least 3 mm, most preferably at least 5 mm, when implant 5000 is implanted at the target location on the femur. To achieve this higher elevation, the posterior portion 5020 may be curved at a higher radius than the anterior portion

Figure 51:
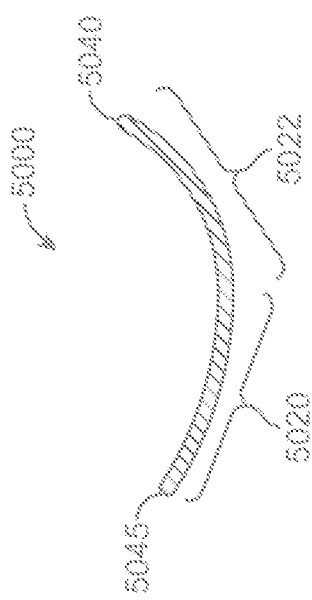
Figure 50E:
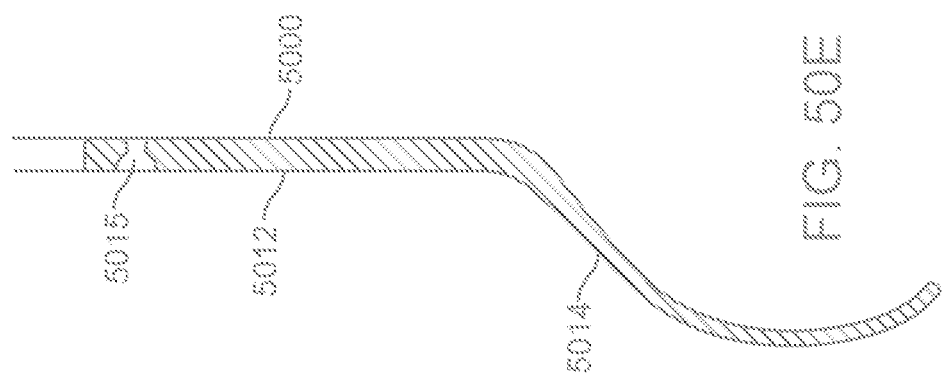

5022, as shown in FIG. 51. Alternatively or additionally, the posterior edge 5045 may be bent or curved upwardly away from the underlying bone.

Similarly, in one embodiment, the anterior region (5030) of the displacement portion can be contoured to minimize any lateral maltracking of the patella during high flexion, as shown in FIG. 50D. The anterior distal surface (5030) of the displacement portion can be shaped so as to minimize any risk of IT Band irritation by ensuring a larger contact surface between the implant and the IT Band during high flexion. In another embodiment, the posterior distal edge 5021 in FIG. 50B (also 5035 in FIG. 50D and 5040 in FIG. 51) can be rounded off and extended toward the underlying tissue/bone far enough so that the IT Band is not exposed to an implant "edge" during flexion, while avoiding any contact with the underlying tissue.

Figure 52:
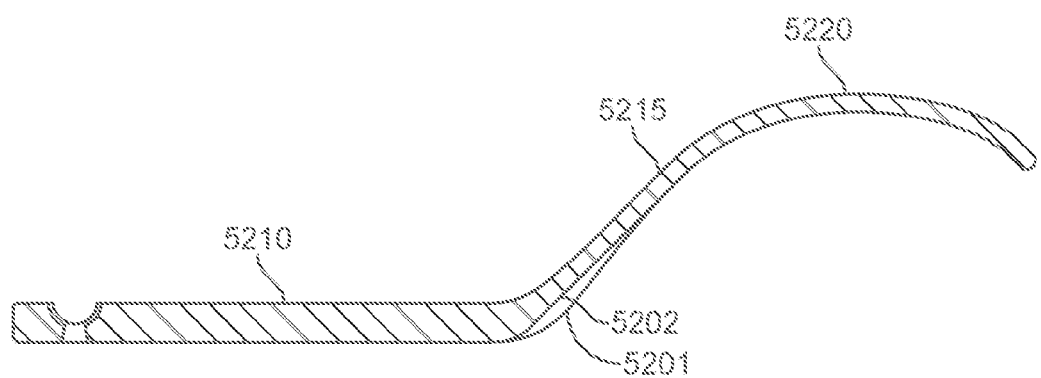
FIG. 52 shows the cross-sectional views of two implants of the present invention.

The implants of the present invention are subject to varying loads during gait due to the flexion/extension of the knee as well as the alternating weight-bearing role of each limb during gait. Additionally, the load applied on the implant due to the tissue crossing the lateral surface of the implant depends on whether the individual is walking, jogging, running, climbing stairs etc. In one embodiment, the implant is configured to be rigid through the entire range of lateral loads such that the displacement portion of the implant remains substantially stationary relative to the femur to which the implant is anchored. The rigidity of the implant could be altered by choice of material, increasing the thickness of the entire implant or increasing the thickness of certain regions of the implant. In another embodiment, the implant may be designed to provide some flexibility at the higher loads experienced during running or climbing stairs. The flexibility of the implant could result in the displacement portion of the implant bending closer to the lateral condyle at higher loads. For example, FIG. 52 is a cross-sectional view of an exemplary implant of the present invention showing two different possible thicknesses for spanning section 5201. The implant is anchored to bone through the fixation portion 5210. The displacement region of the implants 5220 is connected to the fixation portion through the spanning section 5201. Spanning section 5201 may be thicker or thinner (as shown at 5202), allowing the rigidity of the implant to be selected to provide the desired degree of deflection as it is subjected to a load due to the IT Band crossing the displacement section 5220. The thickness of the spanning section could be varied to have a rigid implant or a flexible compliant implant in the range of mechanical loads on the displacement portion. Similarly, the thickness of the entire implant could be varied to have a rigid implant or a flexible compliant implant.

Figure 54:
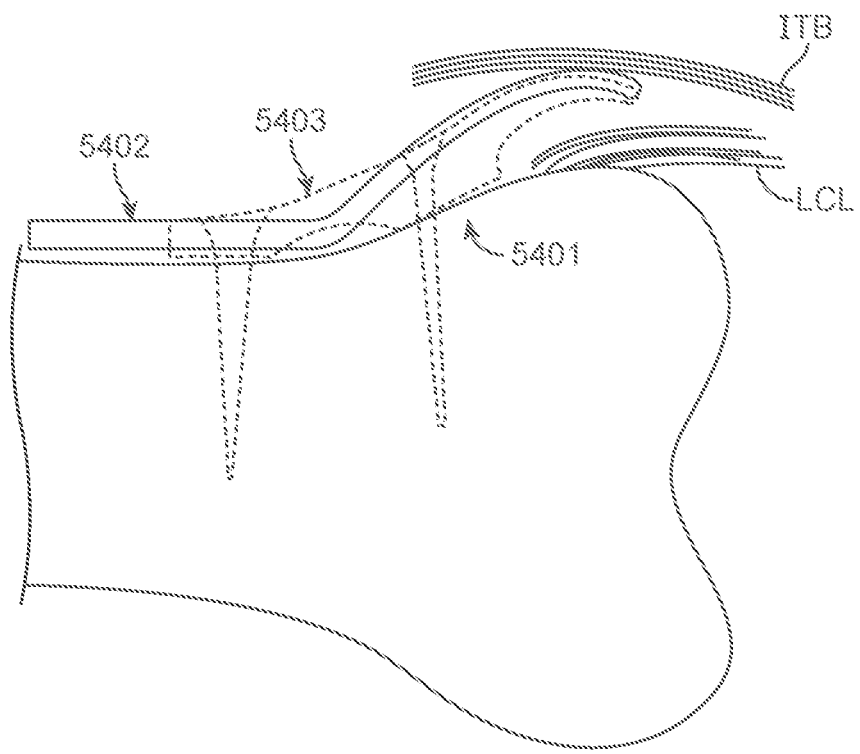
FIG. 54 is a prosthesis for lateral displacement of the IT Band in the right knee in accordance with yet another exemplary embodiment of the present invention.

FIG. 54 describes an alternative embodiment of the device for lateral displacement of tissue from the lateral condyle of the femur. Implant 5403 has a fixation portion located somewhat more distally than in other embodiments, with at least one fixation surface 5401 configured to rest on the lateral condyle. These distal fixation surfaces may be directly under or just proximal (superior) to the surface of the displacement portion that engages the IT Band, but are still proximal to the attachment of the lateral collateral ligaments (LCL) and other important tissues which attach to the more distal area of the lateral condyle. It is anticipated that these distal fixation surfaces of the device would be shaped to match the typical shape of the lateral surface of the condyle. The fixation surfaces might also be located towards the anterior and posterior edges of the device, to maximize stability of the implant under varying loads. This design may have several advantages. First, by locating the fixation surface(s) 5401 more distally, closer to the displacement surface of the device, the bending stresses on the spanning section of the device are much lower. This could give the device an additional margin of safety in stress and fatigue loading, or allow the device to be made thinner, or allow the device to be made from a lower-strength material. For example, this device or portions of it might be molded from PEEK (polyetherketone) rather than metals such as titanium. Second, this device may be more stable. Since the condyle is much wider in the anterior-posterior direction than the femoral shaft, the device will have a much wider, more triangular footprint with lower potential twisting stresses. Third, the device may have a shorter shaft (5403) compared to the shaft in other embodiments of the present invention (5402). Since the fixation surface is much nearer to the tissue displacement surface, the cantilever forces tending to raise the proximal end of the device will be lower, and the proximal end of the device can be shortened accordingly. This might enable the device to be implanted through a smaller incision. Fourth, since the distal fixation surfaces are located directly on the lateral condyle, the displacement of the displacement surface relative to the surface of the lateral condyle will be a much more predictable.

Figure 53A:
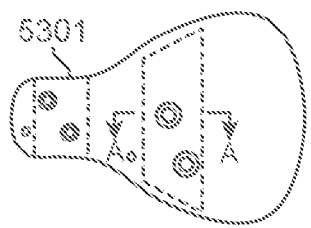
FIGS. 53A-C are views of a prosthesis for lateral displacement of the IT Band in the right knee in accordance with yet another exemplary embodiment of the present invention, wherein 53A is a top view, 53B is a cross-sectional view of the implant placed on the lateral condyle, and 53C is a cross-sectional view of the implant sectioned through A-A.

FIGS. 53 A-C show a further elaboration of the design described in FIG. 54. Although the distal fixation surfaces of the implant 5301 in FIG. 53A might be located near the anterior and posterior edges of the implant for maximum stability, it may not be necessary to locate fixation screws in those same areas. For example, if the surgical incision is made along the posterior edge of the ilio-tibial band (ITB), it may simplify the surgery to place the fixation screws generally nearer to the posterior edge of the device as shown in FIG. 53A.

Figure 53B:
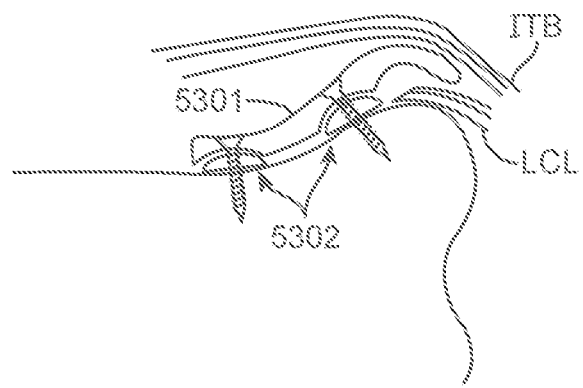

In order to accommodate the variation in femur shape from one patient to another, it may be preferable to design in some flexibility to the orientation of the fixation surfaces of this device. FIG. 53B shows one method of providing this flexibility. In FIG. 53B, the fixation surfaces are made of separate elements or feet 5302 that rotate or are otherwise movable relative to the implant 5301. Screws extend through holes in the fixation portion of the implant and through holes in the feet 5302, but the holes through the feet are somewhat slotted, to accommodate rotation of the feet relative to the implant. This figure also shows the relationship of the device to the ilio-tibial band (ITB) and the lateral collateral ligaments (LCL).

The interface between the device and the feet is shown in this two-dimensional drawing as arcuate. In three dimensions, this interface might be cylindrical, or it might be curved in the anterior-posterior dimension as well, following the general curve of the femoral surface and the device in the anterior-posterior direction. Alternatively, these feet might be independent of one another, with a generally spherical interface relative to the device.

Figure 53C:
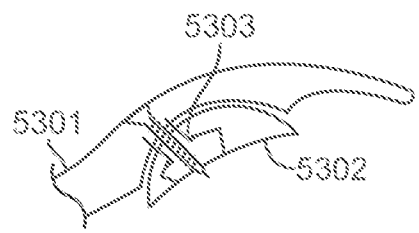

While the feet shown in FIG. 53B might be separate and independent parts from the device, this might make it difficult to hold all of the parts in place during the implantation procedure. Therefore, it might be preferable to have the feet 5302 coupled to the device 5301 while still enabling relative sliding or rotation. One embodiment is shown in FIG. 53C. In this embodiment, the slots in the feet have a countersink from the bottom side, and a collet or hollow rivet 5303 is inserted through the bottom of the feet with a press-fit into the hole in the device. This collet keeps the feet from falling away from the device, while still permitting the desired rotation of the foot and the screw.

Figure 55A:
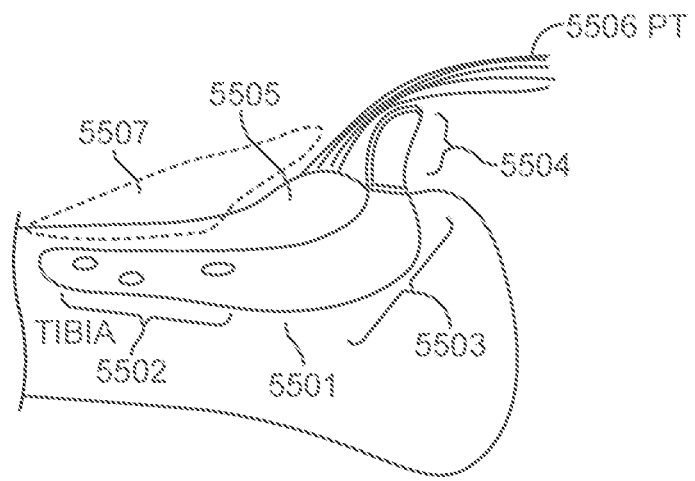
FIG. 55A-C are views of a prosthesis to improve cosmesis in accordance with yet another exemplary embodiment of the present invention.
Figure 55B:
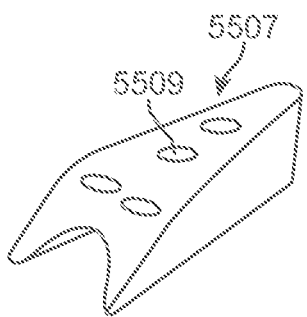
Figure 55C:
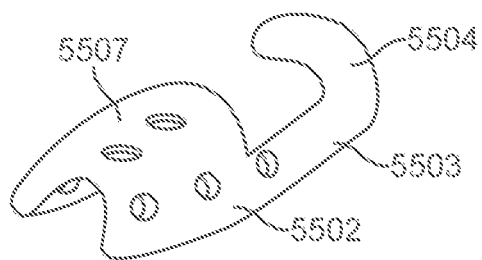

FIG. 55A-C shows an additional prosthesis to improve cosmesis in accordance with yet another exemplary embodiment of the present invention. Displacement of soft tissue around a joint could result in an unsightly bump. For example, displacement of the patellar tendon by implantation of a device under the patellar tendon just superior to the tibial tuberosity could create an unsightly bump. FIG. 55A illustrates a patellar tendon displacement device (5501) like that described in connection with FIG. 9, with fixation portion 5502, spanning portion 5503 and displacement portion 5504. The tibial tuberosity 5505 and patellar tendon 5506 are also shown. In one embodiment, a pyramidal-shaped prosthesis (5507) positioned on the anterior surface of the tibia distal to and above the tibial tuberosity may be implanted to reduce the "bump" and improve cosmesis. As shown in FIG. 55B, prosthesis 5507 may be concave on its lower side to match the surface of the tibia, and wedge-shaped as to have a low profile on its caudal end and higher profile on its cranial end. When implanted prosthesis 5507 may slope upwardly (ventrally or anteriorly) from the bone surface at the caudal end of the prosthesis up to the level of displacement of the patellar tendon at the cranial end of the prosthesis. The prosthesis could thus provide a smooth anterior tibial ridge leading directly to the re-positioned patellar tendon. The prosthesis could be made of a rigid plastic or metal, but it could also be manufactured from a slightly deformable material such as a silicone, urethane, or other implantable plastic. It might also have a composite construction, with a stronger element on the posterior surface against the tibia for secure fixation, and a softer anterior surface. The anterior surface might preferably be made of a plastic which could be sculpted by the surgeon at the time of implant to give the most aesthetically pleasing final appearance. The prosthesis would be made of highly biocompatible materials, optimized for supporting the long term health of the skin and other surrounding tissues. This might be optimized by using materials with a porous surface into which the surrounding tissues grow. The prosthesis could be affixed directly to the tibia with screws, adhesive or other attachment means, and may have appropriate coupling means for fasteners, e.g. screw holes 5509. It might also be designed for attachment to the fixation portion 5502 of the displacement device 5501. Further, prosthesis 5507 may be an integral part of displacement device 5501, or may be fixed to the displacement device with adhesive, screws or other fasteners, as shown in FIG. 55C. This might make it easier to implant and fix the prosthesis through the same incision which is used to place the displacement device.

In another embodiment the device shape could be optimized by the surgeon at the time of implantation. It may be shaped to cover the fixation portion of the displacing implant, or it could be placed beside it.

FIGS. 56 A-D illustrate an exemplary embodiment of an inserter device of the present invention which can be used to manipulate and hold prosthesis of the present invention in place during the surgical implantation process. This device (5601) utilizes two pins 5602 which can be placed through any two of the screw holes in the prosthesis. They may be angled slightly together, to prevent the pins from sliding out of the holes during manipulation. The device is designed with one pin attached to an inner rod 5603 and one pin attached to outer shaft 5604. The proximal end of shaft 5604 is attached to handle 5605, and the proximal end of rod 5603 is threaded and has threaded knob 5606 screwed onto it. A flat or keyway on rod 5603 prevents it from rotating relative to shaft 5604. Therefore, clockwise rotation of knob 5606 pulls the two pins closer together, and counter-clockwise rotation of knob 5606 increases the space between the two pins. Completely unscrewing knob 5606 allows the rod 5603 to slide completely out of shaft 5604, for ease of cleaning and complete sterilization.

Figure 56C:
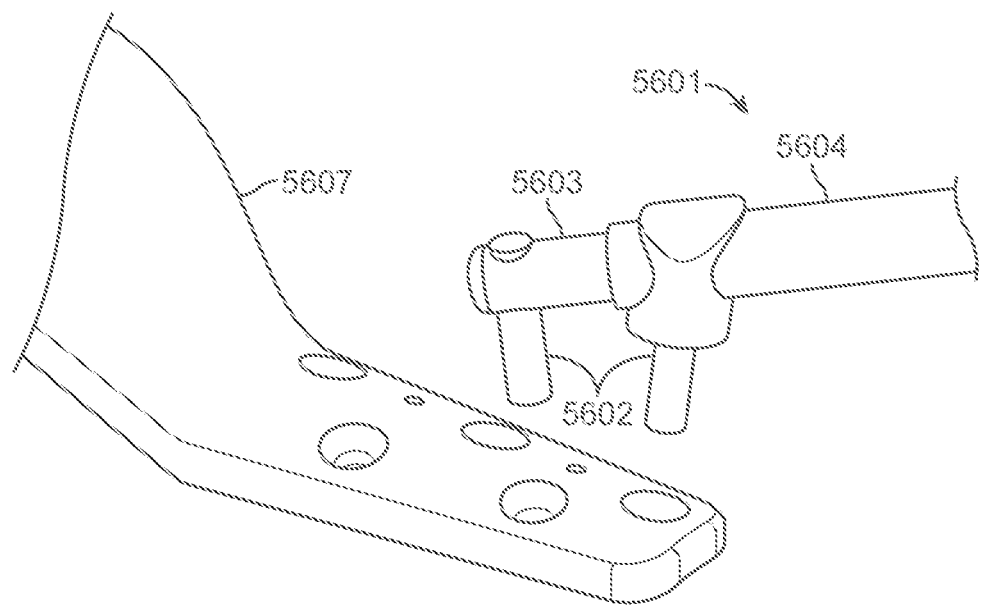
Figure 56D:
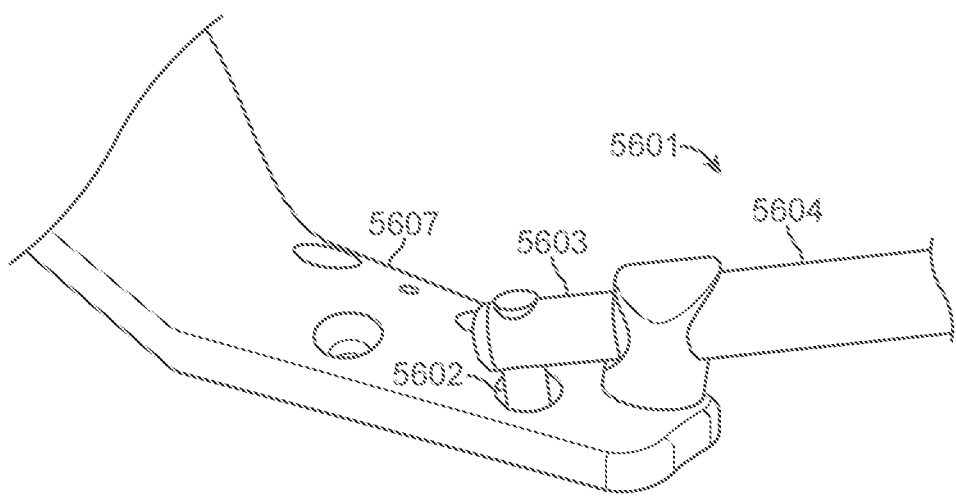

During implantation, the surgeon can use the device 5601 to grasp the device from a wide variety of angles, depending upon which pair of holes is selected. In FIG. 56A, the device is angled superiorly and laterally. In FIG. 56B the device is positioned superiorly. FIG. 56C shows a close-up of the device in FIG. 56B as the pins approach the screw holes on the prosthesis. FIG. 56D shows a close-up of the device in FIG. 56A with the pins locked into the screw holes of the prosthesis.

The device might preferably be at least long enough for the surgeon to hold it during fluoroscopy of the knee and implant, without exposing the surgeon's hand to X-Rays. Once the surgeon has confirmed using fluoroscopy or other techniques that the device is properly positioned, the surgeon can place Kirschner wires or bone screws to permanently attach the device to the femur. Once a few K-wires or screws have been placed, the device can be loosened and removed, and additional screws can be placed in the holes previously occupied by the pins 5602 of the device.

Figure 57A:
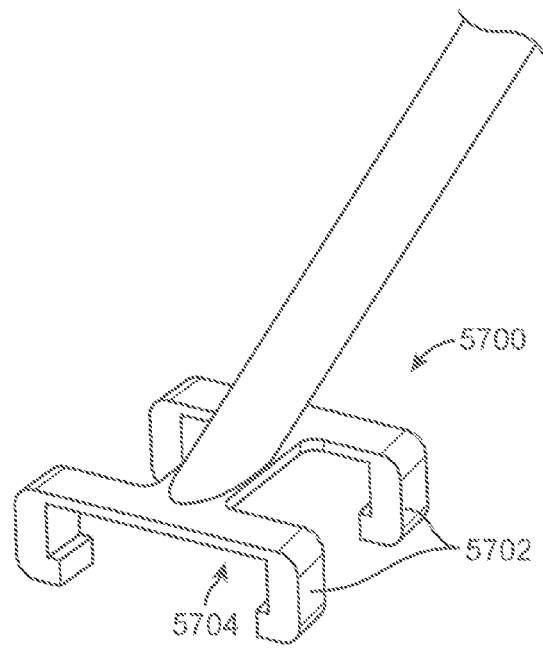
FIGS. 57A-B are views of an exemplary embodiment of an inserter device for implanting the prosthesis of the present invention.
Figure 57B:
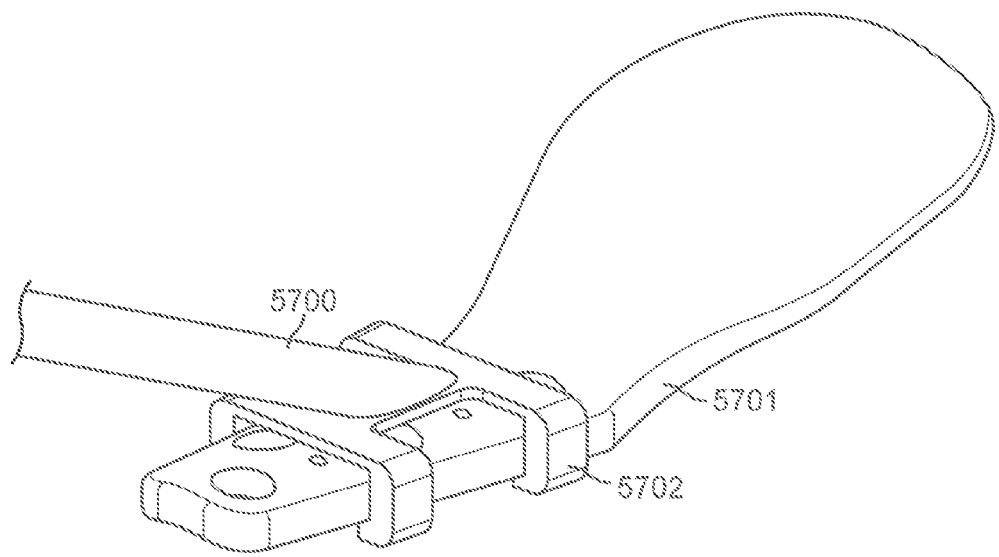

FIGS. 57A-B show an alternative embodiment of an inserter device 5700 that grasps the edges of the shaft (fixation portion) of the prosthesis 5701. Inserter 5700 has opposing arms 5702 forming a channel 5704 configured to slide over the shaft of the prosthesis 5701. The device could be placed over the prosthesis at the proximal end of the shaft, and then advanced distally until the device firmly grasps the shaft. This device might alternatively have a mechanism that allows the jaws to move apart from one another, so that the device could be removed without the need to slide it proximally along the tapered shaft.

FIGS. 58A-B show an exemplary embodiment of a dissection device 5800 that is shaped to enable proper dissection of the tissue pocket in which the prosthesis of the present invention is placed. The ilio-tibial band tissue commonly has small adhesions to the underlying tissue, and this device could be manipulated to free those adhesions. Device 5800 has a shaft 5802, handle 5804 and a flat blade 5806 disposed at an angle relative to shaft 5802 such that blade 5806 can be positioned parallel to a lateral surface of the femur with handle 5804 in a suitable ergonomic orientation for manipulation by the surgeon.

Figure 59A:
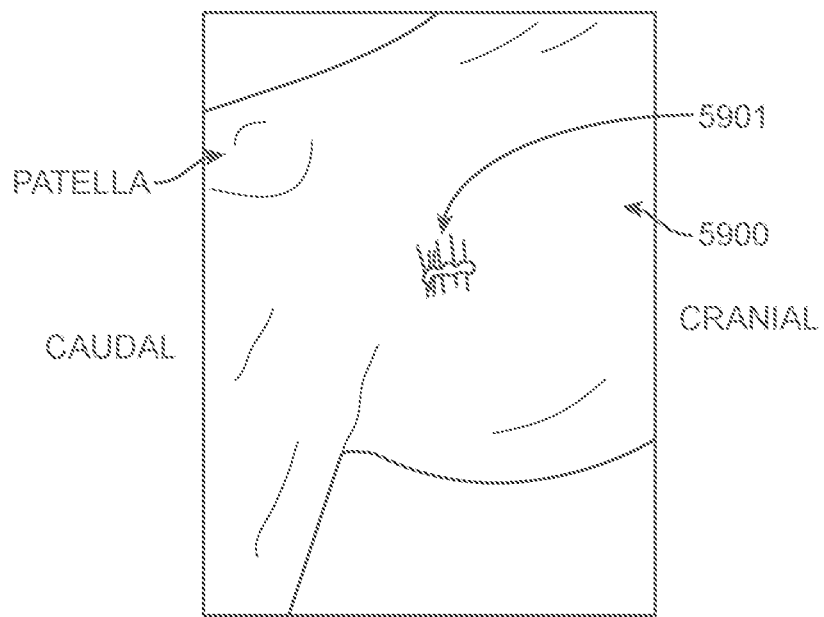
FIGS. 59A-H are views of an exemplary surgical procedure to implant the prosthesis of the present invention.
Figure 59B:
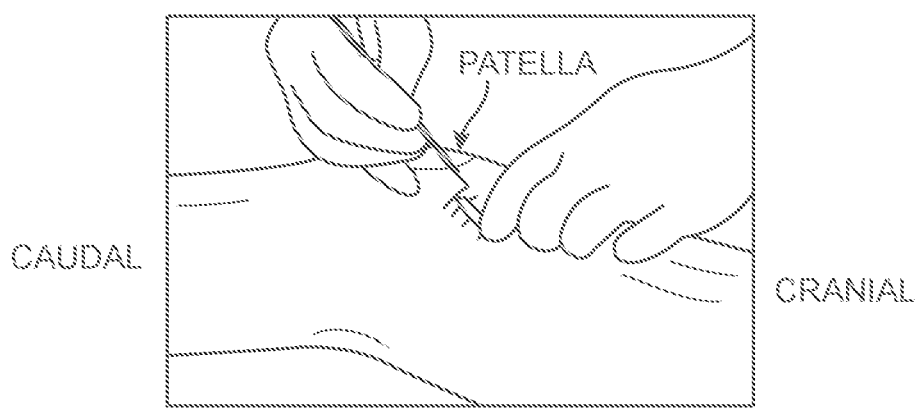
Figure 59C:
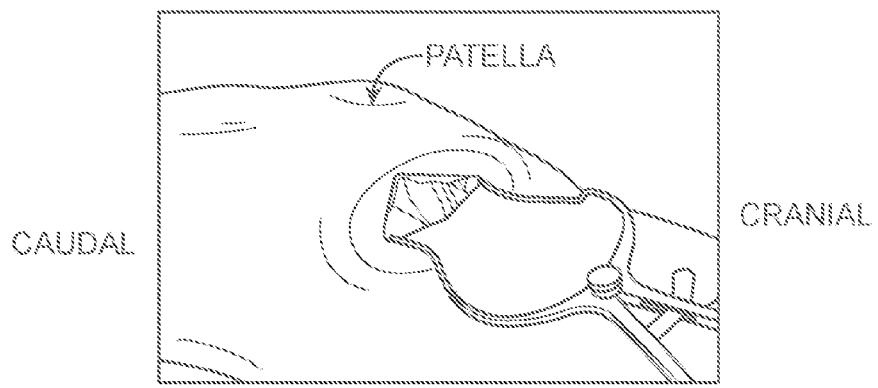
Figure 59D:
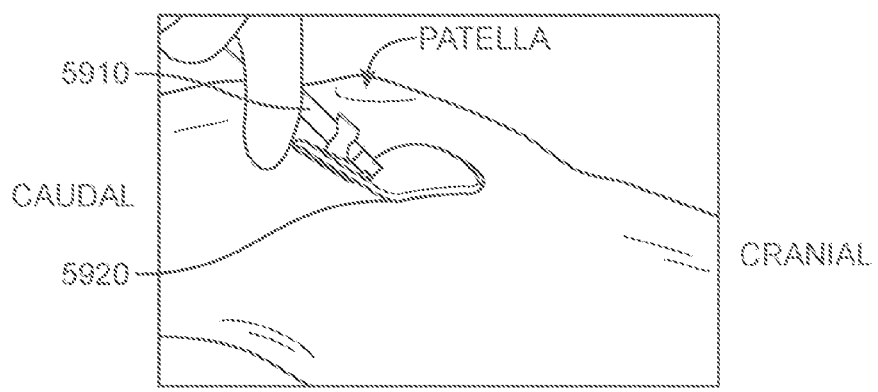
Figure 59E:
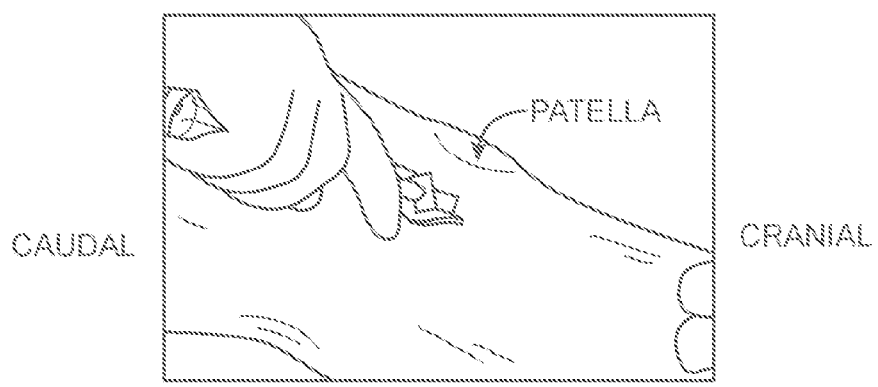
Figure 59F:
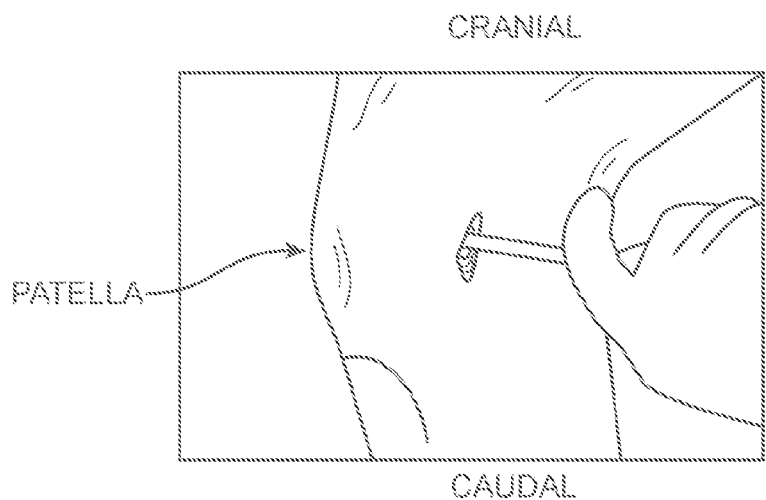
Figure 59G:
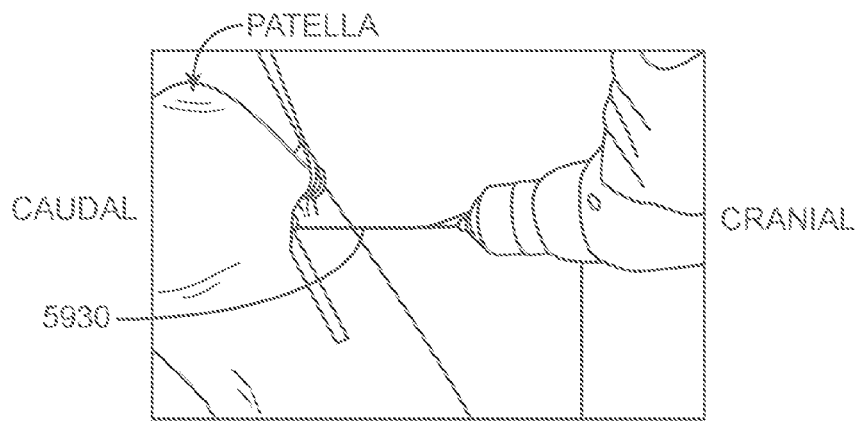
Figure 59H:
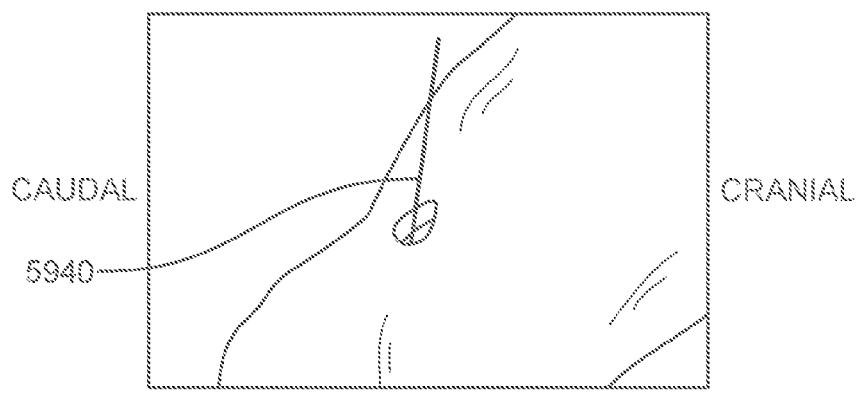

FIGS. 59A-B show an exemplary surgical procedure to implant the prosthesis of the present invention on the lateral condyle of the distal femur. The patient is placed in a lateral position and the limb is maintained at full extension. A prosthesis is then placed on the surface of the lateral condyle. Using fluoroscopic imaging and bony anatomical landmarks, the position of the prosthesis is adjusted. Using a skin marker, a line (5901) is then drawn along the fixation shaft of the implant. Using manual palpation to identify the posterior edge of the IT Band, a skin incision (length ~5 cm) is then made along the marked line (FIG. 59B). The incision is then extended down to the bone, cutting through the interval between the posterior edge of the IT Band and the anterior edge of the biceps femoris. Using blunt dissection or the dissection device (FIG. 58A), fibrous attachments between the IT Band and the underlying bone are removed to create a pocket for the prosthesis of the present invention. Fluoroscopic imaging of the dissection device inserted into the tissue pocket can be used to assess the location of the pocket, and if any additional fibrous tissue clearance is required. As shown in FIG. 59D, the prosthesis (5920) is then attached to the insertion device (5910) and inserted into the tissue pocket. In one embodiment, the prosthesis attached to the inserter device is inserted into the tissue pocket in the anterior direction (FIG. 59D) and then rotated in the caudal direction (FIG. 59E). Insertion of the implant into the tissue pocket can be done with the knee in full extension or in slight flexion. The location of the prosthesis is then adjusted under fluoroscopic guidance using bony anatomical landmarks. K-wires (5930) are driven into the k-wire holes to provide temporary fixation of the implant (FIGS. 59G-H). The inserter is then detached from the implant and the position of the implant is confirmed under fluoroscopic guidance. Screws are then driven into the femoral shaft through the implant fixation portion. The knee is flexed to ensure there is no tissue impingement. The IT Band—biceps femoris interval is sutured together and the skin incision is then closed.

As will be evident to one skilled in the art, the dimensions of the exemplary embodiments above can be altered to address differences in joint size, condyle size, level of the tissue displacement etc. as well as to enable positioning and securing the implant at the surgical site while minimizing trauma to the surrounding bone, tendons, muscles, ligaments and other anatomical structures.

While the invention has been illustrated by examples in various contexts, the devices of the present invention may be used to displace any of the muscles and connective tissues around the knee to achieve a therapeutic effect. For example, the muscle displaced could be the popliteus muscle, gastrocnemius muscle, the plantaris muscle, vastus lateralis muscle, vastus intermedius muscle, vastus medialis muscle and the semimembranous muscle. Alternatively, the tendon associated with any of the muscles could be displaced.

While the invention has been illustrated by examples in various contexts of treating human and animal osteoarthritis associated with force imbalances in a joint, it will be understood that the invention may also have application to treatment of focal defects caused by trauma or other reasons. In particular, pain associated with focal defects in the medial condyle in the knee may be reduced by applying the devices and methods of the invention to reduce loading on the medial condyle.

Alternatively, the devices and methods of the invention could be used in conjunction with other therapies used to treat focal and diffuse lesions on the condyle. For example, the device for unloading the medial condyle could be used in conjunction with microfracture or autologous chondrocyte implantation (ACI) therapy of a focal lesion on the medial condyle.

Other applications of devices and methods of the invention include use in conjunction with meniscal repair treatment to reduce loading on the medial condyle. The contoured bearing surface for the iliotibial band could also alleviate pain associated with the iliotibial band friction syndrome. Another application includes use in conjunction with total joint replacement devices to alter the mechanical forces on the new joint, thereby increasing the stability of the replaced joint and reducing the risk of implant wear. The invention may further be adapted to displace tissues acting on various other joints so as to reduce or otherwise alter loads therein, including the elbow, shoulder, wrist, fingers, spine, ankle, interphalangeal joints, jaw or other joints. For example, the implants of the invention may be configured for attachment to the acetabulum, vertebrae of the spine, scapula, humerus, radius, ulna, carpals, metacarpals, tarsals, metatarsals, talus or other bones of the foot, among other bones.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. A method of treating at shoulder joint having first and second bones, the method comprising:
   fixing a fixation portion of a treatment device to the first bone such that a displacement portion of the treatment device engages target tissue in a pretreatment location proximate the shoulder joint; and
   displacing the target tissue from the pretreatment location with the displacement portion of the treatment device by a distance and in a direction selected to provide a therapeutic effect in the shoulder joint;
   wherein the first bone is the humerus, and said displacing further comprises altering a force acting between the humerus and the glenoid; and
   wherein said displacing is in a lateral direction.

2. A method of treating a shoulder joint having first and second bones, the method comprising:
   fixing a fixation portion of a treatment device to the first bone such that a displacement portion of the treatment device engages target tissue in a pretreatment location proximate the shoulder joint; and
   displacing the target tissue from the pretreatment location with the displacement portion of the treatment device by a distance and in a direction selected to provide a therapeutic effect in the shoulder joint;
   wherein the first bone is the humerus, and said displacing further comprises altering a force acting between the humerus and the glenoid; and
   wherein said displacing is in an anterior direction.

3. A method of treating a shoulder joint having first and second bones, the method comprising:
   fixing a fixation portion of a treatment device to the first bone such that a displacement portion of the treatment device engages target tissue in a pretreatment location proximate the shoulder joint; and
   displacing the target tissue from the pretreatment location with the displacement portion of the treatment device by a distance and in a direction selected to provide a therapeutic effect in the shoulder joint;
   wherein the displacement portion comprises a bearing surface configured to atraumatically engage the target tissue and allow movement of the tissue thereon; and
   wherein the screws extend through the holes in a first direction and the target tissue is displaced in a second direction generally parallel to and opposite the first direction.

4. The method of claim 3, wherein the target tissue exerts a force on the shoulder joint in the pretreatment location, the target tissue being displaced so as to redirect the force.

5. The method of claim 4, wherein the force creates a moment acting on the joint, and said displacing the target tissue increases the moment.

6. The method of claim 5, wherein the moment is increased by increasing a moment arm through which the force acts on the shoulder joint.

7. The method of claim 3, wherein the bearing surface is smooth, continuous, and free of screw holes or fixation elements.

8. The method of claim 3, wherein the bearing surface is dome-shaped.

9. The method of claim 3, wherein the fixation portion and displacement portion of the treatment device form an overall L- or J-shape.

10. The method of claim 3, wherein:
displacement portion has an inner surface facing the first bone and an outer surface opposite the inner surface comprises said bearing surface, with a displacement portion thickness defined between said displacement portion inner surface and outer bearing surface;
the bearing surface being separated from the first bone by a distance greater than the bearing portion thickness.

11. A method of treating a shoulder joint having first and second bones, the method comprising:
fixing a fixation portion of a treatment device to the first bone such that a displacement portion of the treatment device engages target tissue in a pretreatment location proximate the shoulder joint; and
displacing the target tissue from the pretreatment location with the displacement portion of the treatment device by a distance and in a direction selected to provide a therapeutic effect in the shoulder joint;
wherein the fixation portion and displacement portion are generally aligned with the longitudinal axis of the first bone.

12. The method of claim 11, wherein the therapeutic effect comp-Re reducing pain in the shoulder joint.

13. The method of claim 11, wherein the therapeutic effect comprises increasing stability of the shoulder joint.

14. The method of claim 11, wherein displacing the target tissue redistributes a load between the first and second bones.

15. The method of claim 11, wherein the target tissue is displaced in a direction away from the shoulder joint.

16. The method of claim 11, wherein the displacement portion of the treatment device is configured to be spaced apart from the first bone when the fixation portion is fixed to the first bone.

17. The method of claim 11, wherein the target tissue is displaced a distance of about 5-30 mm from the pretreatment location.

18. The method of claim 11, wherein fixing comprises inserting a plurality of screws through a plurality of holes in the fixation portion of the treatment device.

19. The method of claim 11, wherein said displacing the target tissue redistributes a load on at least one articular surface in the shoulder joint.

20. The method of claim 19, wherein said displacing the target tissue increases said load.

21. The method of claim 11, further comprising positioning the displacement portion to extend over soft tissue disposed between the displacement portion and the first bone without inhibiting motion of the soft tissue.

22. The method of claim 21, wherein said positioning comprises fixing the fixation portion at a fixation location spaced from the articular surfaces of the shoulder by at least a distance corresponding to a length of a treatment device spanning section between the displacement portion and fixation portion.

23. A method of treating a shoulder joint having first and second bones, the method comprising:
fixing a fixation portion of a treatment device to the first bone such that a displacement portion of the treatment device engages target tissue in a pretreatment location proximate the shoulder joint; and
displacing the target tissue from the pretreatment location with the displacement portion of the treatment device by a distance and in a direction selected to provide a therapeutic effect in the shoulder joint;
wherein the treatment device further comprise a spanning section interconnecting the displacement portion and the fixation portion; and
wherein the spanning section is configured to elevate the displacement portion over the surface of the first bone.

24. The method of claim 23, wherein the fixation portion is disposed generally in a first plane and the spanning section is disposed at an acute angle relative to the first plane.

25. A method of treating a shoulder joint having first and second bones, the method comprising:
fixing a fixation portion of a treatment device to the first bone such that a displacement portion of the treatment device engages target tissue in a pretreatment location proximate the shoulder joint; and
displacing the target tissue from the pretreatment location with the displacement portion of the treatment device by a distance and in a direction selected to provide a therapeutic effect in the shoulder joint;
wherein fixing and displacing steps are performed following a total joint replacement to increase stability of the replaced joint.

26. A method of treating a shoulder joint having a humerus articulated in the glenoid cavity of the scapula, the method comprising:
fixing a fixation portion of a treatment device to the humerus such that a displacement portion of the treatment device engages target tissue in a pretreatment location proximate the shoulder joint; and
displacing the target tissue from the pretreatment location with the displacement portion of the treatment device by a distance and in a direction selected to alter a force acting between the humerus and the glenoid so as to provide a therapeutic effect in the shoulder joint.

27. The method of claim 26, wherein the target tissue exerts a force on the shoulder joint in the pretreatment location and said force creates a moment acting on the joint, and wherein the target tissue is displaced so as to redirect said force and increase the moment by increasing a moment arm through which the force acts on the shoulder joint.

28. The method of claim 27, wherein the therapeutic effect comprises increasing stability of the shoulder joint.

29. A method of treating a shoulder joint having a humerus articulated in the glenoid cavity of the scapula, the method comprising:
performing a total joint replacement of the shoulder joint with a joint replacement device;
fixing a fixation portion of a separate treatment device to the humerus outside the joint capsule such that a displacement portion of the treatment device engages target tissue in a pretreatment location proximate the replaced shoulder joint; and
displacing the target tissue from the pretreatment location with the displacement portion of the treatment device by a distance and in a direction selected to increase stability of the replaced joint.

* * * * *

UNITED STATES PATENT AND TRADEMARK OFFICE
CERTIFICATE OF CORRECTION

PATENT NO. : 9,931,136 B2
APPLICATION NO. : 15/017098
DATED : April 3, 2018
INVENTOR(S) : Vivek Shenoy et al.

Page 1 of 1

It is certified that error appears in the above-identified patent and that said Letters Patent is hereby corrected as shown below:

In Column 38, Claim 1, Line 9, the word "at" should be replaced with "a", therefor.

In Column 39, Claim 12, Line 26, the word "comp-Re" should be replaced with "comprises", therefor.

In Column 40, Claim 23, Line 7, the word "comprise" should be replaced with "comprises", therefor.

Signed and Sealed this
Twenty-fifth Day of September, 2018

Andrei Iancu
*Director of the United States Patent and Trademark Office*